US007998541B2

(12) United States Patent
Taugerbeck et al.

(10) Patent No.: US 7,998,541 B2
(45) Date of Patent: *Aug. 16, 2011

(54) BENZOCHROMENE DERIVATIVES FOR USE IN LIQUID CRYSTAL MEDIA AND AS THERAPEUTIC ACTIVE SUBSTANCES

(75) Inventors: Andreas Taugerbeck, Darmstadt (DE); Elvira Montenegro, Weinheim (DE); Atsutaka Manabe, Bensheim (DE); Herbert Plach, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/158,542

(22) PCT Filed: Dec. 5, 2006

(86) PCT No.: PCT/EP2006/011660

§ 371 (c)(1), (2), (4) Date: Jun. 20, 2008

(87) PCT Pub. No.: WO2007/079842

PCT Pub. Date: Jul. 19, 2007

(65) Prior Publication Data

US 2009/0247620 A1 Oct. 1, 2009

(30) Foreign Application Priority Data

Dec. 22, 2005 (DE) .......................... 10 2005 062 101

(51) Int. Cl.
C09K 19/34 (2006.01)
C09K 19/32 (2006.01)
C07D 311/80 (2006.01)
A61K 31/353 (2006.01)

(52) U.S. Cl. ............... 428/1.1; 252/299.61; 252/299.62; 514/437; 514/454; 514/455; 549/390; 549/391; 549/393

(58) Field of Classification Search .................... 428/1.1; 252/299.61, 299.62; 514/437, 454, 455; 549/390, 391, 393
See application file for complete search history.

(56) References Cited

U.S. PATENT DOCUMENTS 7,326,447 B2 * 2/2008 Taugerbeck et al. ........... 428/1.1

2006/0159784 A1 * 7/2006 Ghosal .......................... 424/762
2006/0177603 A1 * 8/2006 Taugerbeck et al. ........... 428/1.1
2009/0023802 A1 * 1/2009 Taugerbeck et al. .......... 514/455

FOREIGN PATENT DOCUMENTS

DE 102004004228 * 9/2004
JP 2001026587 A * 1/2001
JP 2003201292 * 9/2003

OTHER PUBLICATIONS

CAPLUS 2003: 550214.*
CAPLUS 1991: 639436.*
CAPLUS 2001: 72360.*
Novaroli et al: "Human Recombinant monoamine oxidase B as reliable and efficient enzyme source for screening", Bioorganic & Medicinal Chemistry, Elsevier Science Ltd, GB, BD. 13, Nr. 22, Nov. 15, 2005, Seiten 6212-6217, XP005098160, ISSN: 0968-0896, Verbindung C-21.
Kim et al.: "Estrogen receptor Ligands. 12. Synthesis of the Major", Organic Letters, Bd. 7, Nr. 3, May 2005, Seiten 411-414, XP002419869 Verbindung 12.

* cited by examiner

Primary Examiner — Shean C Wu
(74) Attorney, Agent, or Firm — Millen, White, Zelano & Branigan, P.C.

(57) ABSTRACT

The present invention relates to benzochromene derivatives of the formula I

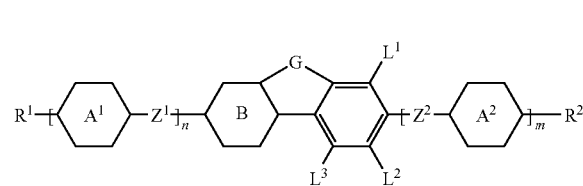

where the various parameters have the meaning indicated in the text, and to liquid-crystal media which comprise these compounds, and to the use of the media in electro-optical displays, in particular in TN, OCB, LCOS and/or IPS-LCDs, and to the use of the compounds and physiologically acceptable derivatives thereof as therapeutic active ingredients.

15 Claims, No Drawings

BENZOCHROMENE DERIVATIVES FOR USE IN LIQUID CRYSTAL MEDIA AND AS THERAPEUTIC ACTIVE SUBSTANCES

The present invention relates to benzochromene derivatives, preferably mesogenic benzochromene derivatives, in particular liquid-crystalline benzochromene derivatives, and to liquid-crystalline media comprising these benzochromene derivatives. The present invention furthermore relates to liquid-crystal displays, in particular active matrix addressed liquid-crystal displays (AMDs or AM LCDs), i.e. liquid-crystal displays which are addressed by means of a matrix of active electrical elements, such as, for example, TFTs ("thin film transistors"), varistors, diodes or MIMs ("metal-insulator-metal"), and consequently have excellent image quality. For these, use is made, in particular, of the TN ("twisted nematic") and IPS ("in plane switching") effect, in which nematic liquid crystals of positive dielectric anisotropy ($\Delta\epsilon$) are used.

In liquid-crystal displays of this type, the liquid crystals are used as dielectrics, whose optical properties change reversibly on application of an electric voltage. Electro-optical displays which use liquid crystals as media are known to the person skilled in the art. These liquid-crystal displays use various electro-optical effects. The commonest thereof are the TN ("twisted nematic") effect, with a homogeneous, virtually planar initial alignment of the liquid-crystal director and a nematic structure which is twisted by about 90°, the STN ("super-twisted nematic") effect and the SBE ("supertwisted birefringence effect") with a nematic structure which is twisted by 180° or more. In these and similar electro-optical effects, liquid-crystalline media of positive dielectric anisotropy ($\Delta\epsilon$) are used.

An electro-optical effect having excellent, low viewing-angle dependence of the contrast uses axially symmetrical micropixels (ASMs). In this effect, the liquid crystal of each pixel is surrounded in a cylindrical manner by a polymer material. This mode is particularly suitable for combination with addressing through plasma channels. Thus, in particular, large-area PA ("plasma addressed") LCDs having good viewing-angle dependence of the contrast can be achieved.

The IPS ("in plane switching") effect employed to an increased extent recently can use both dielectrically positive and also dielectrically negative liquid-crystal media, in a similar manner to "guest/host" displays, which can employ dyes either in dielectrically positive or dielectrically negative media, depending on the display mode used.

Furthermore, LCOS displays and displays based on a birefringence effect, such as OCB displays, are also interesting. Since the operating voltage in liquid-crystal displays in general, i.e. also in displays utilising these effects, should be as low as possible, use is made of liquid-crystal media having a large absolute value of the dielectric anisotropy which generally predominantly and in most cases even essentially consist of liquid-crystal compounds having a dielectric anisotropy having the corresponding sign, i.e. of compounds of positive dielectric anisotropy in the case of dielectrically positive media and of compounds of negative dielectric anisotropy in the case of dielectrically negative media. In the respective types of media (dielectrically positive or dielectrically negative), at most significant amounts of dielectrically neutral liquid-crystal compounds are typically employed. Liquid-crystal compounds having the opposite sign of the dielectric anisotropy to that of the dielectric anisotropy of the medium are generally employed extremely sparingly or not at all.

An exception is formed here by liquid-crystalline media for MIM ("metal-insulator-metal") displays (Simmons, J. G., Phys. Rev. 155 No. 3, pp. 657-660 and Niwa, J. G. et al., SID 84 Digest, pp. 304-307, June 1984), in which the liquid-crystal media are addressed by means of an active matrix of thin-film transistors. In this type of addressing, which utilises the non-linear characteristic line of diode switching, a storage capacitor cannot be charged together with the electrodes of the liquid-crystal display elements (pixels), in contrast to TFT displays. In order to reduce the effect of the drop in voltage during the addressing cycle, the largest possible base value of the dielectric constant is thus necessary. In the case of dielectrically positive media, as employed, for example, in MIM-TN displays, the dielectric constant perpendicular to the molecular axis ($\epsilon_\perp$) must thus be as large as possible since it determines the basic capacitance of the pixel. To this end, as described, for example, in WO 93/01253, EP 0 663 502 and DE 195 21 483, compounds of negative dielectric anisotropy are simultaneously also employed besides dielectrically positive compounds in the dielectrically positive liquid-crystal media.

A further exception is formed by STN displays, in which, for example, dielectrically positive liquid-crystal media comprising dielectrically negative liquid-crystal compounds in accordance with DE 41 00 287 are employed in order to increase the steepness of the electro-optical characteristic line.

The pixels of the liquid-crystal displays can be addressed directly, time-sequentially, i.e. in time multiplex mode, or by means of a matrix of active elements having nonlinear electrical characteristic lines.

The commonest AMDs to date use discrete active electronic switching elements, such as, for example, three-pole switching elements, such as MOS ("metal oxide silicon") transistors or thin film transistors (TFTs) or varistors, or 2-pole switching elements, such as, for example, MIM ("metal-insulator-metal") diodes, ring diodes or "back-to-back" diodes. Various semiconductor materials, predominantly silicon, but also cadmium selenide, are used in the TFTs. In particular, amorphous silicon or polycrystalline silicon is used.

In accordance with the present application, preference is given to liquid-crystal media of positive dielectric anisotropy ($\Delta\epsilon>0$).

1,2,3,4,4a,9,10,10a-octahydrophenanthrenes for use in liquid-crystal mixtures are known from EP 1 162 185 B1. The invention was based on the object of providing novel components for liquid-crystal mixtures in order to meet the various requirements of display manufacturers. In particular, liquid-crystal mixtures which, owing to a high dielectric anisotropy, facilitate the production of liquid-crystal displays having particularly low switching voltage are required. It can thus be seen that there is both a demand for further mesogenic compounds and also, in particular, a demand for liquid-crystal media of positive dielectric anisotropy, a large value of the dielectric anisotropy, a value of the optical anisotropy ($\Delta n$) corresponding to the particular application, a broad nematic phase, good stability to UV, heat and electric voltage, and low rotational viscosity.

This is achieved through the use of the mesogenic compounds of the formula I according to the invention

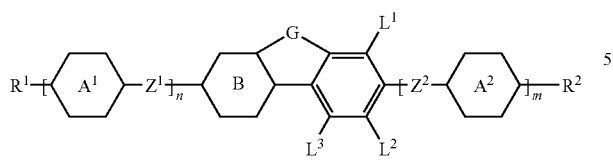

in which

G denotes —CO—O—, —CH$_2$—O—, —CF$_2$—O—, —O—CO—, —CH$_2$—O— or —O—CF$_2$—, preferably CH$_2$O,

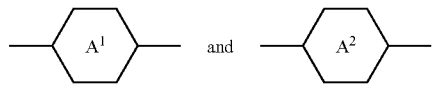

each, independently of one another and, if present more than once, also these independently of one another, denote (a) a trans-1,4-cyclohexylene radical, in which, in addition, one or two non-adjacent CH$_2$ groups may be replaced by —O— and/or (b) a 1,4-cyclohexenylene radical, (c) a 1,4-phenylene radical, in which, in addition, one or two non-adjacent CH groups may be replaced by N, or (d) naphthalene-2,6-diyl, decahydronaphthalene-2,6-diyl and 1,2,3,4-tetrahydronaphthalene-2,6-diyl, (e) a radical selected from the group 1,4-bicyclo[2.2.2]octylene, 1,3-bicyclo[1.1.1]pentylene, spiro[3.3]heptane-2,6-diyl and 1,3-cyclobutylene, where in (a) and (b), one or more —CH$_2$— groups, independently of one another, may each be replaced by a —CHF— or —CF$_2$— group, and in (c) and (d), one or more —CH= groups, independently of one another, may each be replaced by a —CF=, —C(CN)=, —C(CH$_3$)=, —C(CH$_2$F)=, —C(CHF$_2$)=, —C(O—CH$_3$)=, —C(O—CHF$_2$)= or —C(O—CF$_3$)= group, preferably a —CF= group, and preferably denote

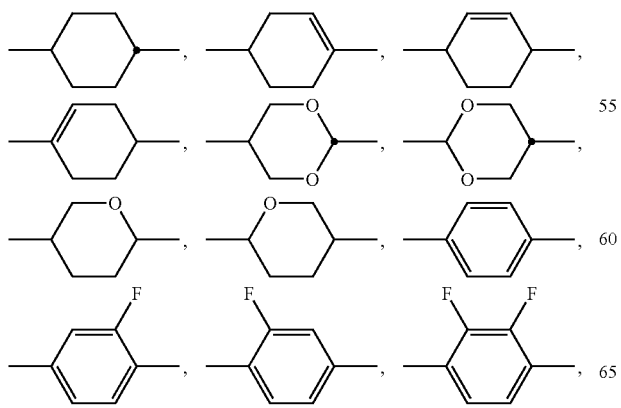

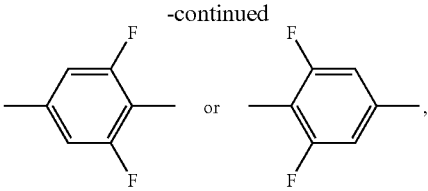

L$^1$ to L$^3$ each, independently of one another, denote H, halogen, CN or CF$_3$, preferably H, F or Cl, particularly preferably H or F, and very particularly preferably L$^1$ and/or L$^2$ denote F and L$^3$ denotes H,

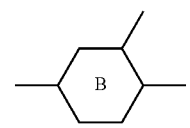

denotes a 1,4-trans-cyclohexane-1,2,4-triyl radical, in which, in addition, one or two non-adjacent CH$_2$ groups may be replaced by —O— and/or —S—, and one or more —CH$_2$— groups, in each case independently of one another, may each be replaced by a —CHF— or —CF$_2$— group, and the —CH< group may be replaced by a —CF< group, and which may optionally contain one, two or three C—C double bonds, where, in this case, one or more —CH= groups, independently of one another, may each be replaced by a —CF=, —C(CN)=, —C(CH$_3$)=, —C(CH$_2$F)=, —C(CHF$_2$)=, —C(O—CH$_3$)=, —C(O—CHF$_2$)= or —C(O—CF$_3$)= group, preferably a —CF= group, R$^1$ and R$^2$ each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —SF$_5$, —CF$_3$, —CHF$_2$, —CH$_2$F, —OCF$_3$, —OCHF$_2$, an alkyl group having 1 to 15 C atoms which is monosubstituted by —CN or —CF$_3$ or at least mono-substituted by halogen, where, in addition, one or more CH$_2$ groups, in each case independently of one another, may be replaced by —O—, —S—, —CH=CH—, —CF=CF—, —CF=CH—, —CH=CF—,

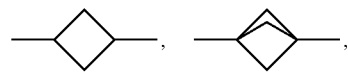

—CO—, —CO—O—, —O—CO— or —O—CO—O— in such a way that neither O nor S atoms are linked directly to one another, preferably one of R$^1$ and R$^2$ denotes alkyl or alkoxy having 1 to 12 C atoms, alkoxyalkyl, alkenyl or alkenyloxy having 2 to 12 C atoms and the other, independently of the first, denotes halogen, —CN, —SCN, —NCS, —OCN, —SF$_5$, —CF$_3$, —CHF$_2$, —CH$_2$F, —OCF$_3$, —OCHF$_2$, Z$^1$ and Z$^2$ each, independently of one another and, if present more than once, also these independently of one another, denote —CH$_2$—CH$_2$—, —(CH$_2$)$_4$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —CO—O—, —O—CO—, —CH$_2$—O—, —O—CH$_2$—, —CF$_2$—O—, —O—CF$_2$—, or a combination of two of these groups, where no two O atoms are bonded to one another, preferably —(CH$_2$)$_4$—, —CH$_2$—CH$_2$—, —CF$_2$—CF$_2$—, —CH═CH—, —CF═CF—, —C≡C—, —CH$_2$—O—, —CF$_2$—O— or a single bond, particularly preferably —CH$_2$—O—, —CH$_2$—CH$_2$—, —CF$_2$—CF$_2$—, —CF═CF—, —CF$_2$—O— or a single bond, and n and m each denote 0, 1 or 2, where
n+m denotes 0, 1, 2 or 3, preferably 0, 1 or 2, particularly preferably 0 or 1.

Particular preference is given to liquid-crystal compounds of the formula I of positive dielectric anisotropy.

Preference is furthermore given to compounds of the formula I in which the structural element

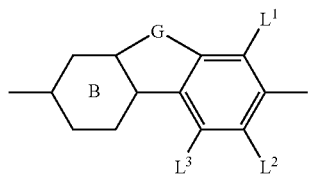

denotes

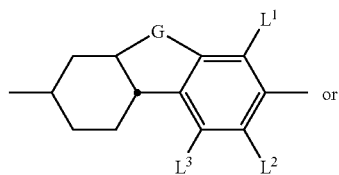

(a)

or

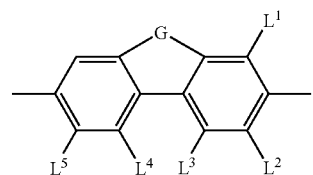

(b)

in which the parameters have the meaning given above under formula I, and
L$^4$ and L$^5$ each, independently of one another, denote H or F, and preferably
in (a) one of
L$^1$ and L$^2$ denotes F or both denote F,
in (b) one or more, preferably two or three, of
L$^1$, L$^2$ and L$^4$ denote F.

Preference is furthermore given to the compounds of the formula I which contain the structural element (a).

Very particular preference is given to liquid-crystal compounds of the formula I of the sub-formulae I-A and I-B, particularly I-A,

I-A

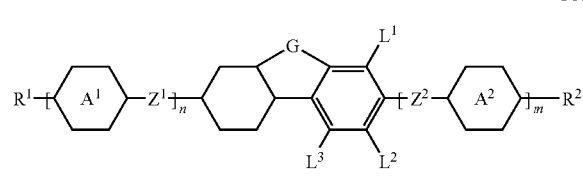

I-B

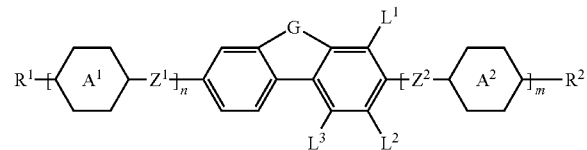

in which the parameters have the meaning given above under formula I, and the second aromatic ring in formula I-B may optionally be mono- or polysubstituted by F, and preferably one or both of
L$^1$ and L$^2$ denotes F.

Very particular preference is given to liquid-crystal compounds of the formula I of the sub-formulae I-A1 to I-A3 and I-B1 to I-B3, particularly of the formulae I-A1 to I-A3,

I-A1

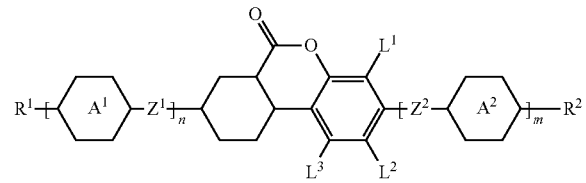

I-A2

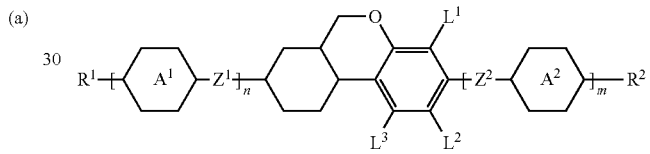

I-A3

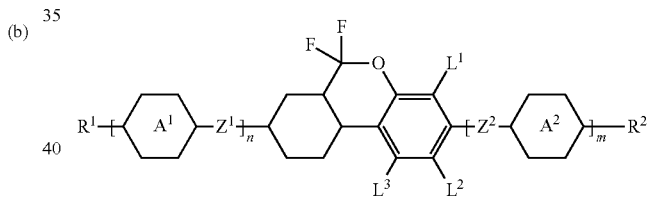

I-B1

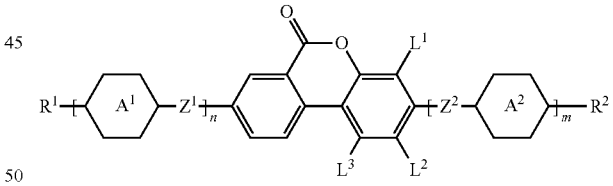

I-B2

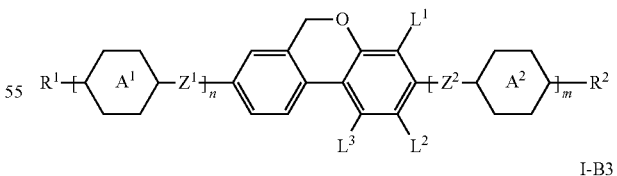

I-B3

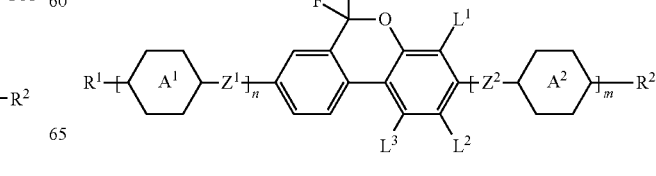

in which the parameters have the meaning given above under formula I, and the second aromatic ring in the formulae I-B1 to I-B3 may optionally be mono- or polysubstituted by F, and preferably one or both of L$^1$ and L$^2$ denotes F.

Preference is given to compounds of the formula I, preferably selected from the group of the compounds of the formulae I-A1 to I-A3 and I-B1 to I-B3, in which the sum n+m is 0 or 1, preferably 1.

A preferred embodiment is represented by the compounds of the formula I in which the sum n+m is 1 and preferably m or n denotes 1,

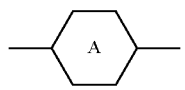

denotes

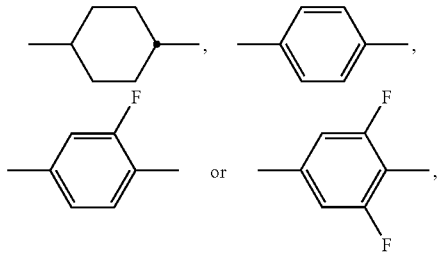

Z preferably denotes —(CH$_2$)$_4$—, —CH$_2$—CH$_2$—, —CF$_2$—CF$_2$—, —CH=CH—, —CF=CF—, —C≡C—, —CH$_2$—O—, —CF$_2$—O— or a single bond, particularly preferably —CH$_2$—O—, —CH$_2$—CH$_2$—, —CF$_2$—CF$_2$—, —CF=CF—, —CF$_2$—O— or a single bond, and L, R$^1$ and R$^2$ have the meaning given above for formula I, and L preferably denotes F.

Particular preference is given to compounds of the formula I, preferably selected from the group of the compounds of the formulae I-A1 to I-A3 and I-B1 to I-B3, in which n and m both denote 0, and L$^1$ to L$^3$, R$^1$ and R$^2$ have the meaning given above for the corresponding formula and L$^1$ and/or L$^2$ preferably denote F.

Compounds of the formula I containing branched wing groups R$^1$ and/or R$^2$ may occasionally be of importance owing to better solubility in the usual liquid-crystalline base materials, but in particular as chiral dopants if they are optically active. Smectic compounds of this type are suitable as components of ferroelectric materials. Compounds of the formula I having SA phases are suitable, for example, for thermally addressed displays.

If R$^1$ and/or R$^2$ denote an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl or alkoxyalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R$^1$ and/or R$^2$ denote an alkyl radical in which one CH$_2$ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R$^1$ and/or R$^2$ denote an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. Accordingly, they denote, in particular, acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R$^1$ and/or R$^2$ denote an alkyl radical in which one CH$_2$ group has been replaced by unsubstituted or substituted —CH=CH— and an adjacent CH$_2$ group has been replaced by CO or CO—O or O—CO, this may be straight-chain or branched. It is preferably straight-chain and has 4 to 13 C atoms. Accordingly, it denotes, in particular, acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R$^1$ and/or R$^2$ denote an alkyl or alkenyl radical which is mono-substituted by CN or CF$_3$, this radical is preferably straight-chain. The substitution by CN or CF$_3$ is in any desired position.

If R$^1$ and/or R$^2$ denote an alkyl or alkenyl radical which is at least mono-substituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Branched groups generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

If R$^1$ and/or R$^2$ represent an alkyl radical in which two or more CH$_2$ groups have been replaced by —O— and/or —CO—O—, this may be straight-chain or branched. It is preferably branched and has 3 to 12 C atoms. Accordingly, it denotes, in particular, biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)phenyl.

Particular preference is given to compounds of the formula I in which n=0 or 1 and m=0 and $R^1$ denotes methyl, ethyl, propyl, butyl, pentyl, vinyl, 1E-propenyl, 1E-butenyl or 1E-pentenyl, and to media comprising these compounds. Of these compounds, the alkyl-substituted compounds are particularly preferably employed.

The compounds of the formula I may be in the form of stereoisomers owing to asymmetrically substituted carbon atoms in ring B. The invention relates to all isomers, both in pure form, as a racemate and also as a mixture of diastereomers or enantiomers. Optically active compounds of the formula I can also be used as dopants in liquid-crystal mixtures.

The compounds of the formula I are synthesised (see Schemes Ia to Ic and II to IX) by the processes described in the literature (Houben Weyl, Methoden der organischen Chemie [Methods of Organic Chemistry], Georg Thieme Verlag, Stuttgart, N.Y., 4th Edn. 1993. Regarding Scheme II, see also DE 10 2004 004 228 (A) and Taugerbeck, M. Klasen-Memmer, Application Number 10 2005 031 554.2).

In the following schemes, the compounds of the formula I are abbreviated to compounds 1. Compounds 1b and 1c here are accessible from the lactones 1a. Thus, 1b is obtained either directly by reduction of 1a using sodium borohydride in the presence of boron trifluoride or in two steps, for example by reduction of 1a to the lactol 2 and subsequent treatment with triethylsilane in the presence of boron trifluoride, or by reduction of 1a to the diol 3 and subsequent etherification, for example by treatment with acids or by Mitsunobu reaction with triphenylphosphine and diethyl azodicarboxylate (see Schemes Ia to Ic).

Scheme Ia: Conversion of the lactones 1a to ethers 1b

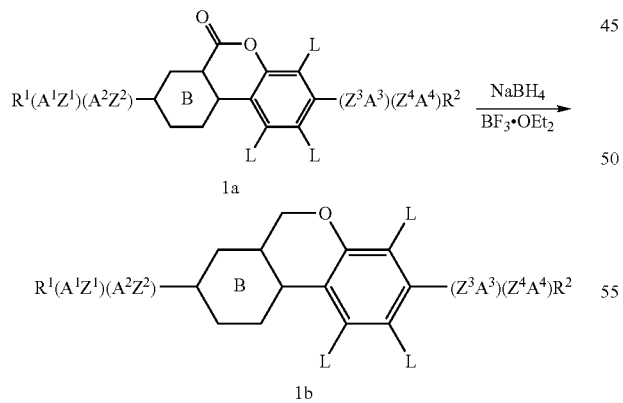

in which, as in the following schemes, unless explicitly indicated otherwise, $R^1$ and $R^2$ each, independently of one another, have the meanings indicated above for $R^1$ and $R^2$ respectively in the case of formula I and the other parameters each have the corresponding meanings indicated above in the case of formula I.

Scheme Ib: Alternative conversion of the lactones 1a to ethers 1b

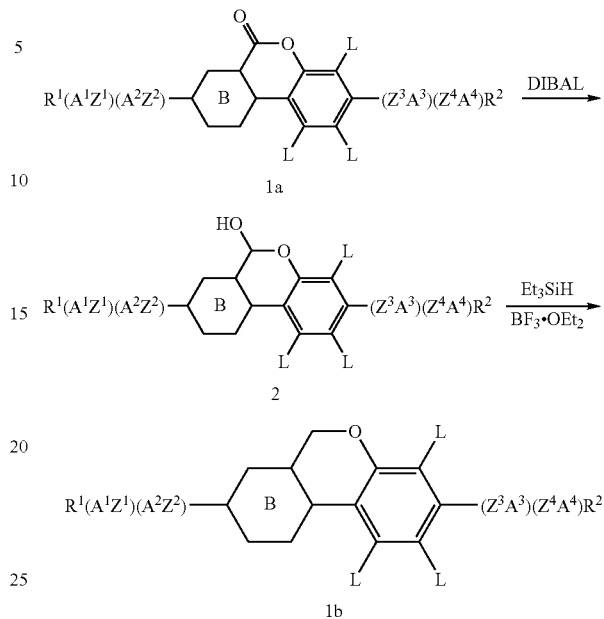

Scheme Ic: Further alternative conversion of the lactones 1a to ethers 1b

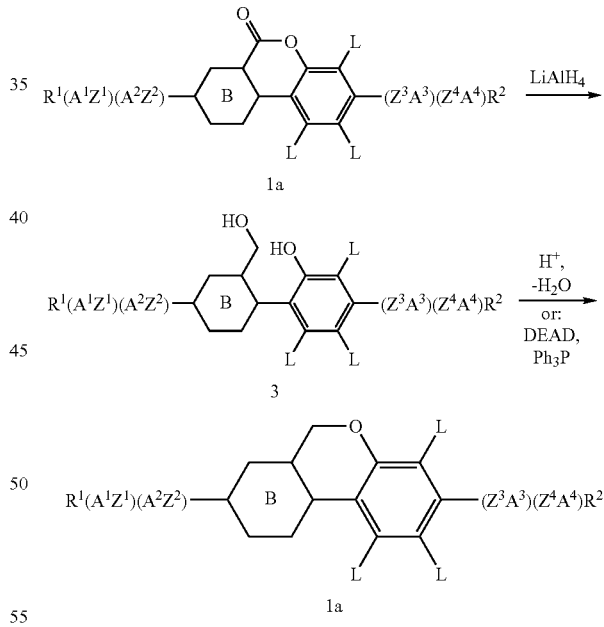

The difluoroether 1c is obtained, for example, either by reaction of the lactones 1a with Lawesson's reagent to give 4 and subsequent treatment with DAST or with NBS in the presence of Ohla's reagent (W. H. Bunnelle, B. R. McKinnis, B. A. Narayanan, J. Org. Chem. 1990, 55, pp. 768-770) (see Scheme II) or analogously to the process described in A. Taugerbeck, M. Klasen-Memmer, Application Number 10 2005 031 554.2 by fluorodesulfuration of dithioorthoesters of type 5 using an oxidant, such as, for example, bromine, NBS, DBH, inter alia, in the presence of a fluoride ion source, such as HF/pyridine complex, triethylamine trishydrogen-fluoride, etc. (see Scheme III).

Scheme II: Conversion of the lactones 1a to difluoroethers 1c

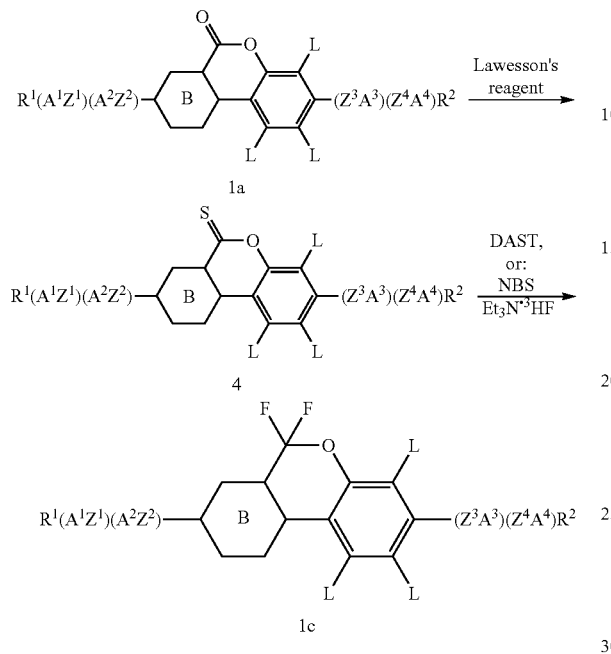

The lactones 1a can be prepared as described by S. Sethna, R. Phadke, *Org. React.* 1953, 7, p. 1 by Pechmann condensation of phenol derivatives or resorcinols with β-ketoesters of type 6 (V. H. Wallingford, A. H. Homeyer, D. M. Jones, *J. Am. Chem. Soc.* 1941, 63, pp. 2252-2254) and subsequent hydrogenation (Scheme IV).

An alternative reduction of the compounds 8 using lithium in ammonia is described in D. J. Collins, A. G. Ghingran, S. B. Rutschmann, *Aust. J. Chem.* 1989, 42, pp. 1769-1784.

Scheme IV: Preparation of the lactones 1a by Pechmann condensation

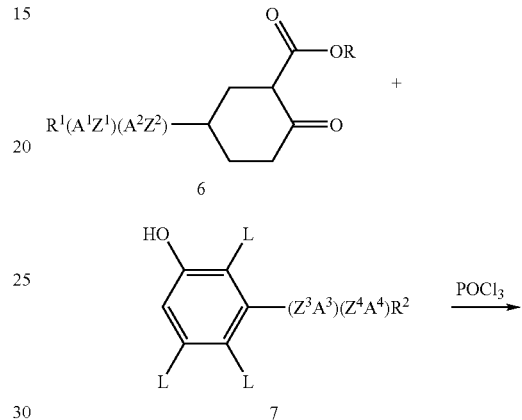

Scheme III: Alternative conversion of the lactones 1a to difluoroethers 1c

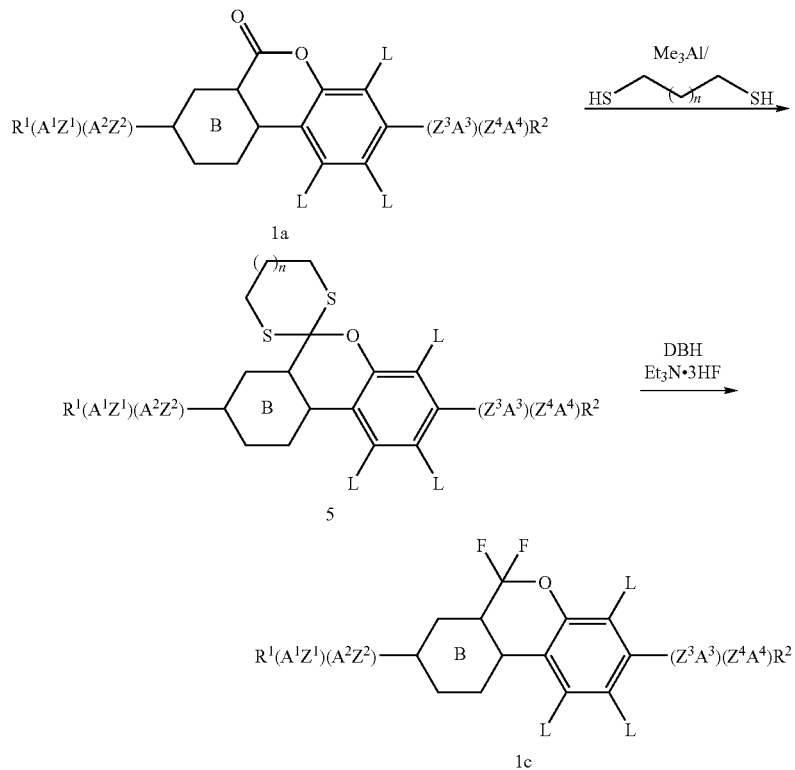

in which n = 0 or 1.

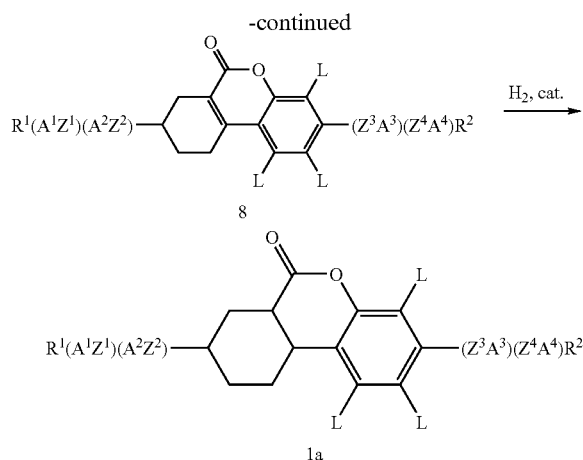

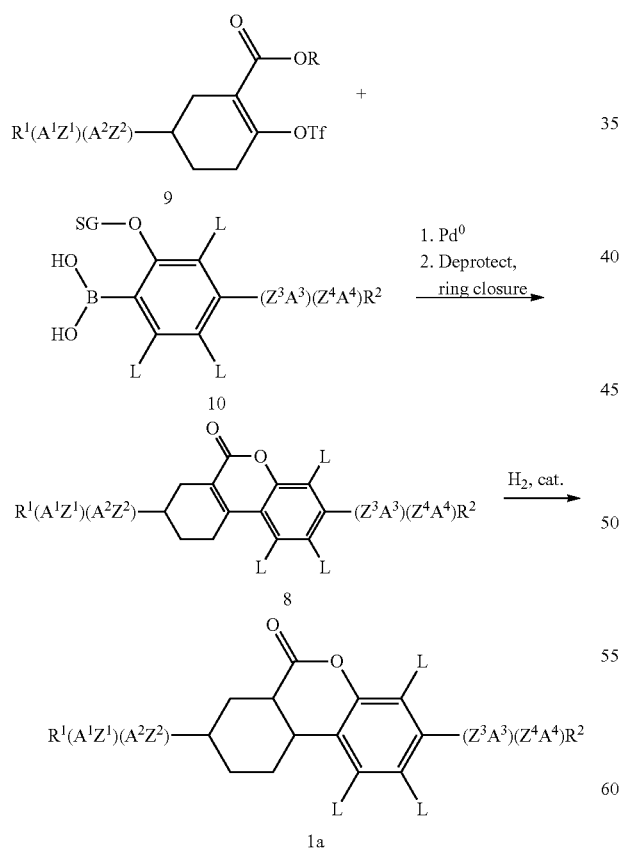

The compounds 1a are obtained after hydrogenation as an isomer mixture, which can be separated by conventional methods, crystallisation and/or chromatography. Compounds having the 6aR*,8R*,10aS* configuration can be obtained as shown in Scheme VI in two additional synthesis steps and by the method of D. J. Collins, A. G. Ghingran, S. B. Rutschmann, *Aust. J. Chem.* 1989, 42, pp. 1769-1784 by base-catalysed isomerisation, where it may be advantageous firstly to open the lactone ring by saponification analogously to J. M. Fevig et al., *Bioorg. Med. Chem. Lett.* 1996, 6, pp. 295-300 and to close it again after base-catalysed isomerisation is complete.

Scheme VI

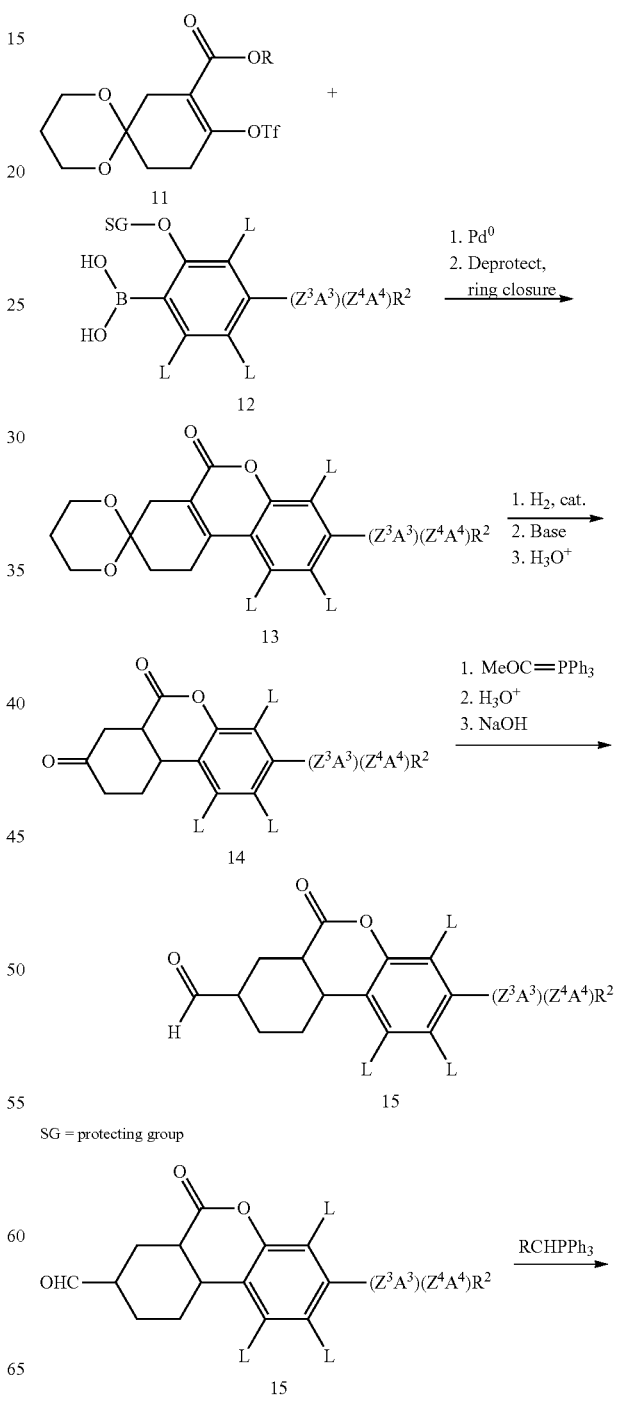

-continued

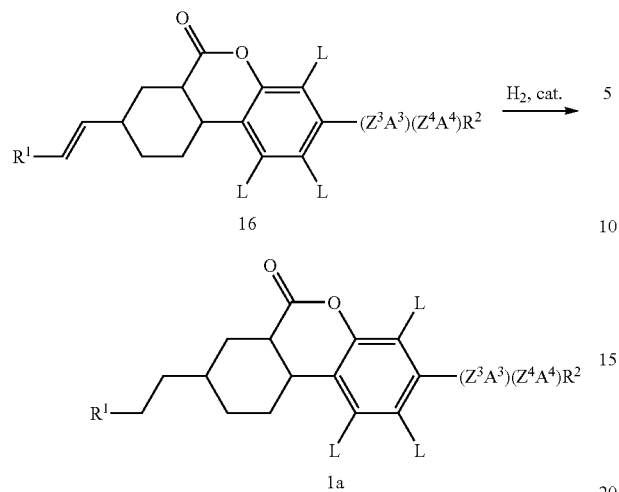

More highly unsaturated or aromatic compounds 1a can be obtained analogously to the synthesis shown in Scheme IV (see Scheme VII). Corresponding access to dielectrically negative compounds is disclosed in A. Taugerbeck, M. Klasen-Memmer, Application Number DE 10 2005 031 554.2.

Scheme VII: Preparation of unsaturated lactones 1a by Suzuki reaction

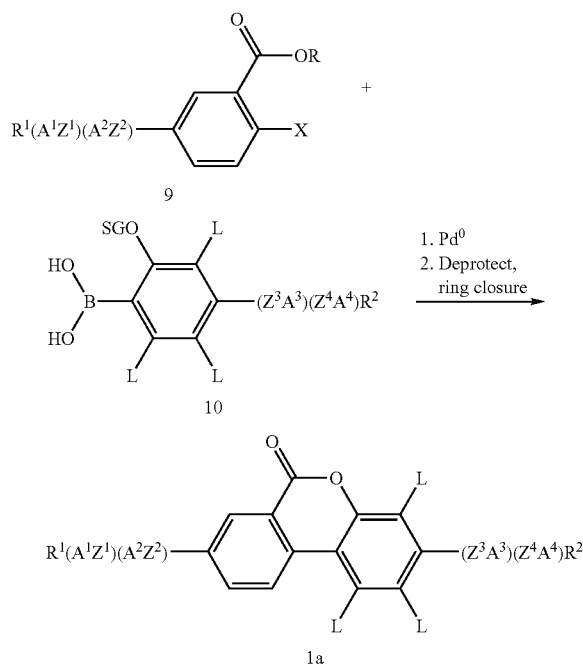

X = OTf, Cl, Br, I

An alternative synthesis strategy is shown in Schemes VIII and IX, where firstly the ether or ester function is formed starting from precursors 9 or 17 substituted in a suitable manner, and the biphenyl system is built up in a second step by, for example, Suzuki coupling (Scheme VIII) or Heck reaction (Scheme IX).

Scheme VIII:

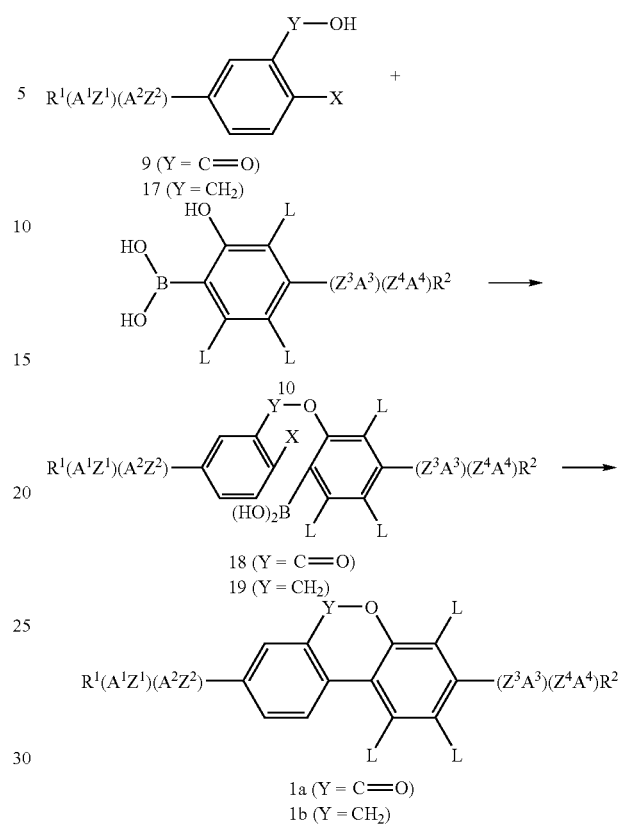

X = OTf, Cl, Br, I

Scheme IX:

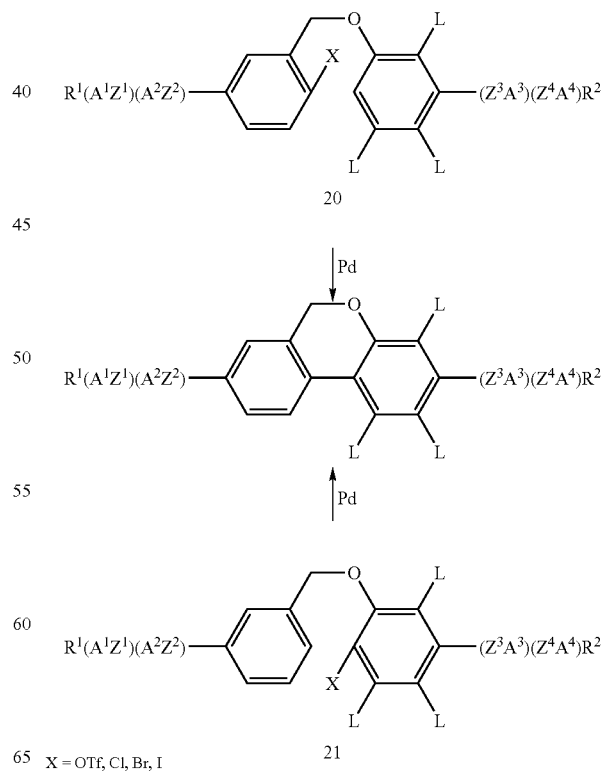

X = OTf, Cl, Br, I

Examples of structures of preferred compounds of the formula I, in which R has the meaning given for R¹ under formula I and preferably denotes alkyl having 1 to 12 C atoms, particularly preferably having 1 to 7 C atoms, or alkenyl having 2 to 7 C atoms and very particularly preferably n-alkyl, including methyl, or 1E-alkenyl, including vinyl, are given below.
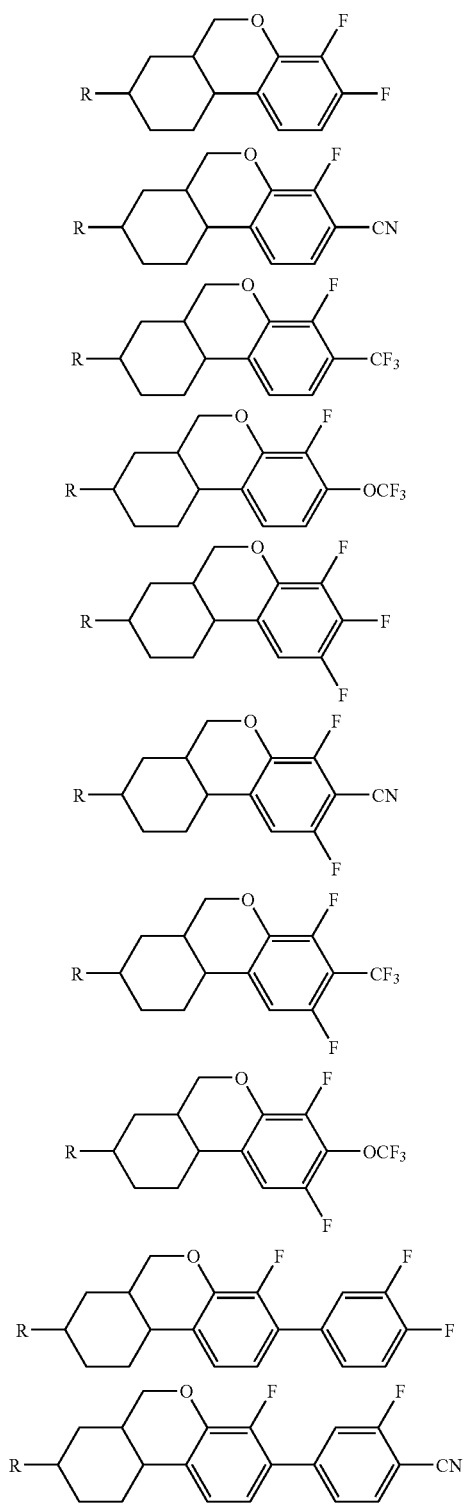
-continued
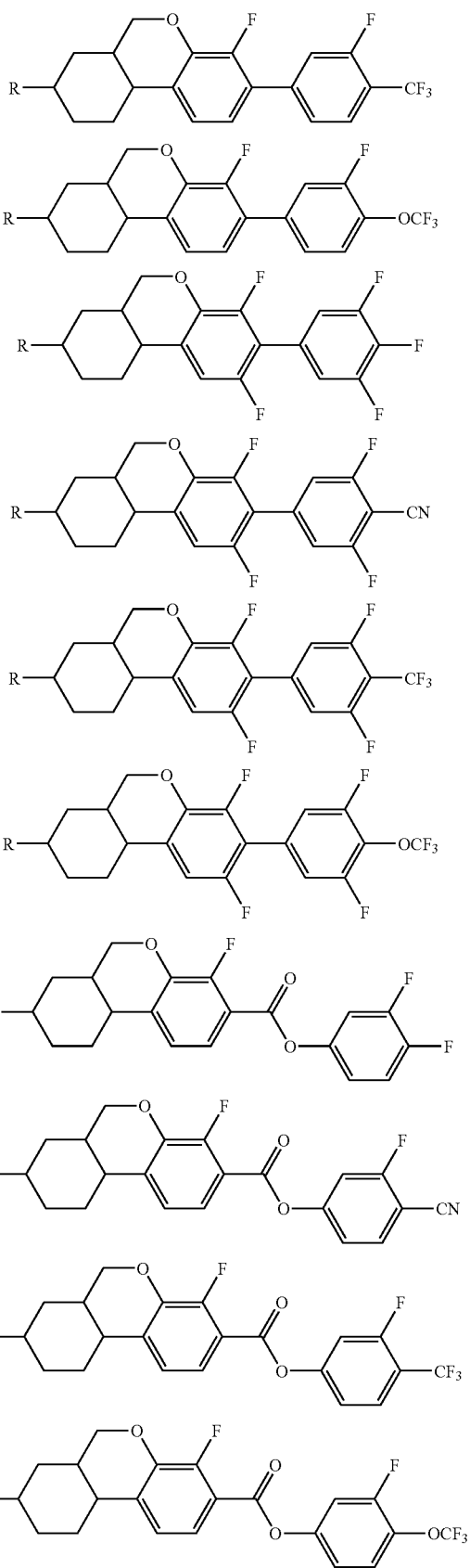

-continued
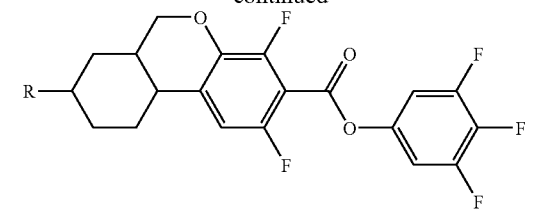
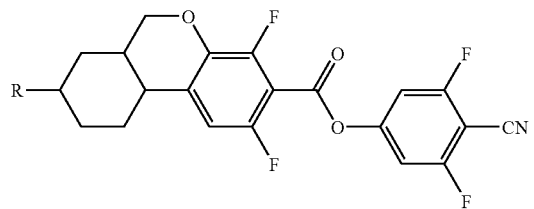
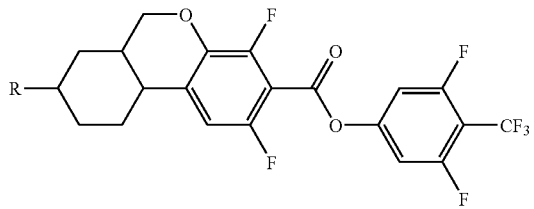
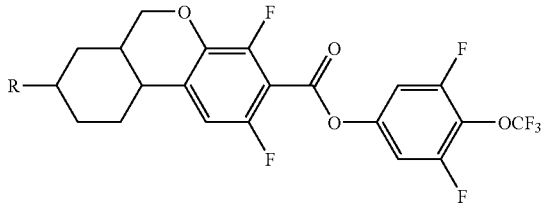
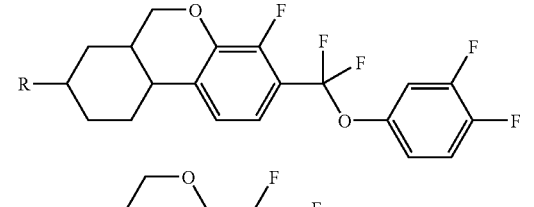
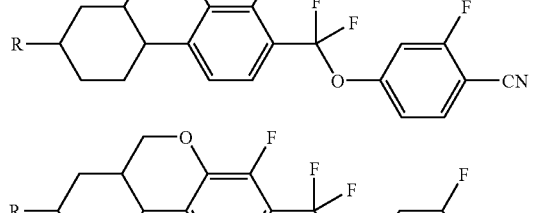
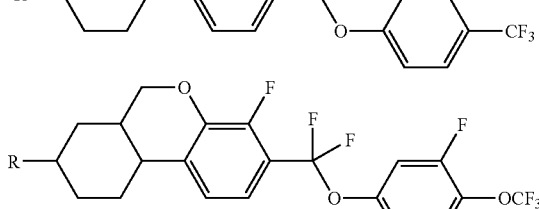
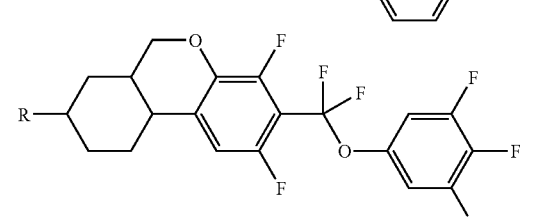
-continued
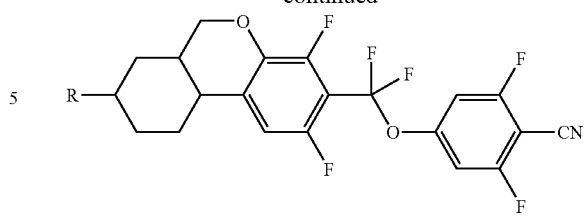
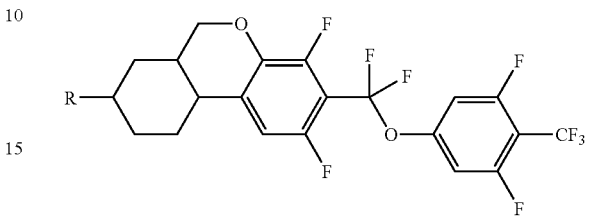
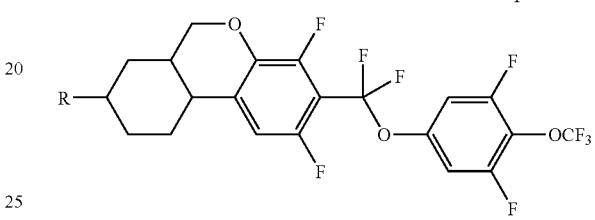
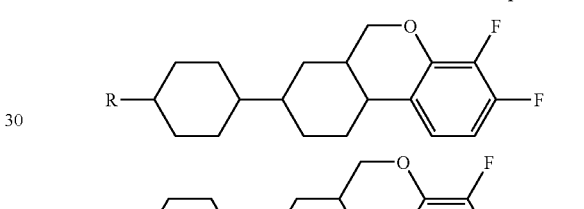
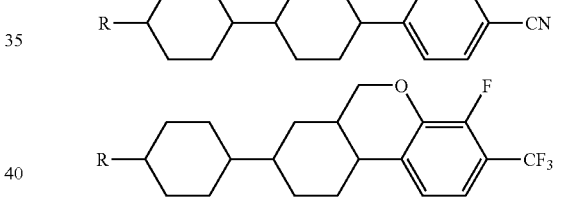
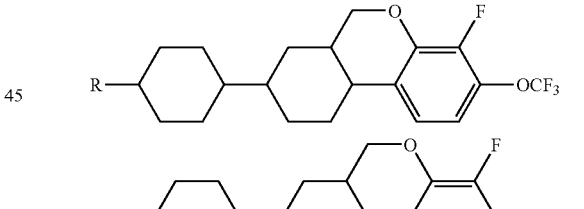
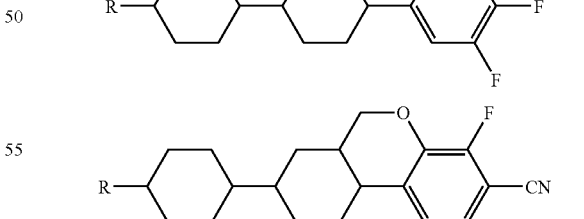
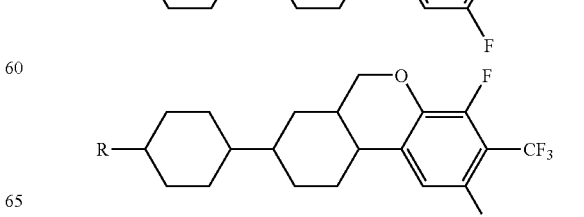

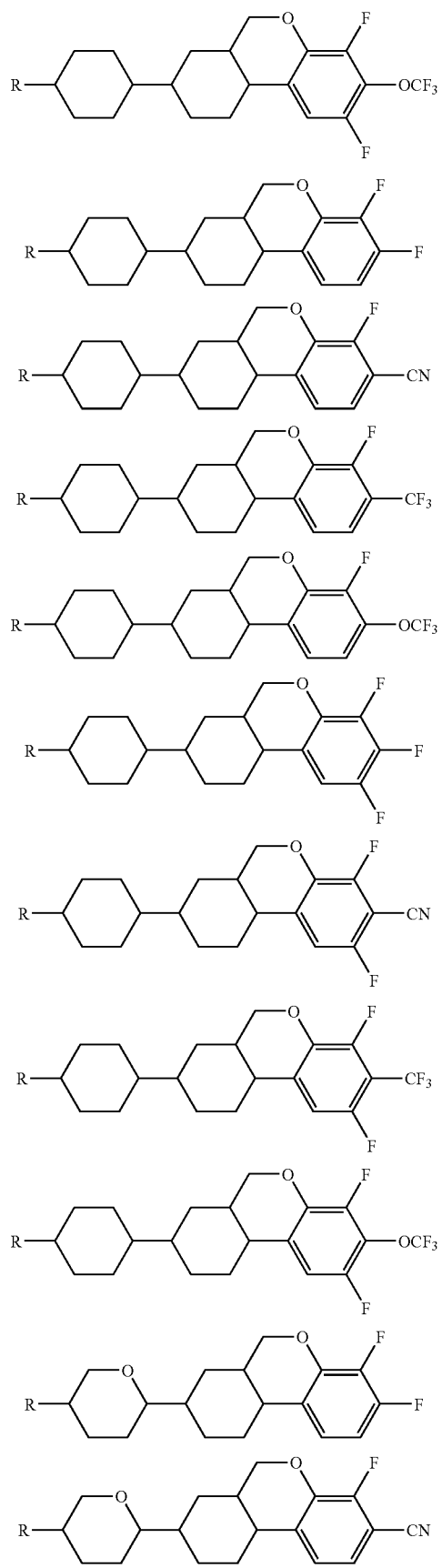
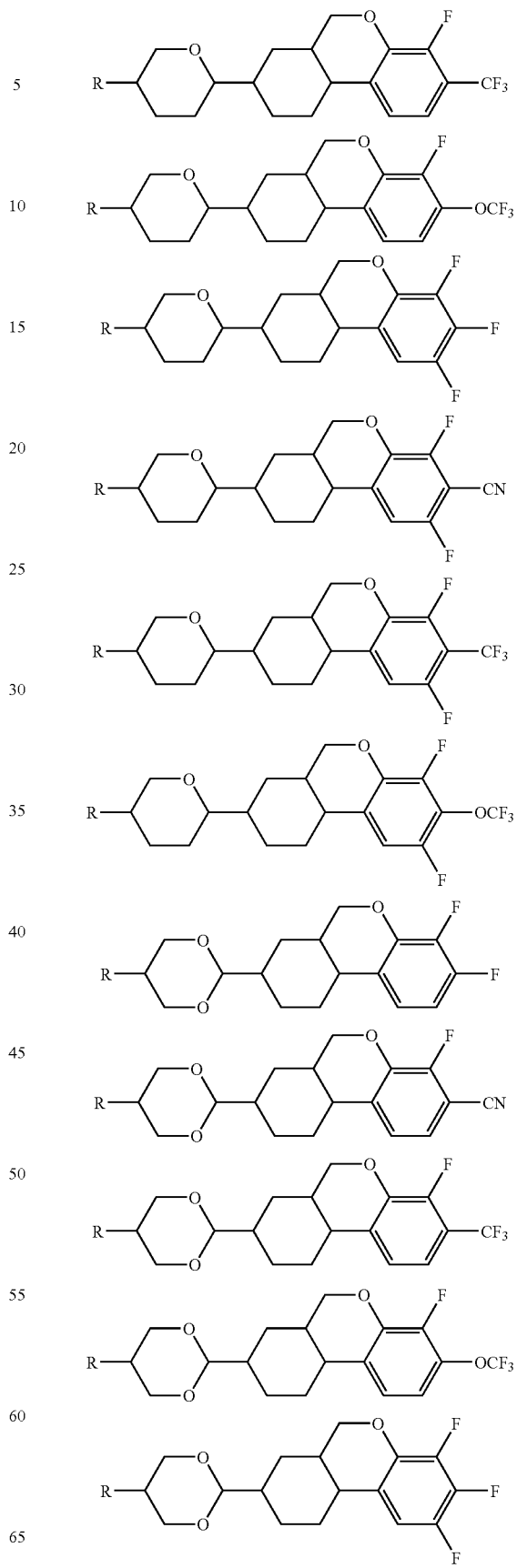

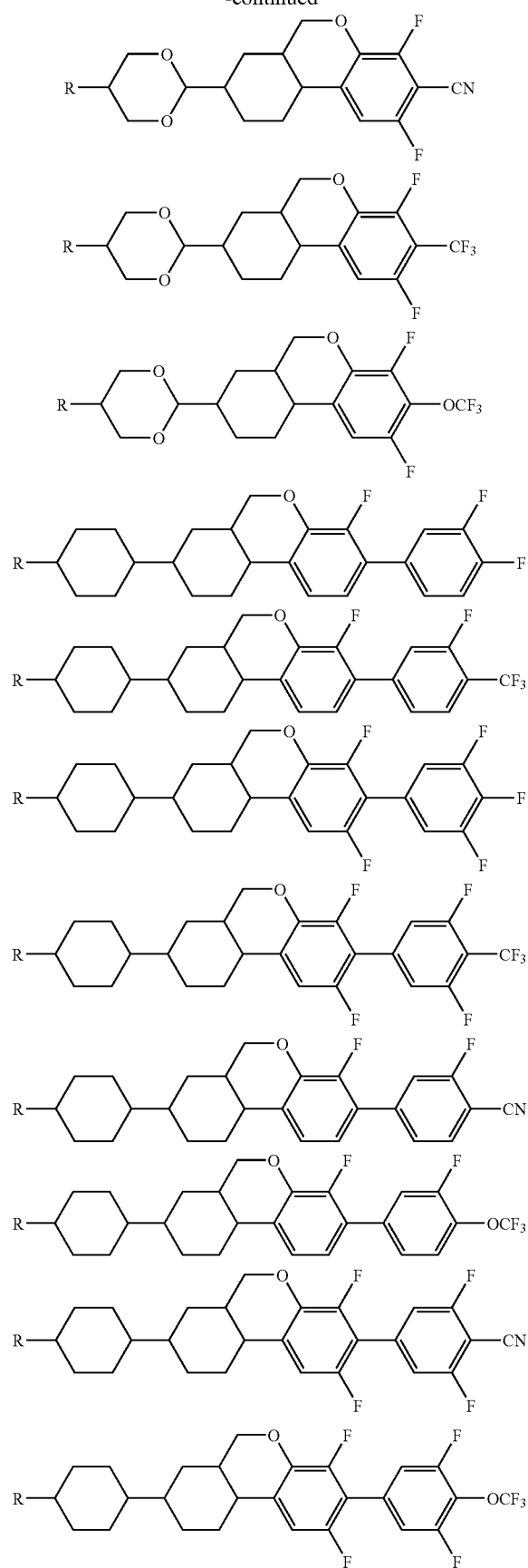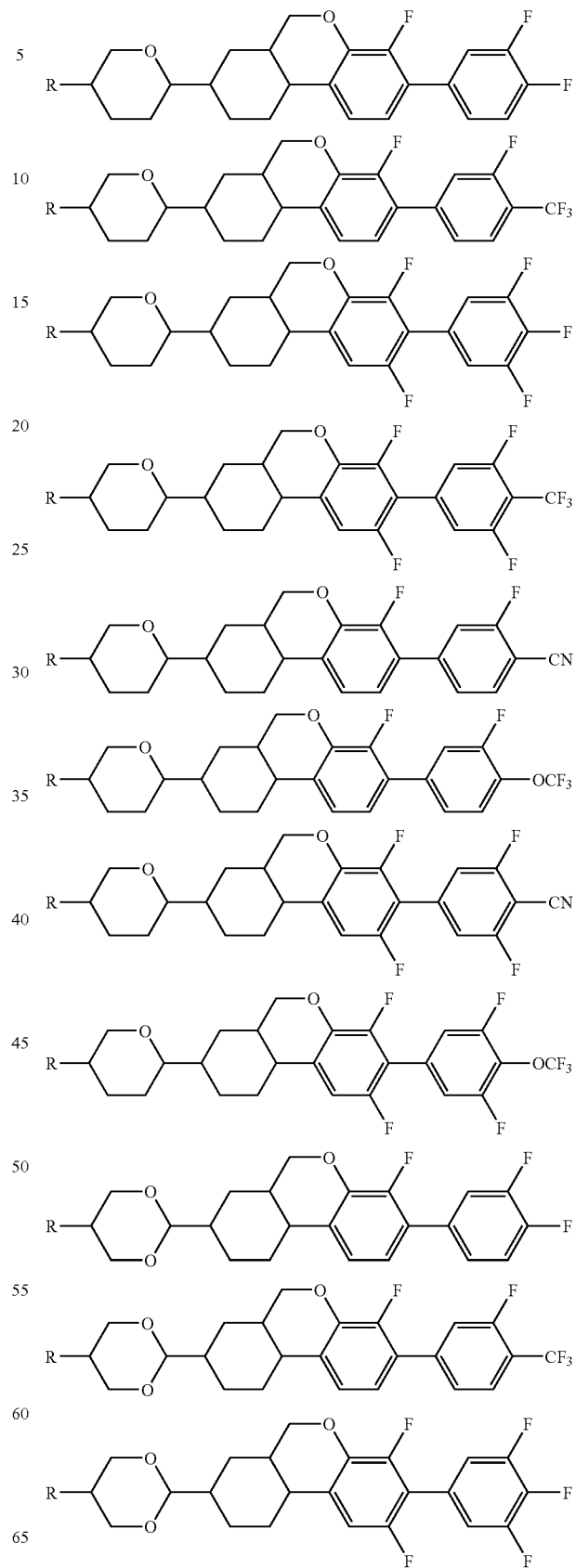

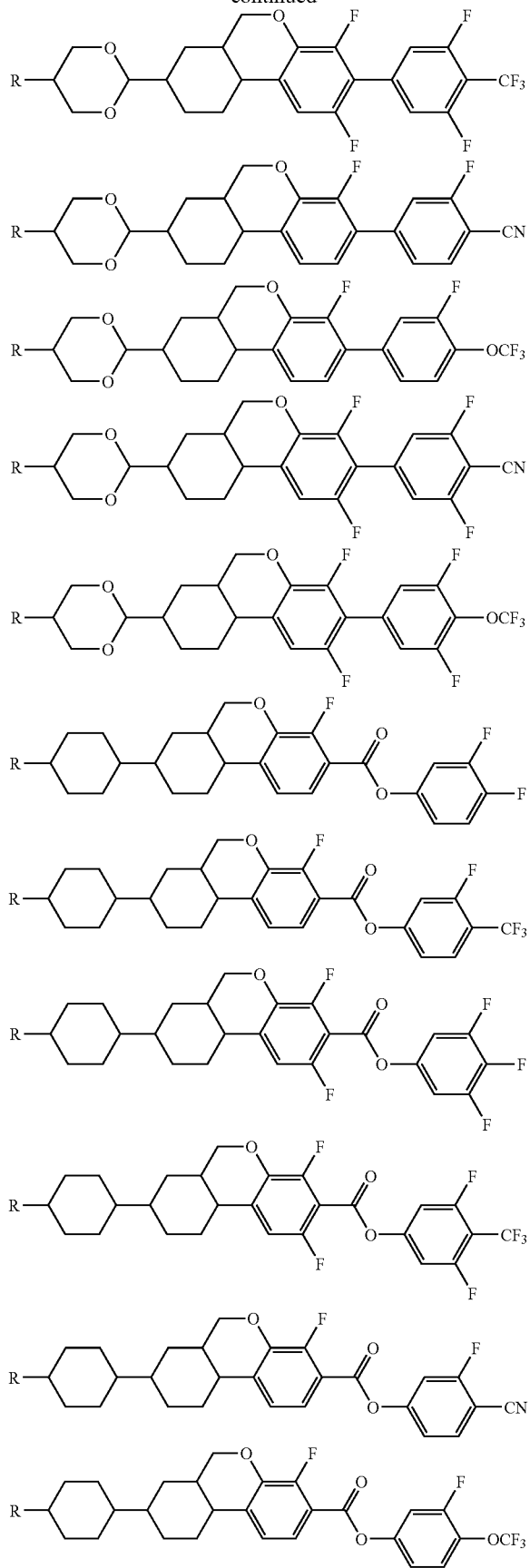
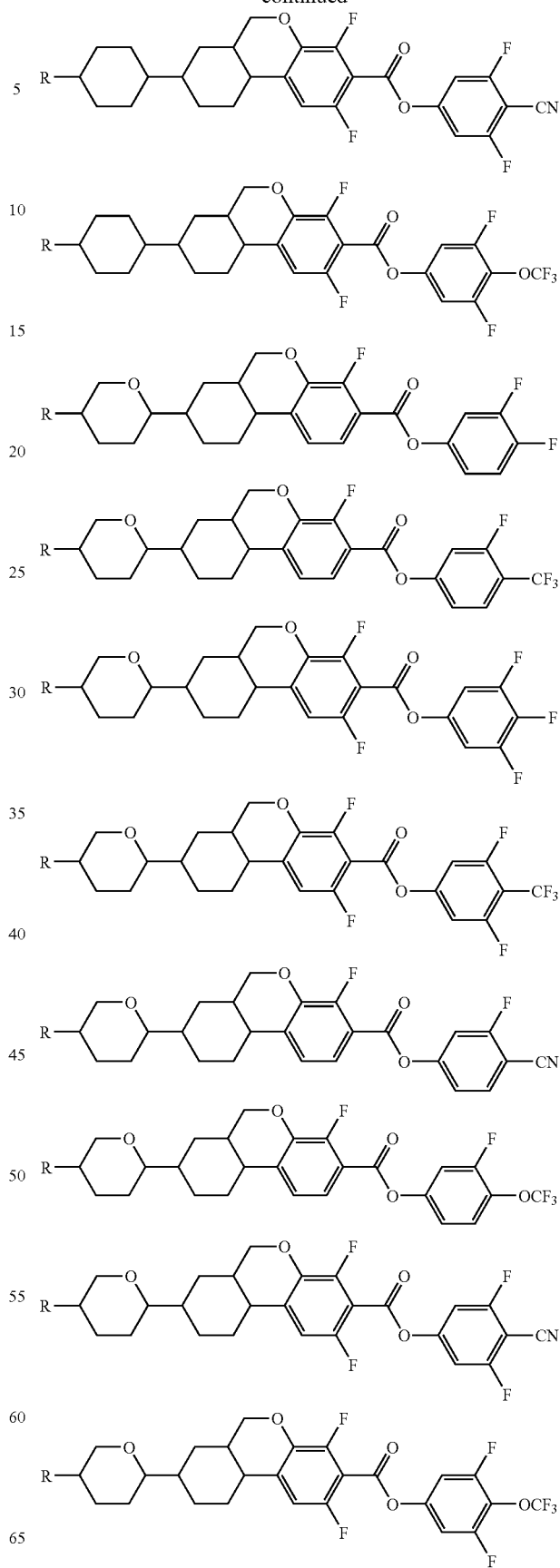

-continued
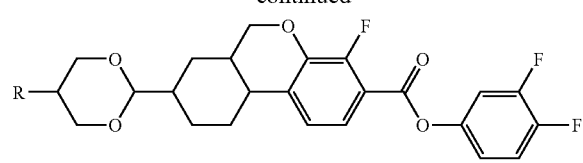
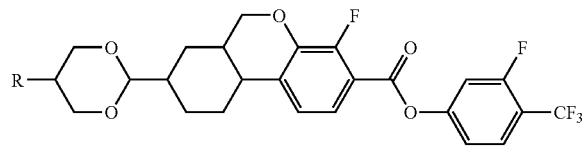
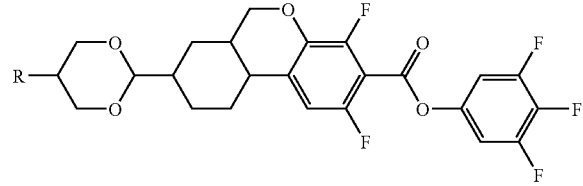
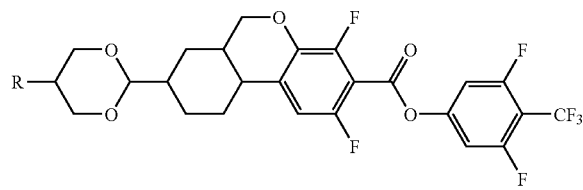
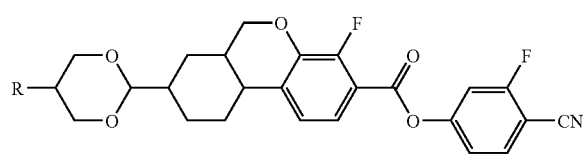
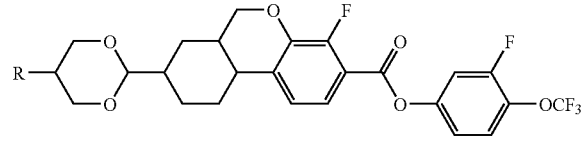
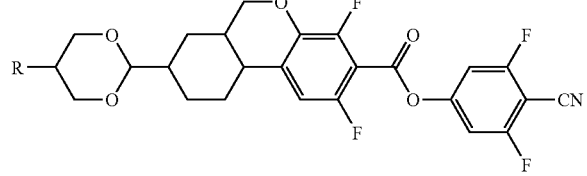
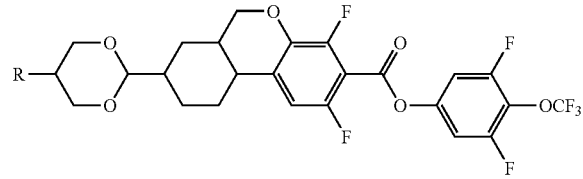
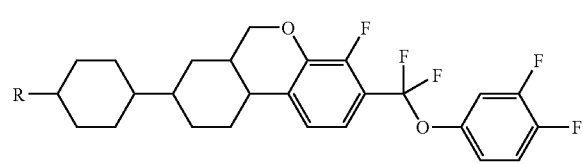
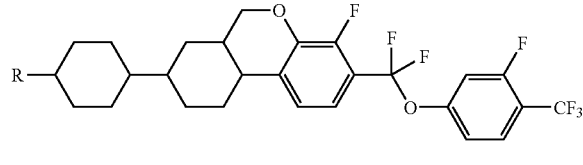
-continued
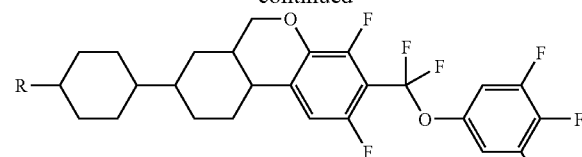
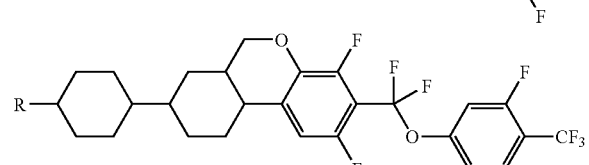
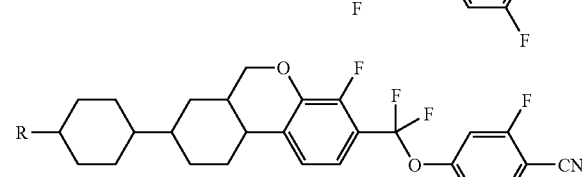
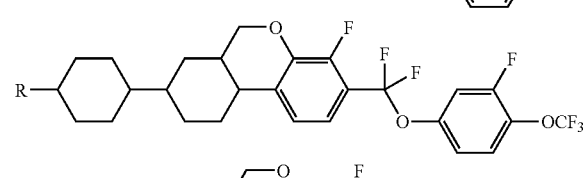
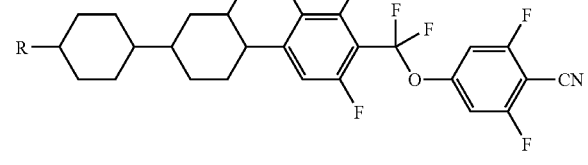
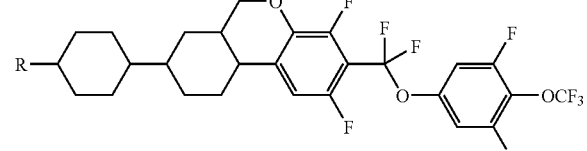
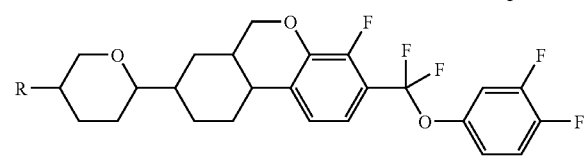
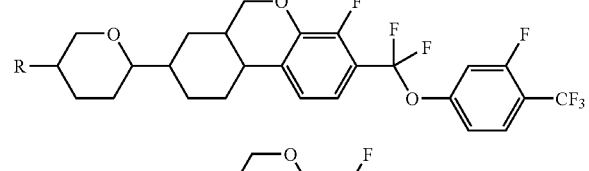
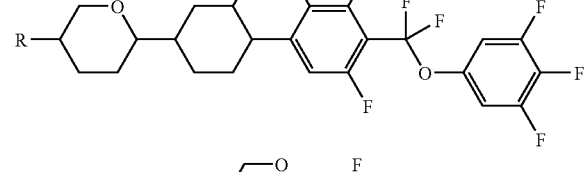
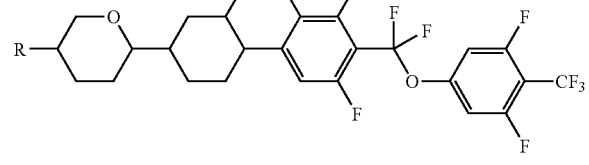

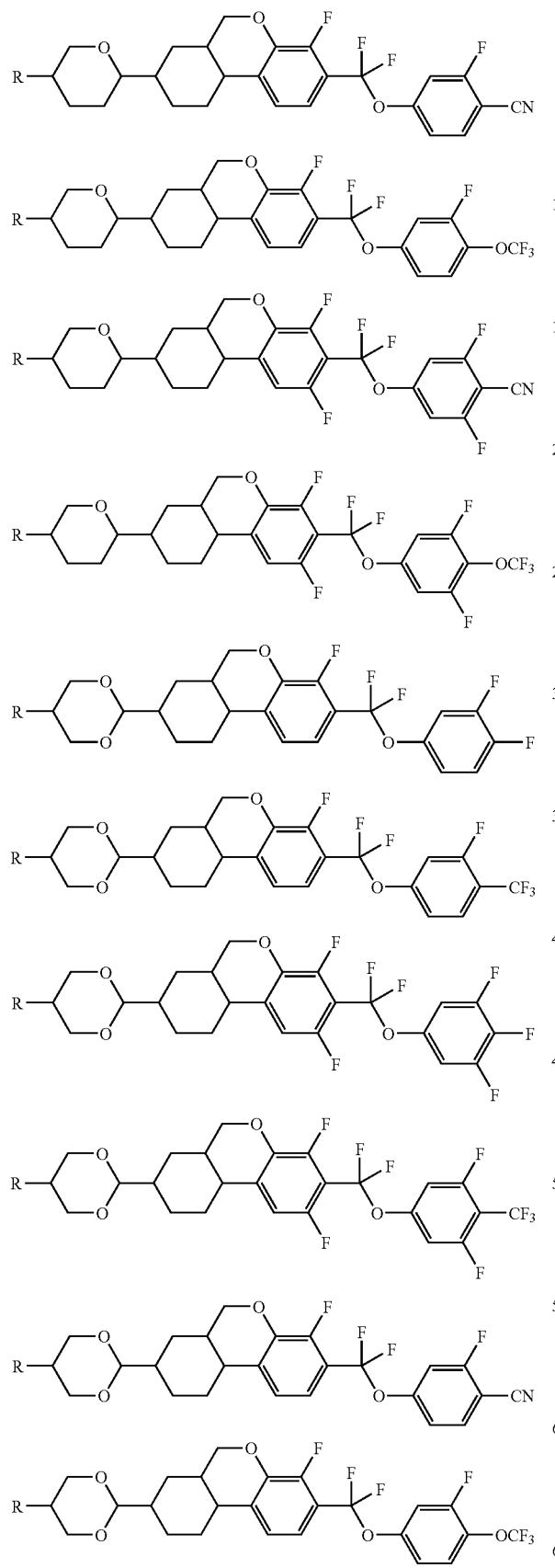
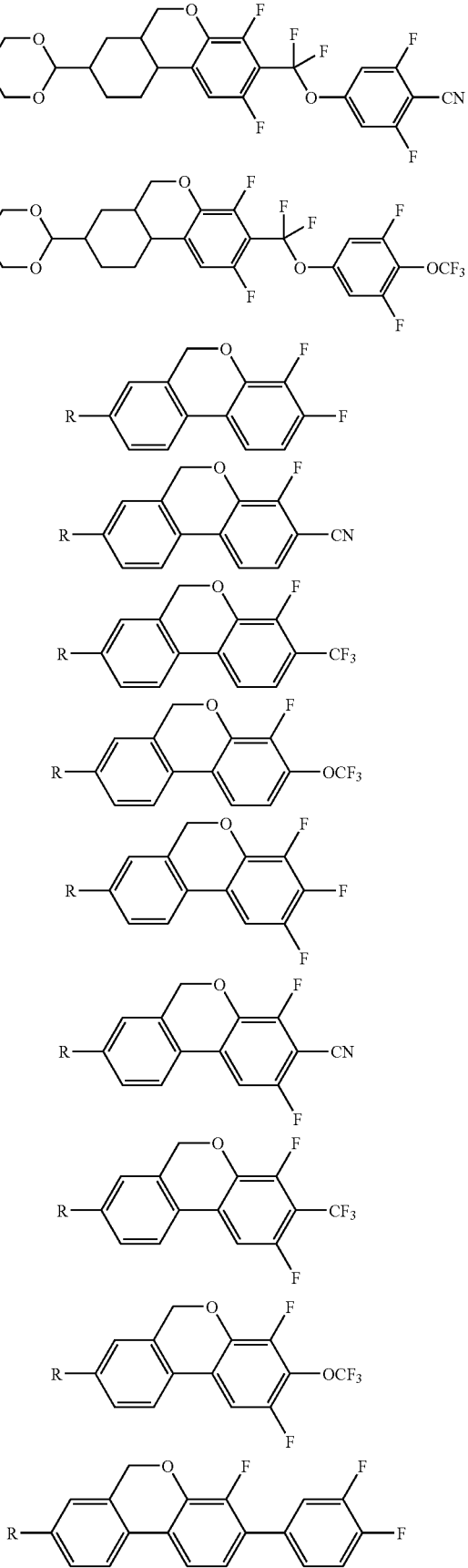

-continued
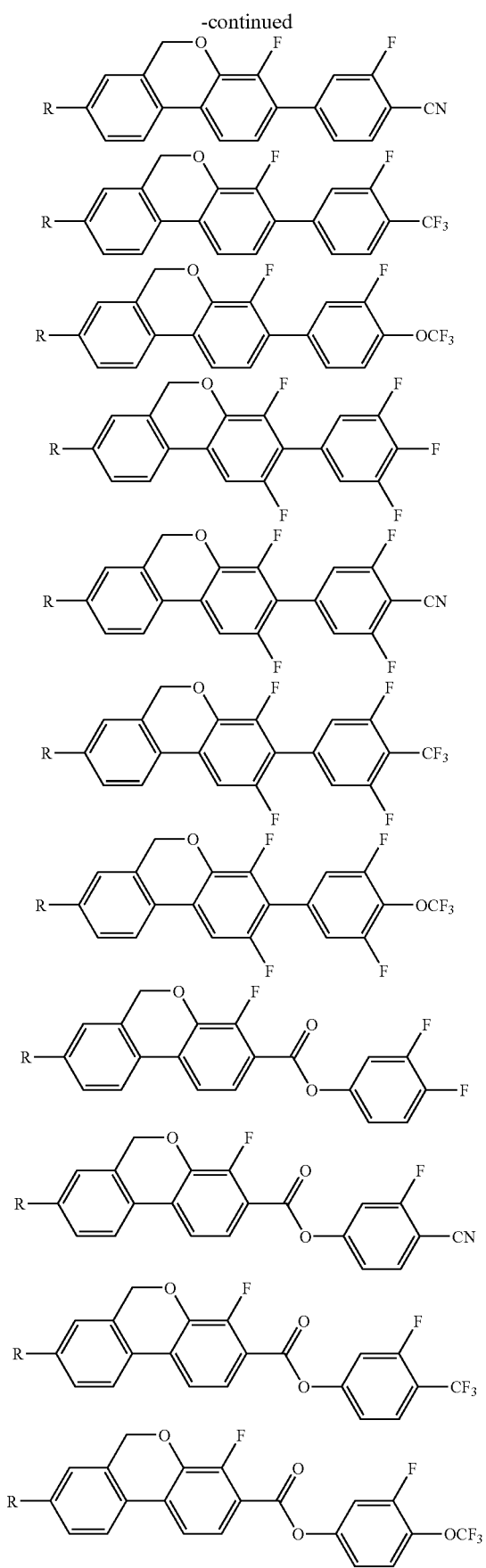
-continued
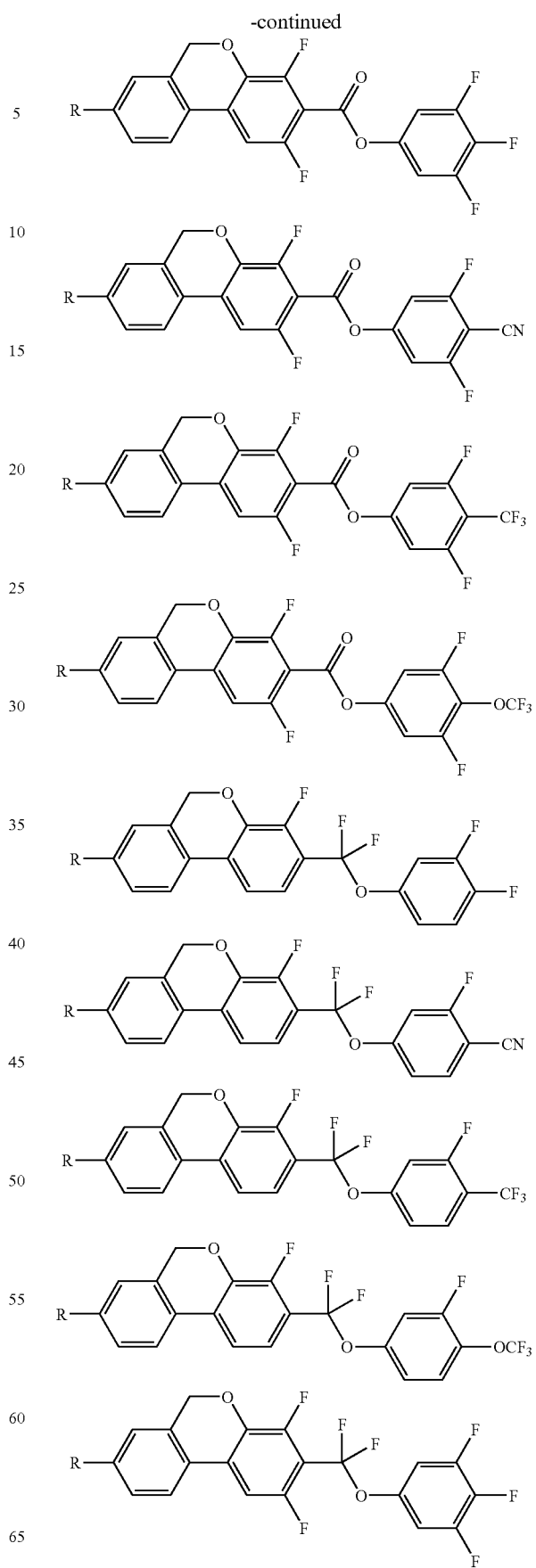

33
-continued
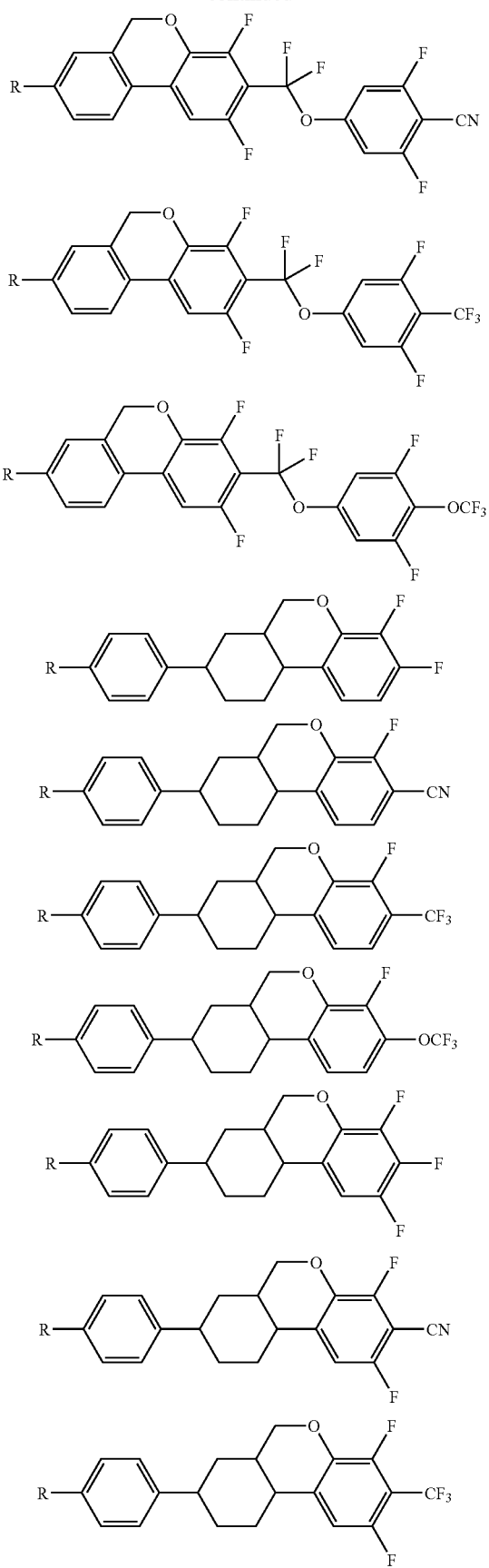
34
-continued
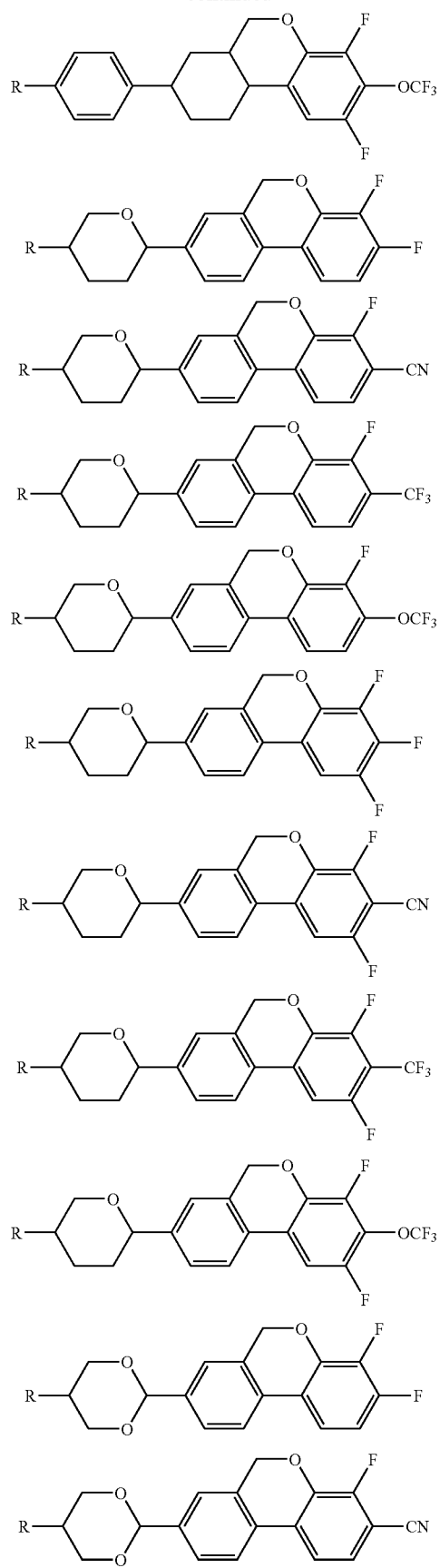

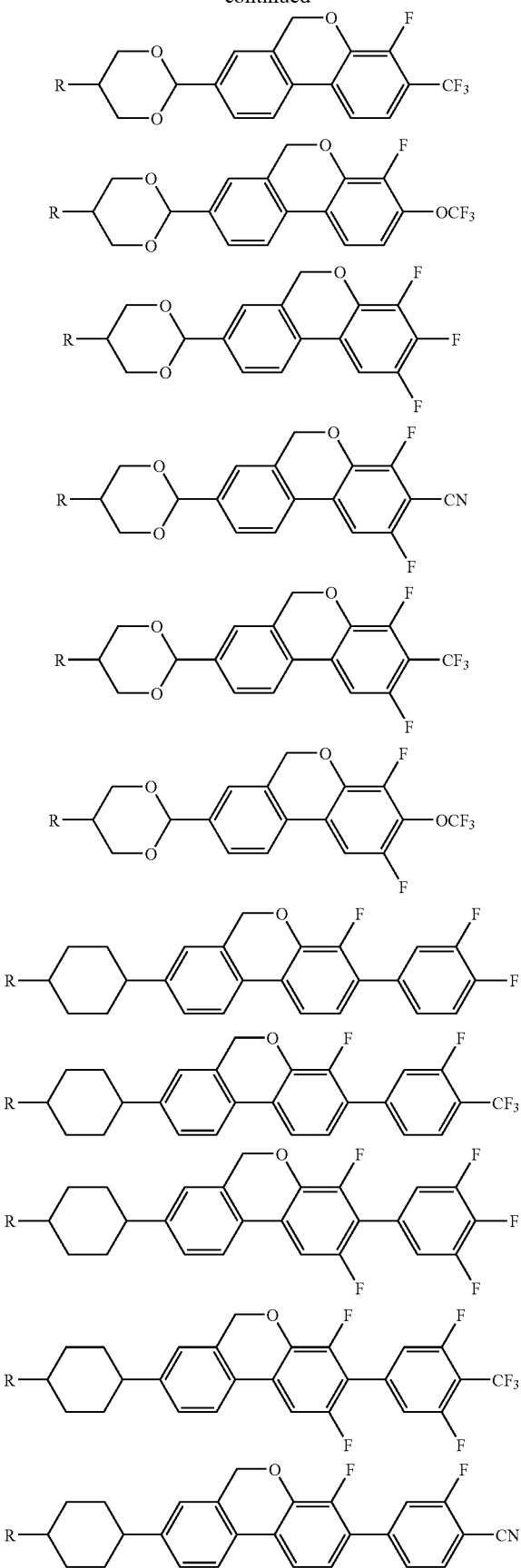
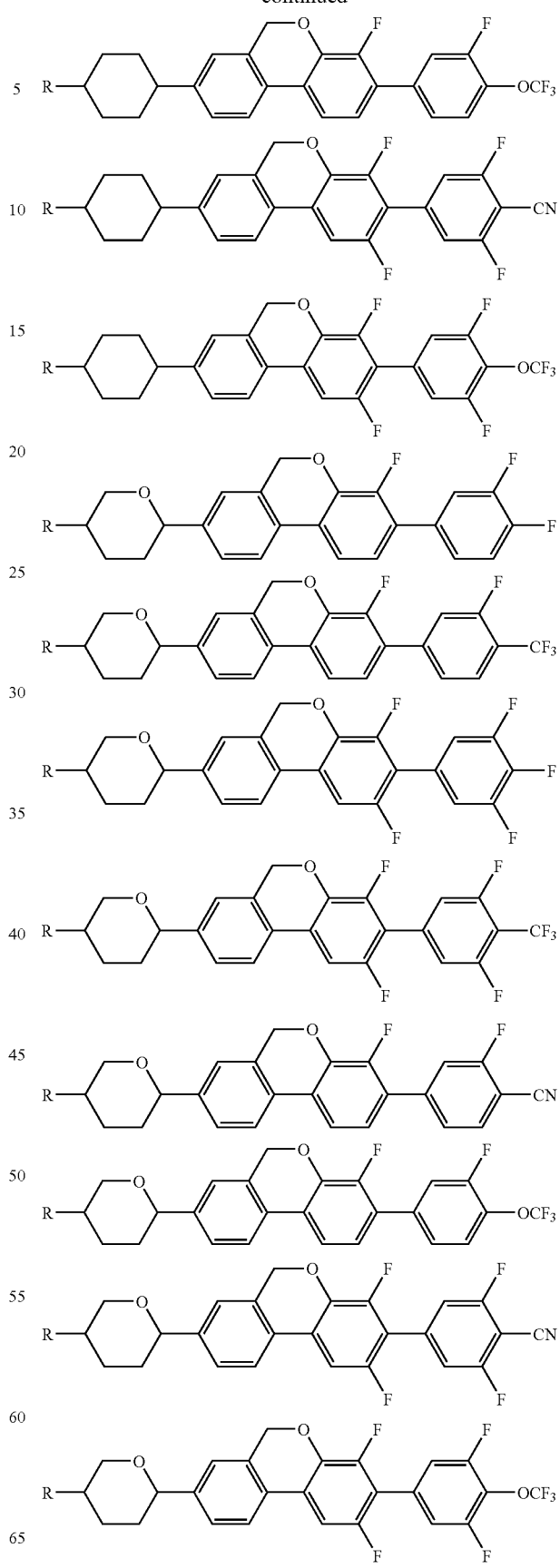

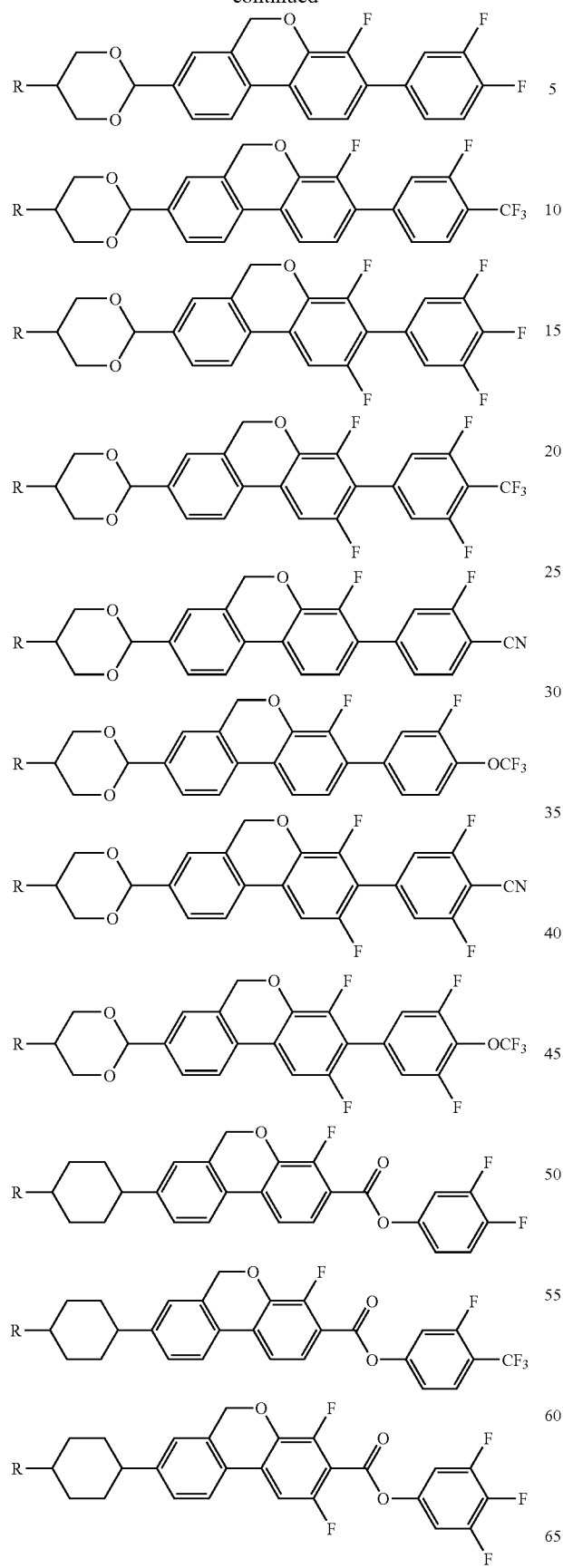
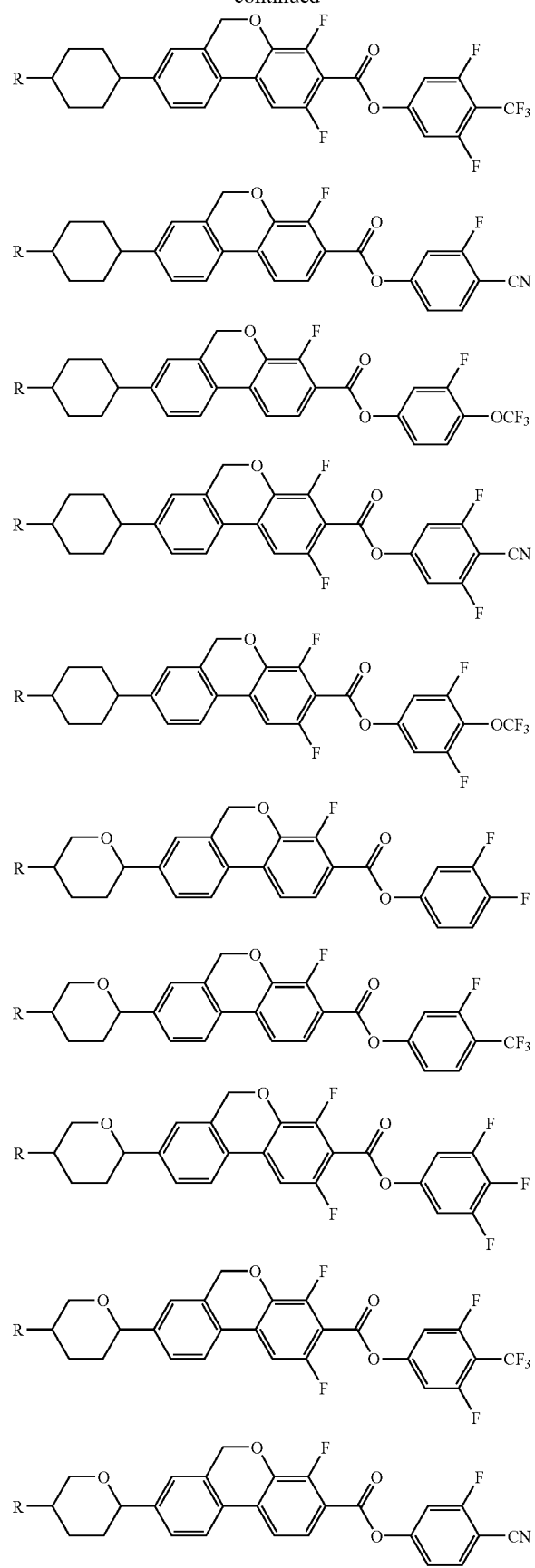

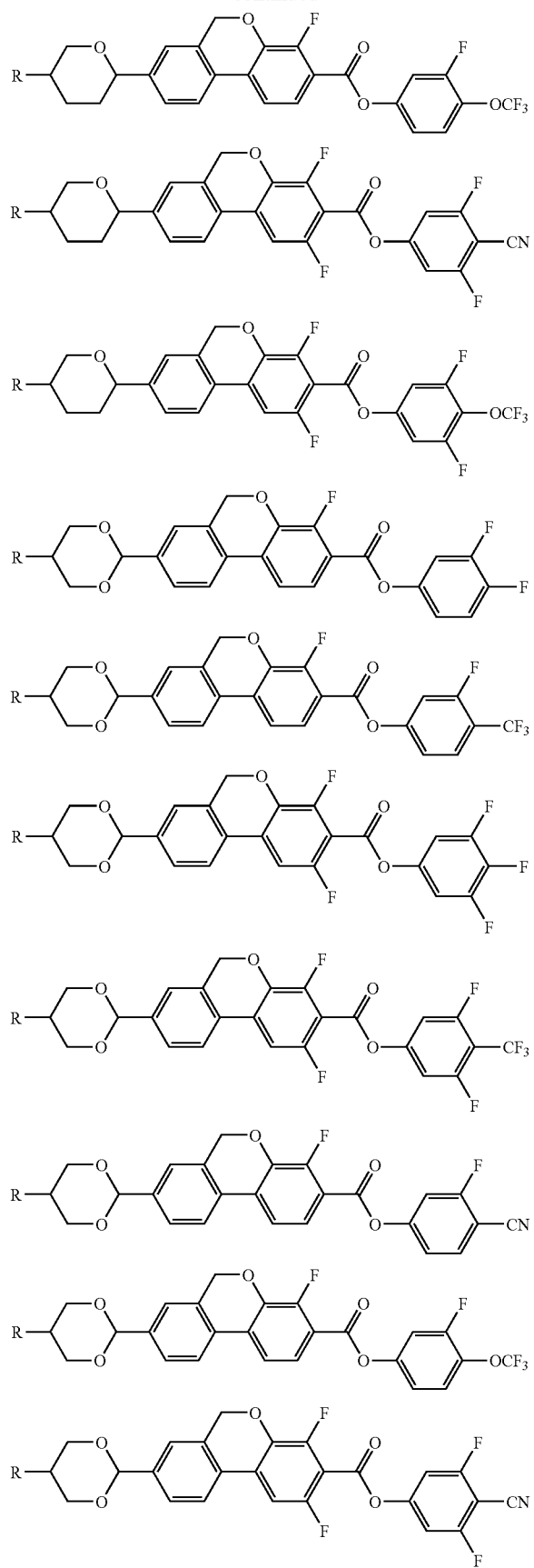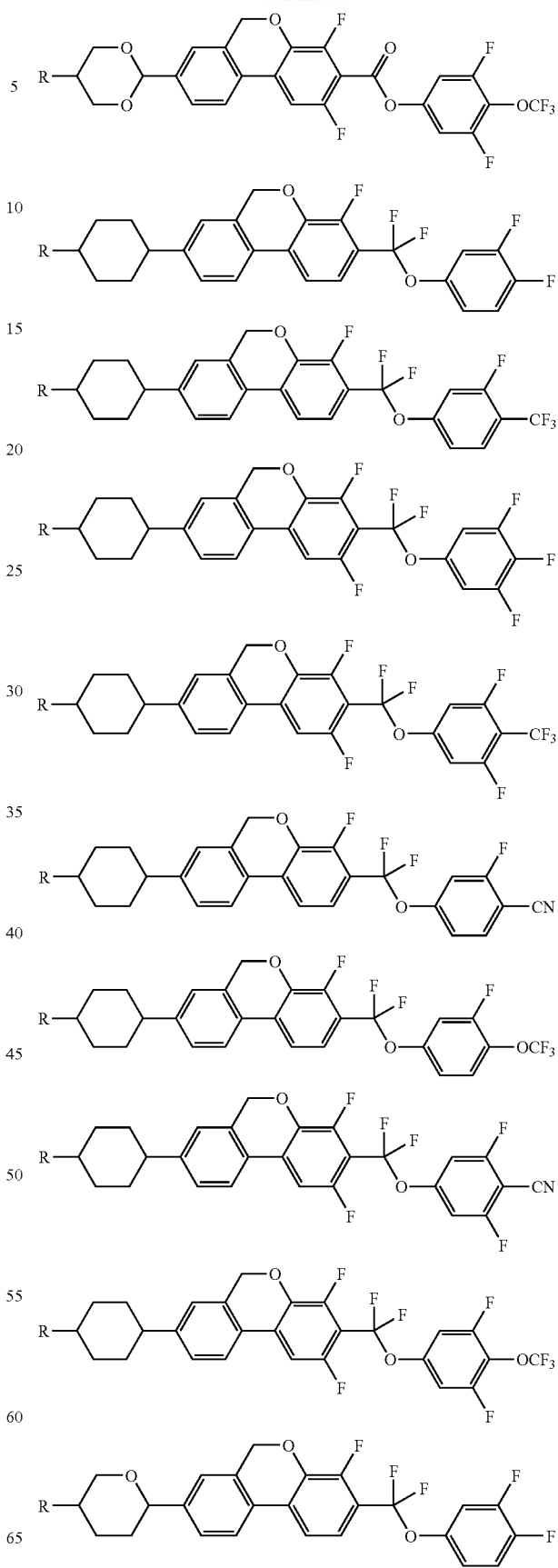

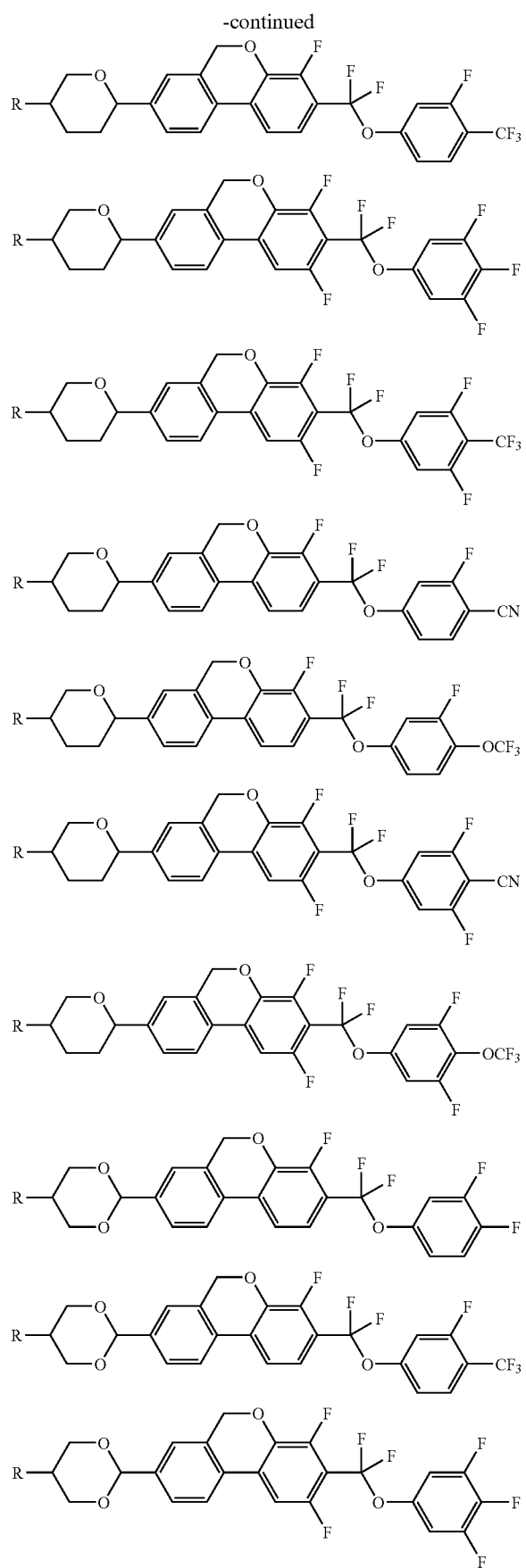
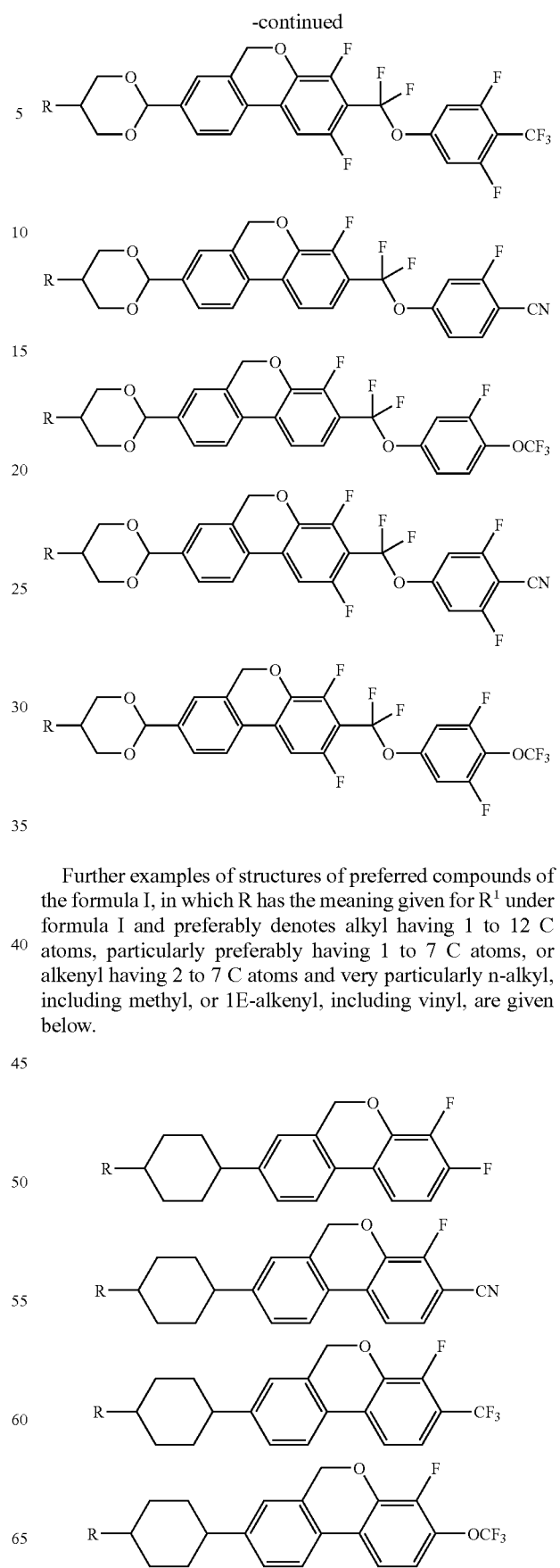
Further examples of structures of preferred compounds of the formula I, in which R has the meaning given for $R^1$ under formula I and preferably denotes alkyl having 1 to 12 C atoms, particularly preferably having 1 to 7 C atoms, or alkenyl having 2 to 7 C atoms and very particularly n-alkyl, including methyl, or 1E-alkenyl, including vinyl, are given below.
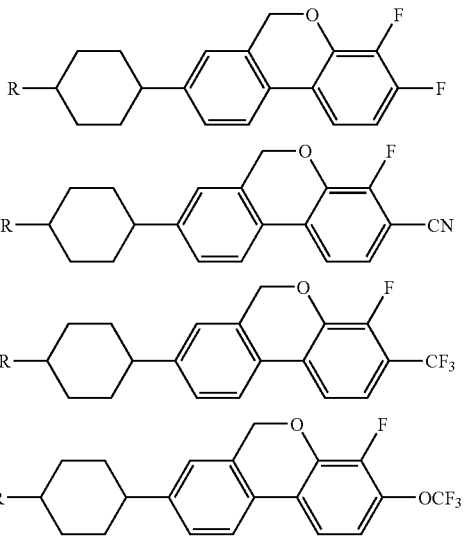

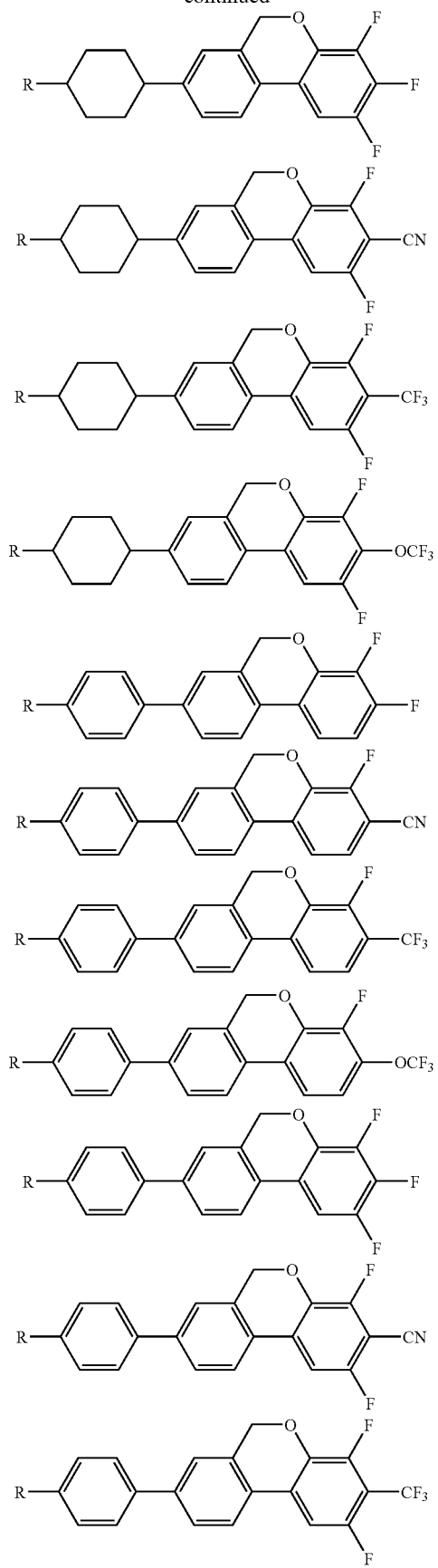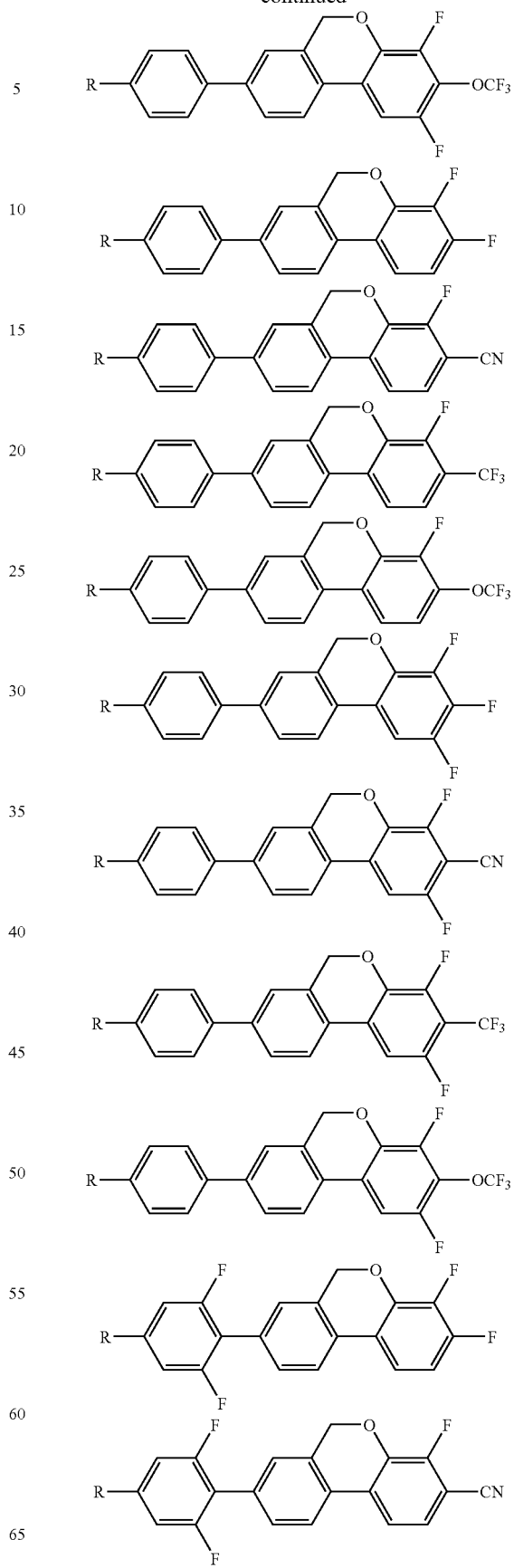

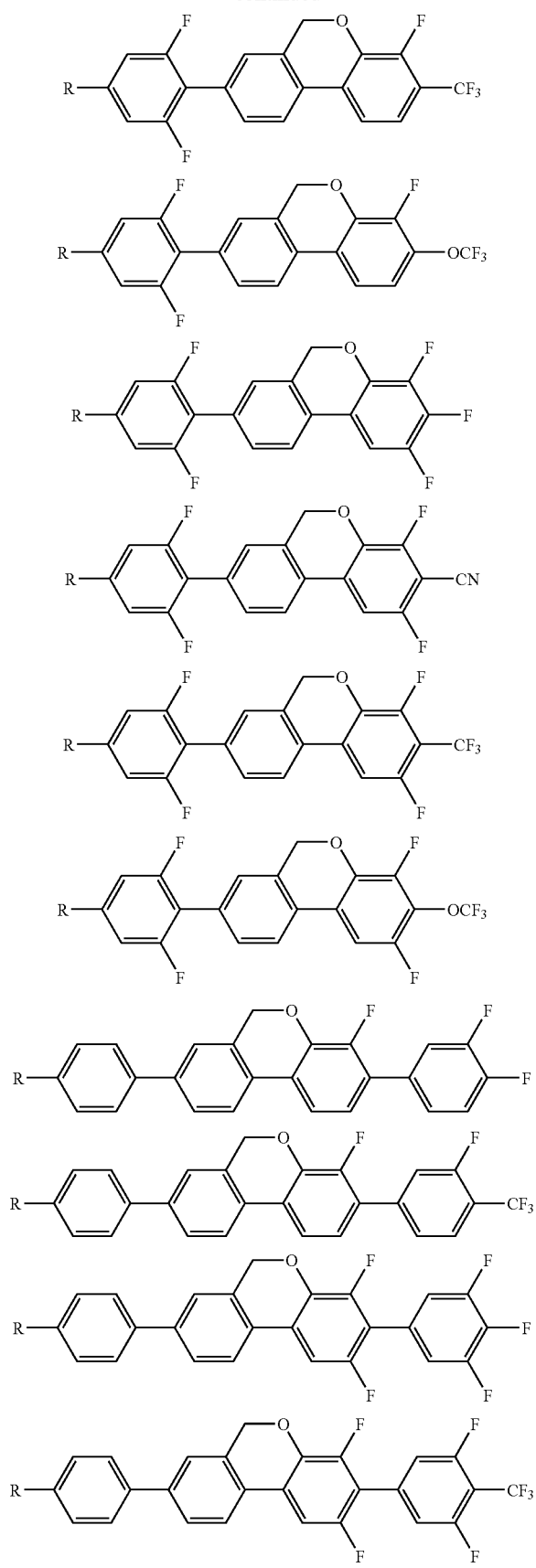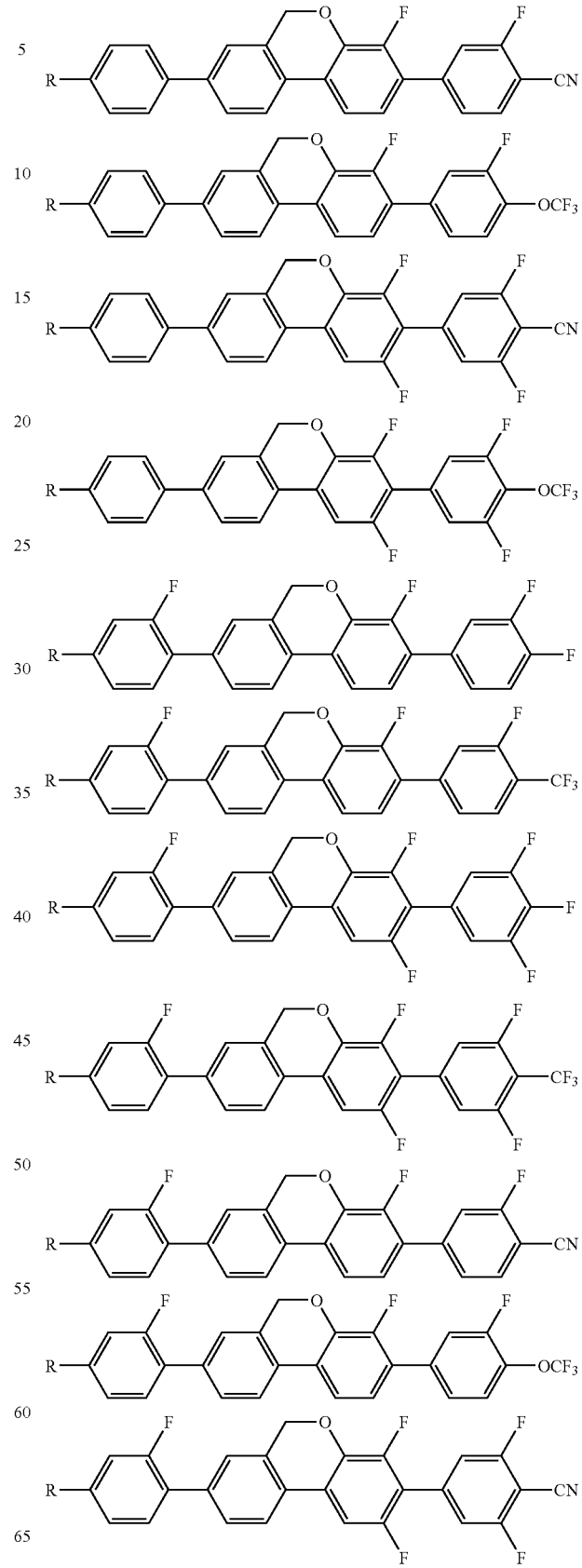

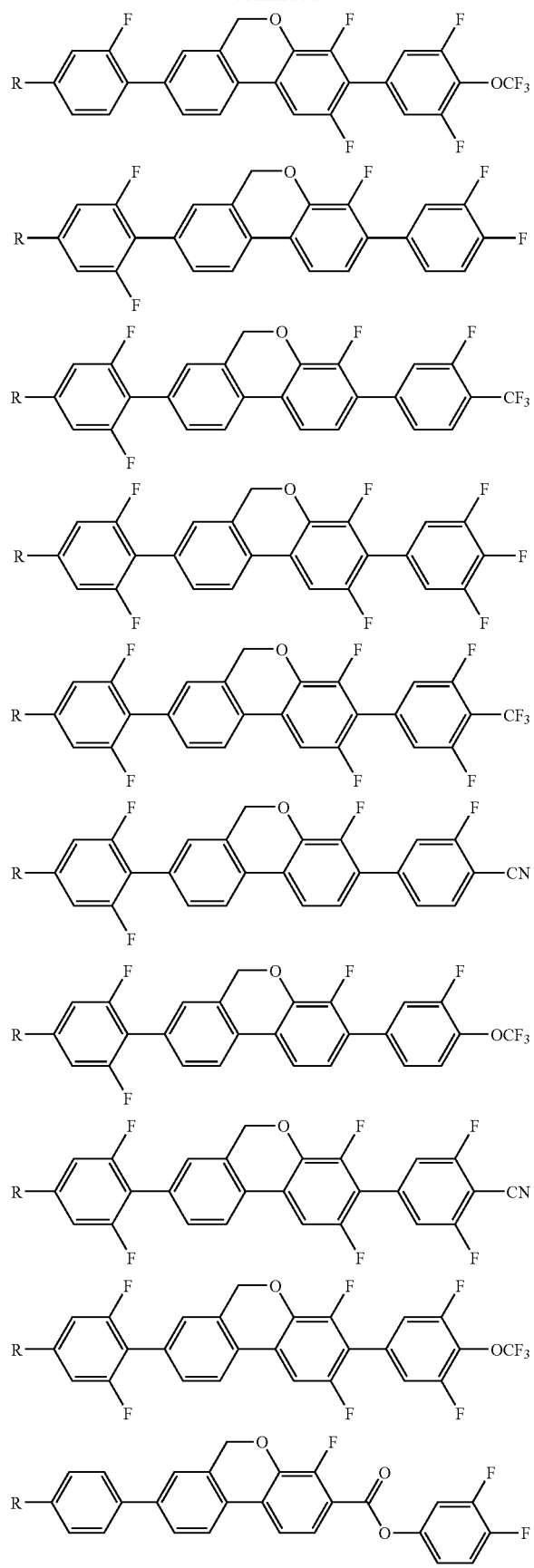
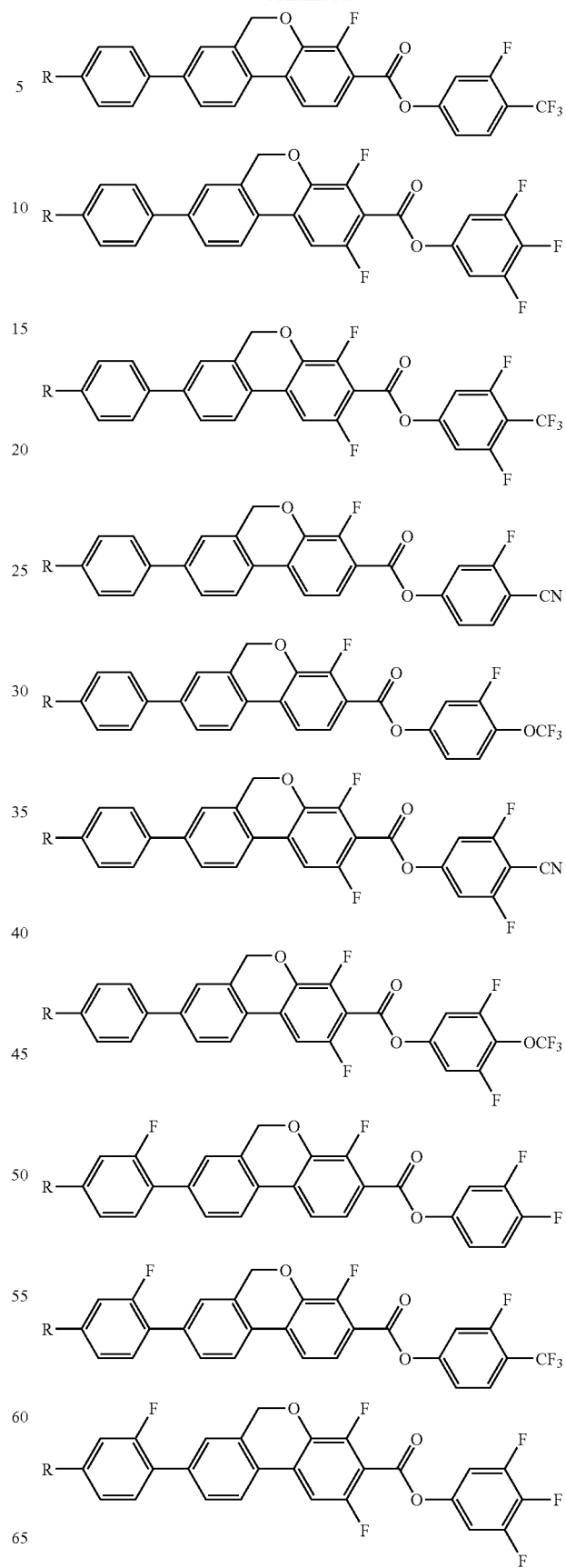

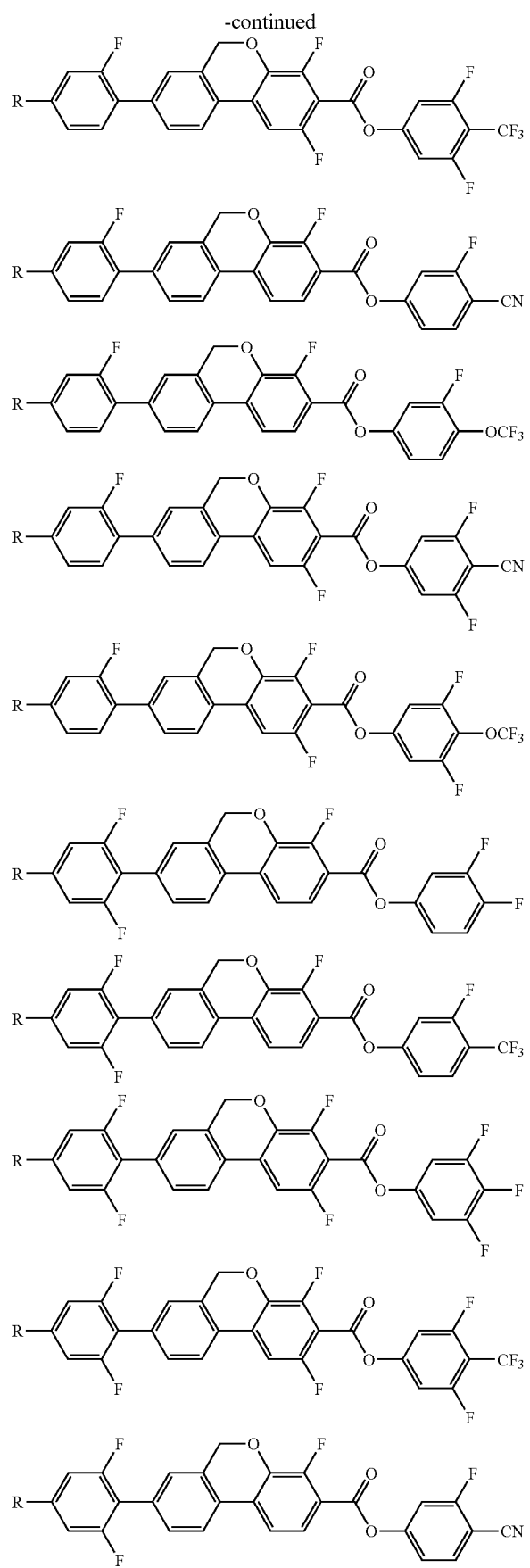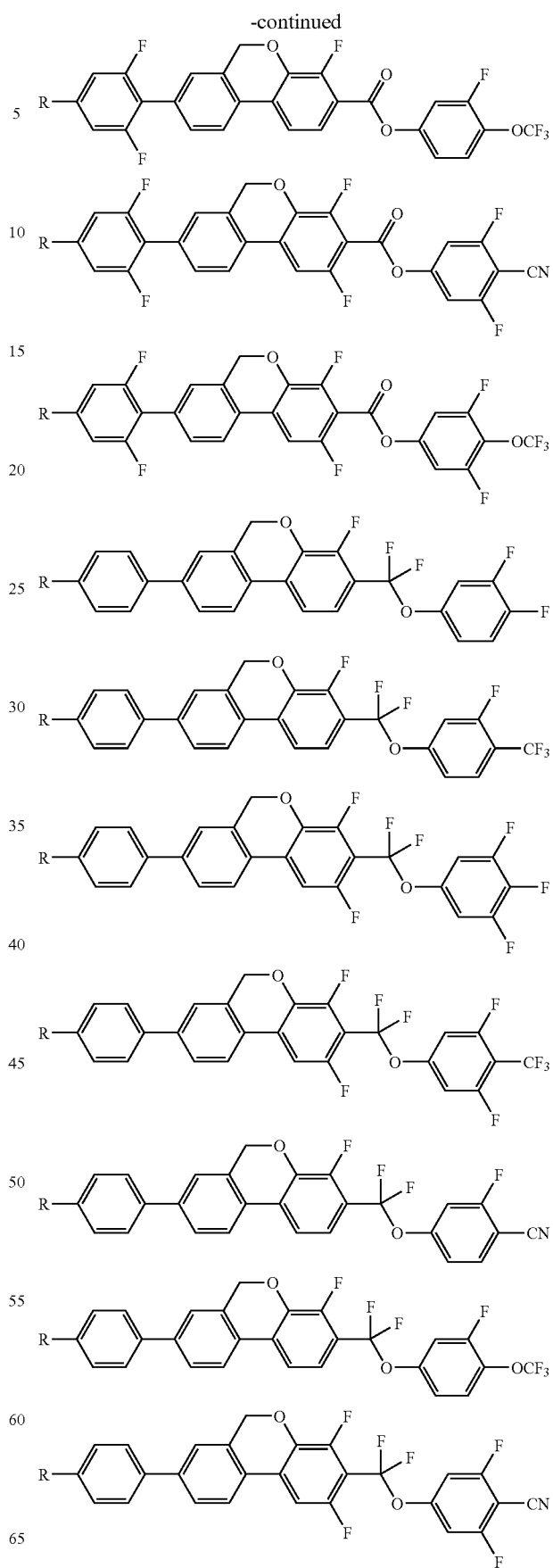

-continued

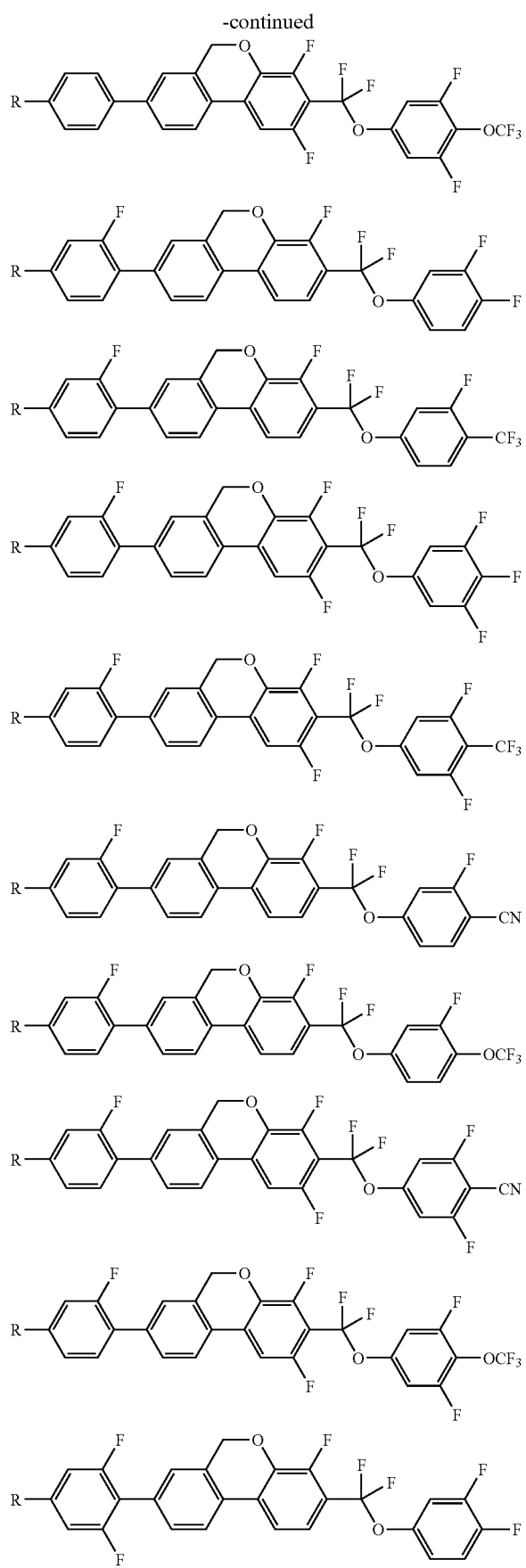
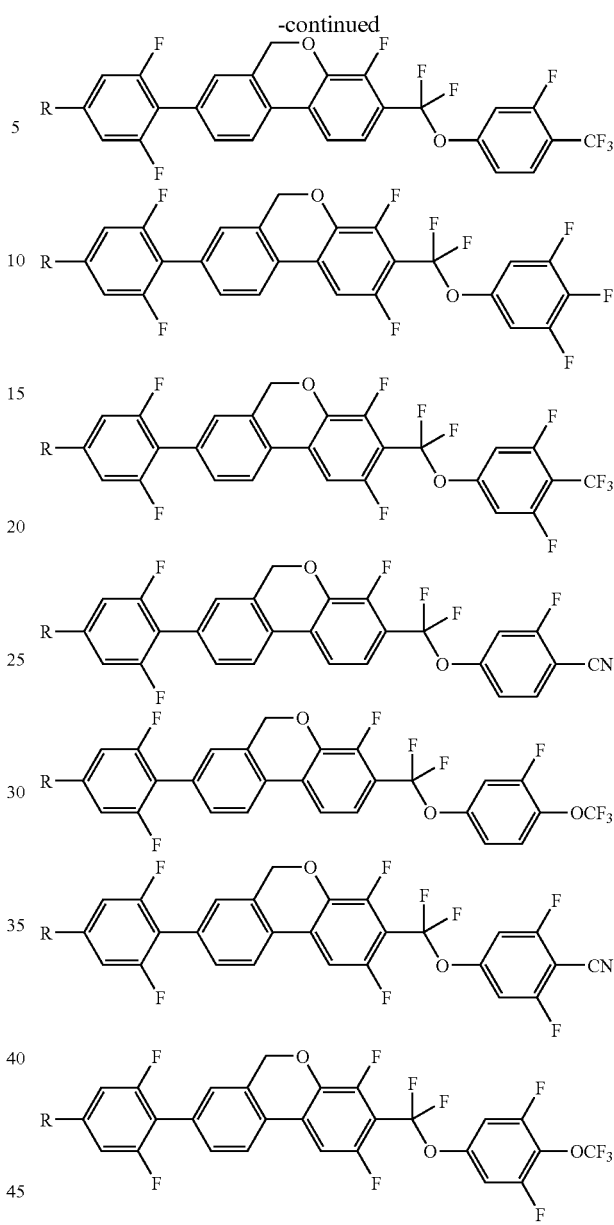

Compounds of the formula I according to the invention may be chiral owing to their molecular structure and can accordingly occur in various enantiomeric forms. They can therefore be in racemic or optically active form.

Since the pharmaceutical efficacy of the racemates or stereoisomers of the compounds according to the invention may differ, it may be desirable to use the enantiomers. In these cases, the end product or alternatively even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline) or the various optically active camphorsulfonic acids. Also advantageous is chromatographic enantiomer separation with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention encompasses not only the said compounds, but also mixtures and compositions which, besides these compounds according to the invention, also comprise other pharmacological active ingredients or adjuvants which are able to influence the primary pharmacological action of the compounds according to the invention in the desired manner.

The compounds according to the invention can be employed as medicament active ingredients in human or veterinary medicine, in particular for the prophylaxis or therapy of diseases which can be influenced by the central-nervous action of the compounds.

The compounds according to the invention can particularly preferably be employed for treating sexual disorders or increasing sexual performance, diarrhoea, nicotine dependence, inflammatory CNS diseases (demyelination, viral meningitis, multiple sclerosis, Guillain-Barré syndome) and accident-induced brain injuries or head injuries, appetence disorders, i.e. dependences of various types (drugs, alcohol, sugar), bulimia and any consequences thereof (obesity, diabetes).

They are furthermore active against hypertension or act against anxiety states and/or depression, as sedative, tranquilliser, analgesic, antiemetic or they have an inflammation-inhibiting action.

The central-nervous action can be demonstrated by administration to rats in doses of 0.1-1000 mg/kg, preferably of 1-100 mg/kg. Effects such as reduced spontaneous motor activity are observed, where the requisite dose depends both on the efficacy of the compound and also on the body weight of the experimental animal.

The invention accordingly relates to compounds of the formulae defined above and below and in the claims, including physiologically acceptable salts thereof, as medicaments, diagnostic agents or reagents.

The invention also relates to corresponding pharmaceutical compositions which comprise at least one medicament of the formula I and optionally excipients and/or adjuvants. Suitable excipients are organic or inorganic substances which are suitable for enteral (for example oral), parenteral or topical administration or for administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc and Vaseline. Suitable for oral use are, in particular, tablets, pills, dragees, capsules, powders, granules, syrups, juices or drops, suitable for rectal use are suppositories, suitable for parenteral use are solutions, preferably oily or aqueous solutions, furthermore suspensions, emulsions or implants, and suitable for topical use are ointments, creams or powders. The novel compounds may also be lyophilised and the resultant lyophilisates used, for example, for the preparation of injection preparations. The compositions indicated may have been sterilised and/or comprise adjuvants, such as lubricants, preservatives, stabilisers and/or wetting agents, emulsifiers, salts for modifying the osmotic pressure, buffer substances, colorants, flavours and/or a plurality of further active ingredients, for example one or more vitamins.

For administration as inhalation spray, it is possible to use sprays which comprise the active ingredient either dissolved or suspended in a propellant gas or propellant-gas mixture (for example $CO_2$). The active ingredient here is advantageously used in micronised form, where one or more additional physiologically tolerated solvents may be present, for example ethanol. Inhalation solutions can be administered with the aid of conventional inhalers.

The substances according to the invention can generally be administered analogously to other, commercially available THC analogues, preferably in doses of between about 0.05 and 500 mg, in particular between 0.5 and 100 mg, per dosage unit. The daily dose is preferably between about 0.01 and 20 mg/kg of body weight. However, the specific dose for each patient depends on a very wide variety of factors, for example on the efficacy of the specific compound employed, on the age, body weight, general state of health, sex, on the diet, on the administration time and method, on the excretion rate, medicament combination and severity of the particular disease to which the therapy applies.

Furthermore, the novel compounds of the formula I can be used in analytical biology and molecular biology.

Specific ligand binding to the receptors is defined as the difference between complete binding and non-specific binding, which is determined in the presence of an excess of unlabelled ligands (see, for example, MUNRO, S., THOMAS, K. L. and ABU-SHAAR, M. (1993), Molecular characterization of a peripheral receptor for cannabinoids. *Nature*, 365: 61-65. RINALDI-CARMONA, M., CALANDRA, B., SHIRE, D., BOUABOULA, M., OUSTRIC, D., BARTH, F., CASELLAS, P., FERRARA, P. and LE FUR, G. (1996), Characterization of two cloned human $CB_1$ cannabinoid receptors isoform; *J. Pharmacol. Exp. Ther.*, 278:871-878).

The present invention also relates to liquid-crystal media which comprise one or more compound(s) of the formula I.

In a preferred embodiment, the liquid-crystal media in accordance with the present invention comprise a) one or more dielectrically positive compound(s) of the formula I

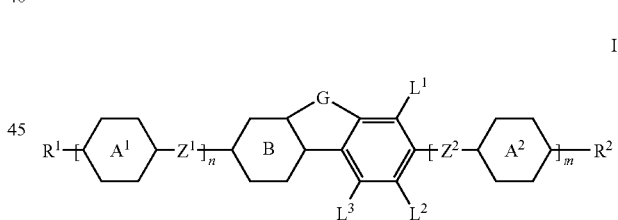

in which
G denotes —CO—O—, —CH$_2$—O—, —CF$_2$—O—, —O—CO—, —CH$_2$—O— or —O—CF$_2$—, preferably CH$_2$O,

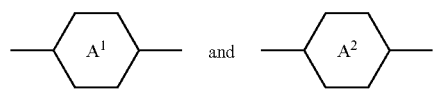

each, independently of one another and, if present more than once, also these independently of one another, denote
(a) a trans—1,4—cyclohexylene radical, in which, in addition, one or two non—adjacent CH$_2$ groups may be replaced by —O— and/or —S—,
(b) a 1,4—cyclohexenylene radical, (c) a 1,4—phenylene radical, in which, in addition, one or two non—adjacent CH groups may be replaced by N, or
(d) naphthalene—2,6—diyl, decahydronaphthalene—2,6—diyl and 1,2,3,4—tetrahydronaphthalene—2,6—diyl,
(e) a radical selected from the group 1,4—bicyclo[2.2.2]octylene, 1,3—bicyclo[1.1.1]pentylene, spiro[3.3]heptane—2,6—diyl and 1,3—cyclobutylene,
where in
(a) and (b), one or more —$CH_2$— groups, independently of one another, may each be replaced by a —CHF— or —$CF_2$— group, and in
(c) and (d), one or more —CH= groups, independently of one another, may each be replaced by a —CF=, —C(CN)=, —C($CH_3$)=, —C($CH_2F$)=, —C($CHF_2$)=, —C(O—$CH_3$)=, —C(O—$CHF_2$)= or —C(O—$CF_3$)= group, preferably a —CF= group, and preferably denote

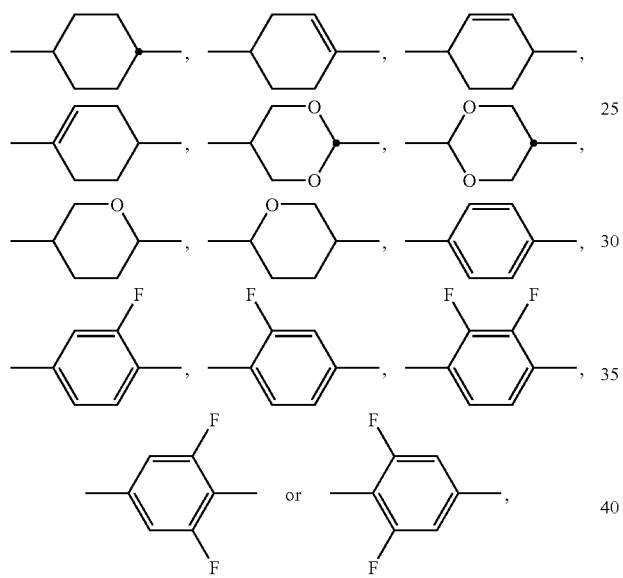

$L^1$ to $L^3$ each, independently of one another, denote H, halogen, CN or $CF_3$, preferably H, F or Cl, particularly preferably H or F, and very particularly preferably $L^1$ and/or $L^2$ denote F and $L^3$ denotes H,

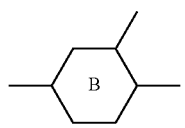

denotes a 1,4-trans-cyclohexane-1,2,4-triyl radical, in which, in addition, one or two non-adjacent $CH_2$ groups may be replaced by —O— and/or —S—, and one or more —$CH_2$— groups, in each case independently of one another, may each be replaced by a —CHF— or —$CF_2$— group, and the —CH< group may be replaced by a —CF< group, and which may optionally contain one, two or three C—C double bonds, where in this case one or more —CH= groups, independently of one another, may each be replaced by a —CF=, —C(CN)=, —C($CH_3$)=, —C($CH_2F$)=, —C($CHF_2$)=, —C(O—$CH_3$)=, —C(O—$CHF_2$)= or —C(O—$CF_3$)= group, preferably a —CF= group, $R^1$ and $R^2$ each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —$SF_5$, —$CF_3$, —$CHF_2$, —$CH_2F$, —$OCF_3$, —$OCHF_2$, an alkyl group having 1 to 15 C atoms which is monosubstituted by —CN or —$CF_3$ or at least mono-substituted by halogen, where, in addition, one or more $CH_2$ groups, in each case independently of one another, may be replaced by —O—, —S—, —CH=CH—, —CF=CF—, —CF=CH—, —CH=CF—,

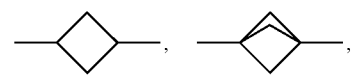

—CO—, —CO—O—, —O—CO— or —O—CO—O— in such a way that neither O nor S atoms are linked directly to one another, preferably one of
$R^1$ and $R^2$ denotes alkyl or alkoxy having 1 to 12 C atoms, alkoxyalkyl, alkenyl or alkenyloxy having 2 to 12 C atoms and the other, independently of the first, denotes halogen, —CN, —SCN, —NCS, —OCN, —$SF_5$, —$CF_3$, —$CHF_2$, —$CH_2F$, —$OCF_3$, —$OCHF_2$,
$Z^1$ and $Z^2$ each, independently of one another and, if present more than once, also these independently of one another, denote —$CH_2$—$CH_2$—, —$(CH_2)_4$—, —$CF_2$—$CF_2$—, —$CF_2$—$CH_2$—, —$CH_2$—$CF_2$—, —CH=CH—, —CF=CF—, —CF=CH—, —CH=CF—, —C≡C—, —CO—O—, —O—CO—, —$CH_2$—O—, —O—$CH_2$—, —$CF_2$—O—, —O—$CF_2$—, or a combination of two of these groups, where no two O atoms are bonded to one another, preferably —$(CH_2)_4$—, —$CH_2$—$CH_2$—, —$CF_2$—$CF_2$—, —CH=CH—, —CF=CF—, —C≡C—, —$CH_2$—O—, —$CF_2$—O— or a single bond, particularly preferably —$CH_2$—O—, —$CH_2$—$CH_2$—, —$CF_2$—$CF_2$—, —CF=CF—, —$CF_2$—O— or a single bond, and
n and m each denote 0, 1 or 2, where
n+m denotes 0, 1, 2 or 3, preferably 0, 1 or 2, particularly preferably 0 or 1.
b) one or more dielectrically positive compound(s) of the formula II

in which
$R^{21}$ has the meaning given above for $R^1$ in the case of formula I,
$X^{21}$ denotes halogen, —CN, —SCN, —NCS, —OCN, —$SF_5$, —$CF_3$, —$CHF_2$, —$CH_2F$, —$OCF_3$, —$OCHF_2$, an alkyl group having 1 to 15 C atoms which is monosubstituted by CN or $CF_3$ or at least monosubstituted by halogen and in which one or more $CH_2$ groups, in each case independently of one another, may be replaced by —O—, —S—, —CH=CH—, —CF=CF—, —CF=CH—, —CH=CF—,

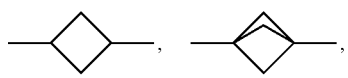

—CO—, —CO—O—, —O—CO— or —O—CO—O— in such a way that neither O nor S atoms are linked directly to one another, preferably F, Cl, —OCF$_3$, —OCF$_2$ or —CF$_3$, $Z^{21}$ and $Z^{22}$ each, independently of one another, have the meaning given above for $Z^1$ in the case of formula I, at least one of the rings present

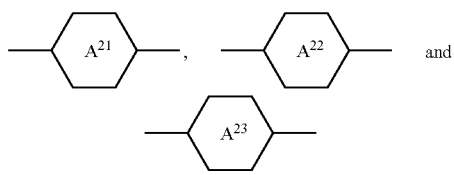

present, preferably

denotes

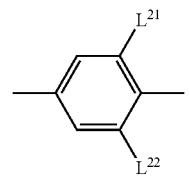

and the others, in each case independently of one another, denote

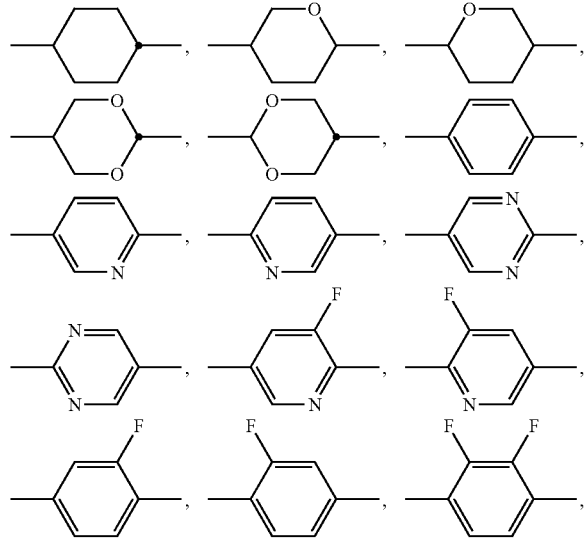

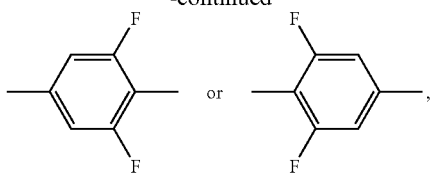

preferably

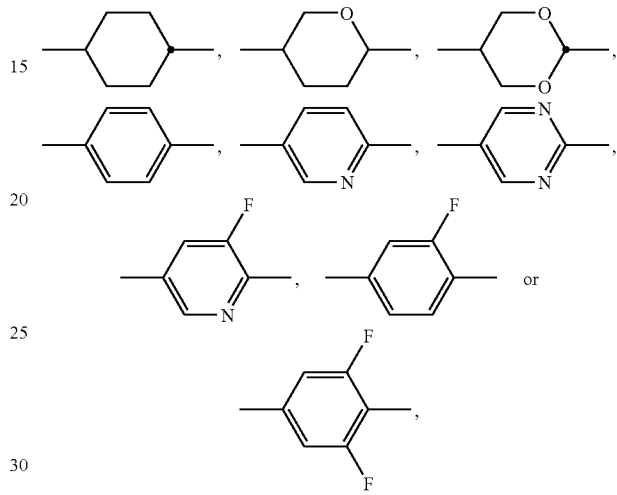

particularly preferably

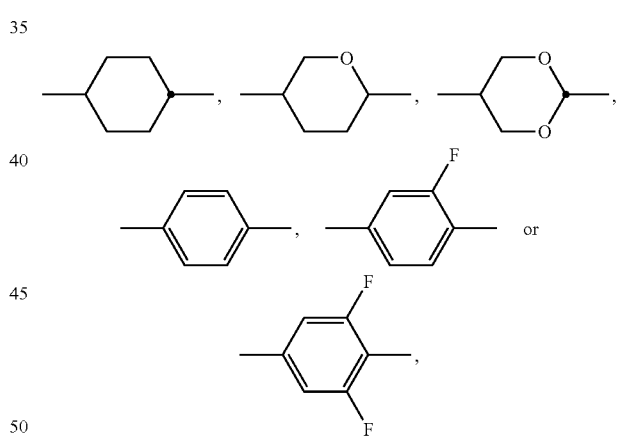

particularly preferably

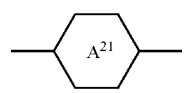

denotes

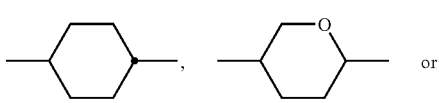

-continued

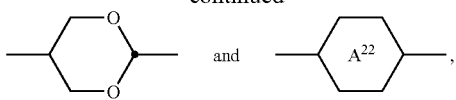

if present, denotes

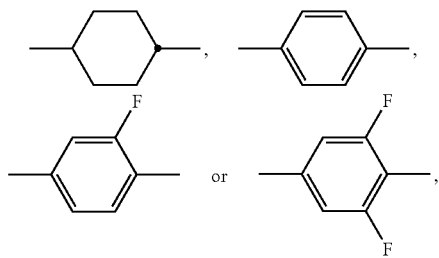

$L^{21}$ and $L^{22}$, independently of one another, denote H or F,
l denotes 0, 1 or 2, preferably 0 or 1;
and optionally
c) one or more dielectrically neutral compounds of the formula III

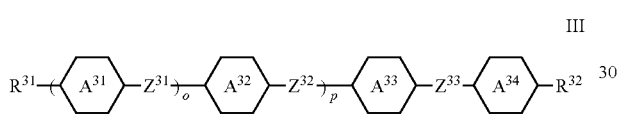

in which
$R^{31}$ and $R^{32}$ each, independently of one another, have the meaning given above for $R^1$ in the case of formula I, and
$Z^{31}$, $Z^{32}$ and $Z^{33}$ each, independently of one another, denote —CH$_2$CH$_2$—, —CH=CH—, —COO— or a single bond,

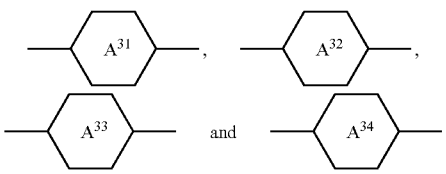

each, independently of one another, denote

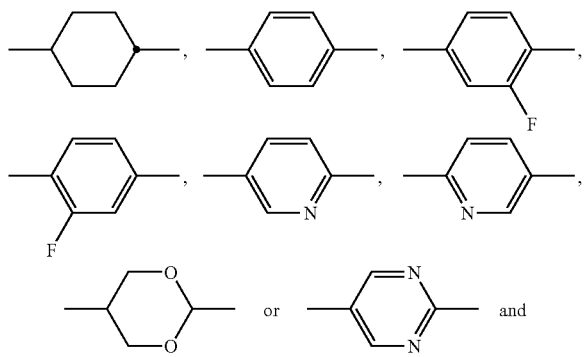

o and p, independently of one another, denote 0 or 1,
but preferably
$R^{31}$ and $R^{32}$ each, independently of one another, denote alkyl or alkoxy having 1-5 C atoms or alkenyl having 2-5 C atoms,

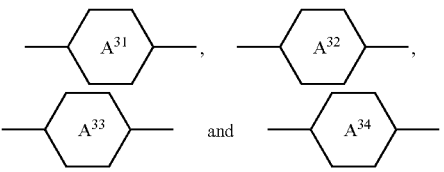

each, independently of one another, denote

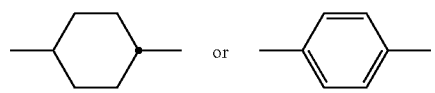

and very particularly preferably at least two of these rings denote

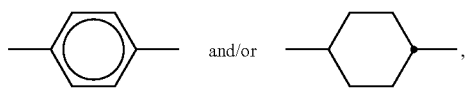

where very particularly preferably two adjacent rings are linked directly, to be precise preferably

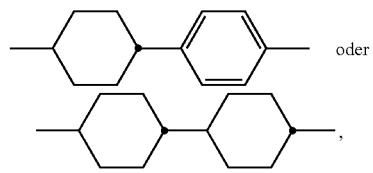

where in the case of the phenylene ring, one or more H atoms, independently of one another, may be replaced by F or CN, preferably by F, and one or two non-adjacent CH$_2$ groups of the cyclohexylene ring or of one of the cyclohexylene rings may be replaced by O atoms.

The liquid-crystal media preferably comprise one or more compounds of the formula I which contain no biphenyl unit.

The liquid-crystal media particularly preferably comprise one or more compounds of the formula I
in which two adjacent rings are linked directly, to be precise preferably

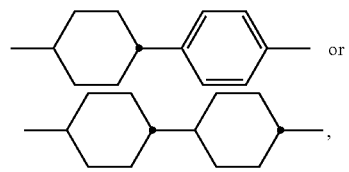

where in the case of the phenylene ring, one or more H atoms, independently of one another, may be replaced by F or CN, preferably by F, and one or two non-adjacent CH$_2$ groups of the cyclohexylene ring or of one of the cyclohexylene rings may be replaced by O atoms.

In a preferred embodiment, which may be identical with the embodiments just described, the liquid-crystal media comprise one or more compounds selected from the group of the compounds of the formula I-3.

The liquid-crystal medium preferably comprises one or more compounds selected from the group of the compounds of the formulae II-1 to II-4

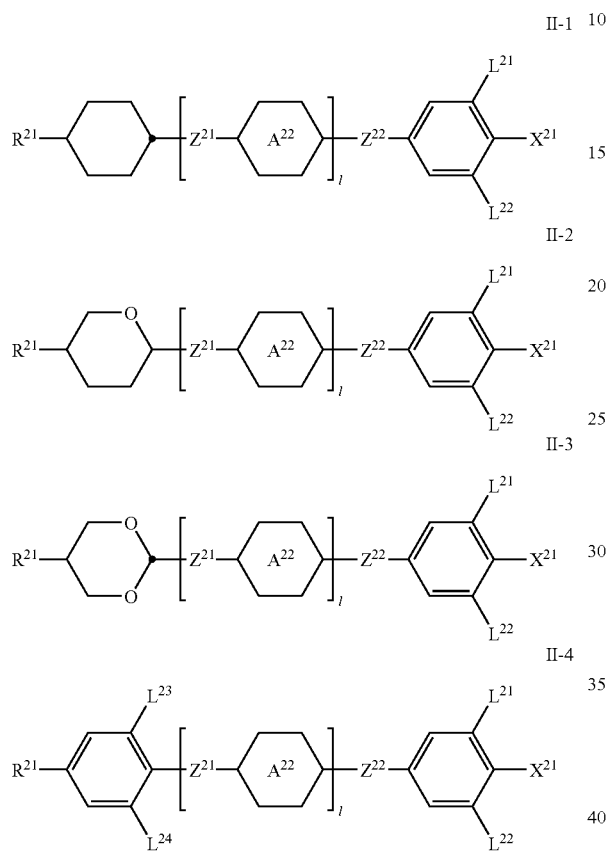

in which
$R^{21}, X^{21}, Z^{12}, Z^{22}, L^{21}, L^{22}$,

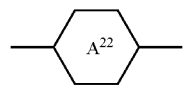

and l each have the meaning given above in the case of formula II, and
$L^{23}$ and $L^{24}$, independently of one another, denote H or F, and
in the case of formula II-4,

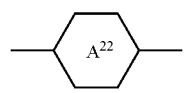

preferably denotes an aromatic ring.
Particularly preferably,
$R^{21}$ is alkyl or alkoxy, preferably having 1-5 C atoms, preferably alkyl, and in the case where I=0,
$Z^{22}$ is —CF$_2$O—, —CO—O— or a single bond, particularly preferably a single bond,
in the case where I=1 or 2,
$Z^{21}$ and $Z^{22}$ are both a single bond or $Z^{22}$ or one of the $Z^{21}$ present is —CO—O—, —CF$_2$O— or —CH═CH—, preferably —CO—O— or —CF$_2$O—, particularly preferably —CF$_2$O—, and the others are single bond.

The liquid-crystal medium especially preferably comprises one or more compounds selected from the group of the compounds of the formulae II-1a to II-1h, II-2a to II-2d, II-3a and III-3b and II-4a to II-4c

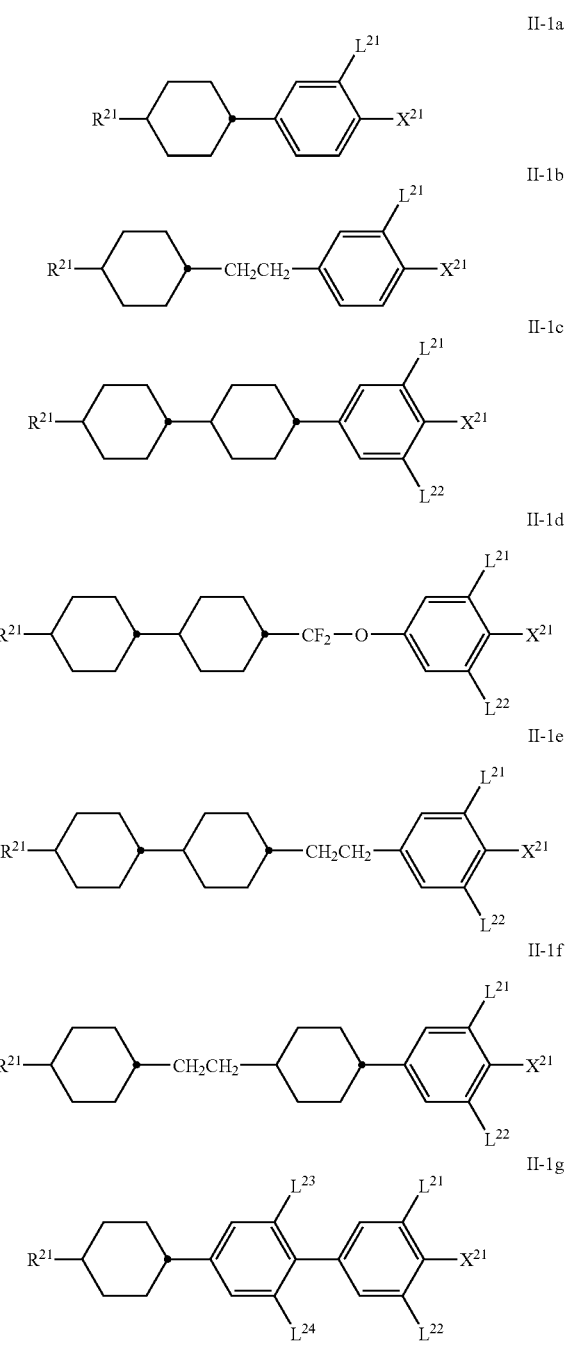

II-1h
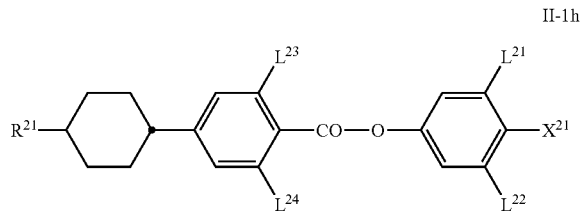

II-2a
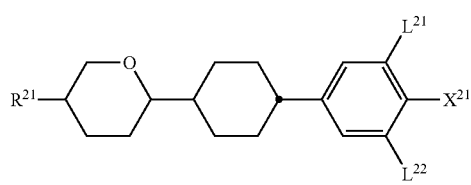

II-2b
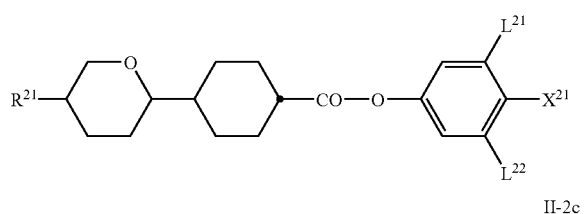

II-2c
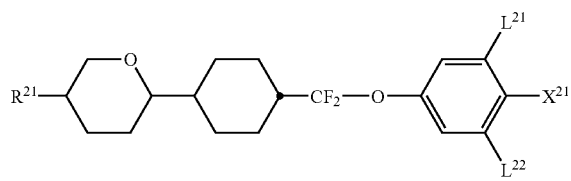

II-2d
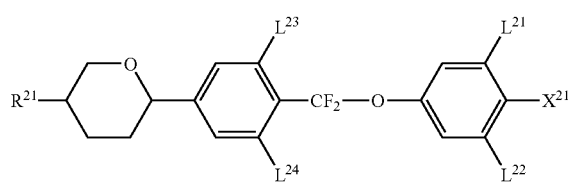

II-3a
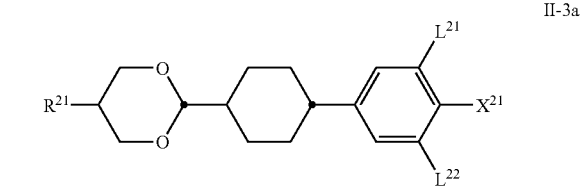

II-3b
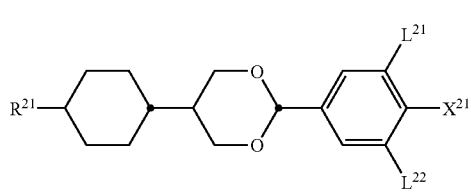

II-4a
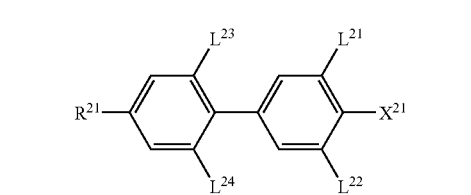

II-4b
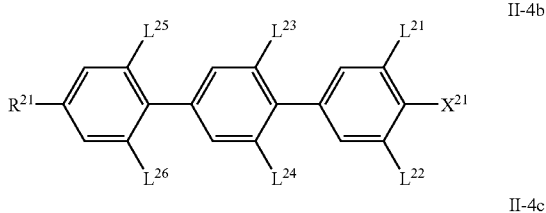

II-4c
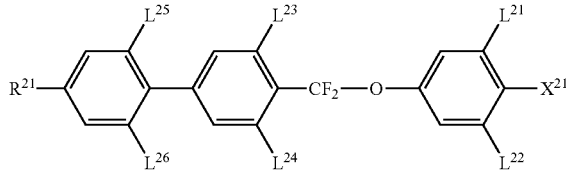

in which
$R^{21}$ and $X^{21}$ each have the meaning given above in the case of formula II, and $L^{23}$ to $L^{26}$, independently of one another, denote H or F.

The liquid-crystal medium particularly preferably comprises one or more compounds selected from the group of the compounds of the formulae III-1 to III-3:

III-1
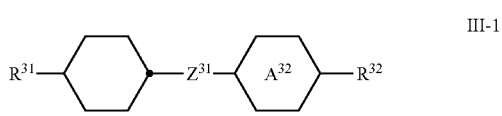

III-2
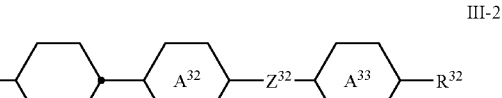

III-3
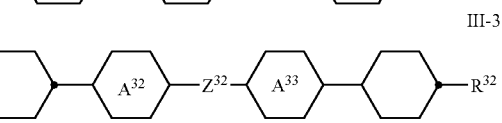

in which $R^{31}$, $R^{32}$, $Z^{32}$,

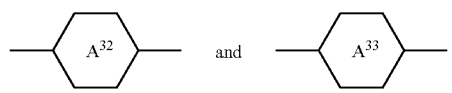

each have the meaning indicated above for formula III.

The liquid-crystal medium especially preferably comprises one or more compounds selected from the group of the compounds of the formulae III-1a to III-1d, III-1e, III-2a to III-2g, III-3a to III-3d and III-4a:

III-1a
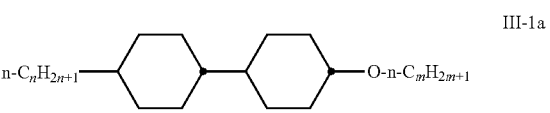

III-1b
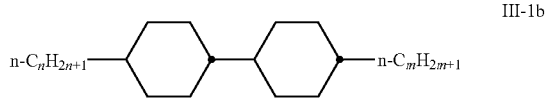

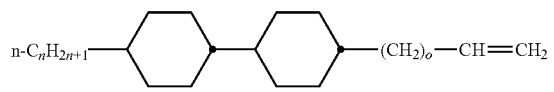
III-1c

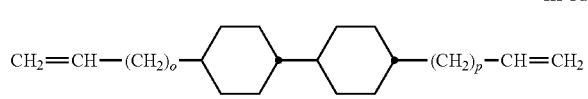
III-1d in which n and m each, independently of one another, denote 1 to 5, and o and p each, independently both thereof and of one another, denote 0 to 3,

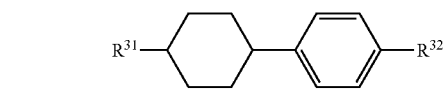
III-1e

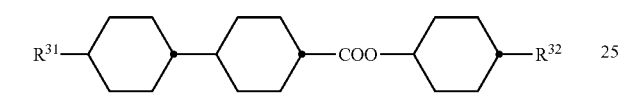
III-2a

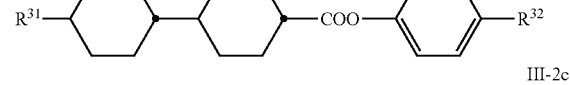
III-2b

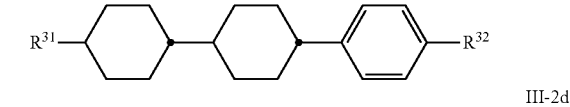
III-2c

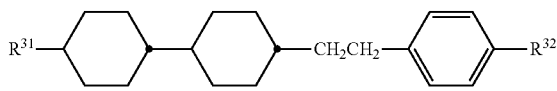
III-2d

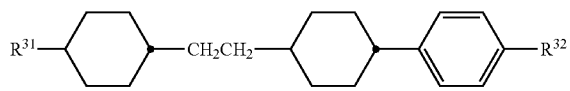
III-2e

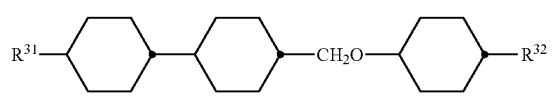
III-2f

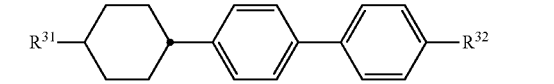
III-2g

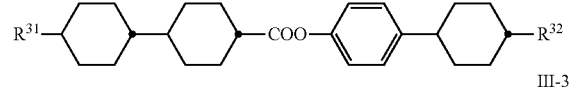
III-3a

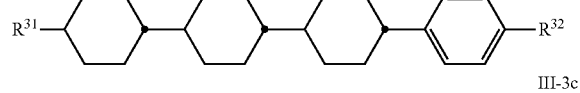
III-3b

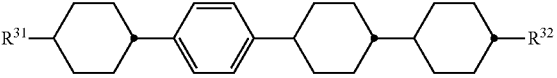
III-3c

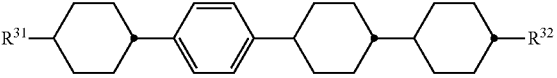
III-3d in which $R^{31}$ and $R^{33}$ each have the meaning indicated above under formula III, preferably the meaning indicated under formula III-1, and the phenyl rings, in particular in the compounds III-2g and III-3c, may optionally be fluorinated, but not in such a way that the compounds are identical with those of the formula II and its sub-formulae. $R^{31}$ is preferably n-alkyl having 1 to 5 C atoms, especially preferably having 1 to 3 C atoms, and $R^{32}$ is preferably n-alkyl or n-alkoxy having 1 to 5 C atoms or alkenyl having 2 to 5 C atoms. Of these, especial preference is given to compounds of the formulae III-1a to III-1d.

Preferred fluorinated compounds of the formulae III-2g and III-3c are the compounds of the formulae III-2g′ and III-3c′

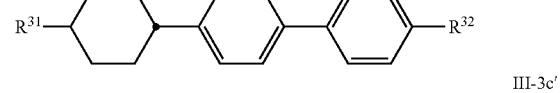
III-2g′

III-3c′ in which $R^{31}$ and $R^{33}$ each have the meaning indicated above under formula III, preferably the meaning indicated under formula III-2g or III-3c.

In the present application, the term compounds is taken to mean both one compound and a plurality of compounds, unless expressly stated otherwise.

The liquid-crystal media according to the invention preferably have nematic phases of in each case from at least −20° C. to 80° C., preferably from −30° C. to 85° C. and very particularly preferably from −40° C. to 100° C. The term "have a nematic phase" here is taken to mean firstly that no smectic phase and no crystallisation are observed at low temperatures at the corresponding temperature and secondly also that no clearing occurs on heating from the nematic phase. The investigation at low temperatures is carried out in a flow viscometer at the corresponding temperature and checked by storage in test cells having a layer thickness corresponding to the electro-optical application for at least 100 hours. At high temperatures, the clearing point is measured in capillaries by conventional methods.

Furthermore, the liquid-crystal media according to the invention are characterised by low optical anisotropy values.

The term "alkyl" preferably encompasses straight-chain and branched alkyl groups having 1 to 7 carbon atoms, in particular the straight-chain groups methyl, ethyl, propyl, butyl, pentyl, hexyl and heptyl. Groups having 2 to 5 carbon atoms are generally preferred.

The term "alkenyl" preferably encompasses straight-chain and branched alkenyl groups having 2 to 7 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 6. Preferably, n is 1 and m is 1 to 6.

Compounds containing a vinyl end group and compounds containing a methyl end group have low rotational viscosity.

In the present application, the term dielectrically positive compounds denotes compounds having a $\Delta\epsilon$ of >1.5, the term dielectrically neutral compounds denotes those in which $-1.5 \leq \Delta\epsilon \leq 1.5$, and the term dielectrically negative compounds denotes those having a $\Delta\epsilon$ of <−1.5. The dielectric anisotropy of the compounds is determined here by dissolving 10% of the compounds in a liquid-crystalline host and determining the capacitance of this mixture at 1 kHz in at least one test cell with a layer thickness of about 20 μm having a homeotropic surface alignment and at least one test cell with a layer thickness of about 20 μm having a homogeneous surface alignment. The measurement voltage is typically 0.5 V to 1.0 V, but is always less than the capacitive threshold of the respective liquid-crystal mixture.

The host mixture used for determining the applicationally relevant physical parameters is ZLI-4792 from Merck KGaA, Germany. As an exception, the determination of the dielectric anisotropy of dielectrically negative compounds is carried out using ZLI-2857, likewise from Merck KGaA, Germany. The values for the respective compound to be investigated are obtained from the change in the properties, for example the dielectric constants, of the host mixture after addition of the compound to be investigated and extrapolation to 100% of the compound employed.

The concentration employed for the compound to be investigated is 10%. If the solubility of the compound to be investigated is inadequate for this purpose, the concentration employed is, by way of exception, halved, i.e. reduced to 5%, 2.5%, etc., until the concentration is below the solubility limit.

The term threshold voltage usually relates to the optical threshold for 10% relative contrast ($V_{10}$). In relation to the liquid-crystal mixtures of negative dielectric anisotropy, however, the term threshold voltage is used in the present application for the capacitive threshold voltage ($V_0$), also known as the Freedericksz threshold, unless explicitly stated otherwise.

All concentrations in this application, unless explicitly stated otherwise, are indicated in percent by weight and relate to the corresponding mixture as a whole. All physical properties are and have been determined in accordance with "Merck Liquid Crystals, Physical Properties of Liquid Crystals", status November 1997, Merck KGaA, Germany, and apply to a temperature of 20° C., unless explicitly stated otherwise. $\Delta n$ is determined at 589 nm and $\Delta\epsilon$ at 1 kHz.

In the case of the liquid-crystal media of negative dielectric anisotropy, the threshold voltage was determined as the capacitive threshold $V_0$ in cells with a liquid-crystal layer aligned homeotropically by means of lecithin.

The liquid-crystal media according to the invention may, if necessary, also comprise further additives and optionally also chiral dopants in the conventional amounts. The amount of these additives employed is in total from 0% to 10%, based on the amount of the mixture as a whole, preferably from 0.1% to 6%. The concentrations of the individual compounds employed are in each case preferably from 0.1 to 3%. The concentration of these and similar additives is not taken into account when indicating the concentrations and the concentration ranges of the liquid-crystal compounds in the liquid-crystal media.

The compositions consist of a plurality of compounds, preferably 3 to 30, particularly preferably 6 to 20 and very particularly preferably 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituent, the completion of the dissolution process is particularly easy to observe. However, it is also possible to prepare the liquid-crystal mixtures in other conventional ways, for example using premixes or from a so-called "multibottle" system.

By means of suitable additives, the liquid-crystal phases according to the invention can be modified in such a way that they can be employed in any type of display and in particular of TN display and IPS display that has been disclosed hitherto.

The examples below serve to illustrate the invention without representing a restriction. In the examples, the melting point T(C,N), the transition from the smectic (S) phase to the nematic (N) phase T(S,N) and the clearing point T(N,I) of a liquid-crystal substance are indicated in degrees Celsius. The various smectic phases are characterised by corresponding suffixes.

The percentages above and below are, unless explicitly stated otherwise, percent by weight, and the physical properties are the values at 20° C., unless explicitly stated otherwise.

All the temperature values indicated in this application are ° C. and all temperature differences are correspondingly differential degrees, unless explicitly stated otherwise.

In the synthesis examples and schemes, the abbreviations have the following meanings:

DAST diethylaminosulfur trifluoride,

DBH dibromodimethylhydantoin,

DEAD diethyl azodicarboxylate,

DIBAL diisobutylaluminium hydride,

MTB ether methyl tert-butyl ether,

NBS N-bromosuccinimide,

Tf trifluoromethanesulfonyl,

THF tetrahydrofuran.

In the present application and in the examples below, the structures of the liquid-crystal compounds are indicated by means of acronyms, the trans-formation into chemical formulae taking place in accordance with Tables A and B below. All radicals $C_nH_{2n+1}$ and $C_mH_{2m+1}$ are straight-chain alkyl radicals having n and m C atoms respectively. The coding in Table B is self-evident. In Table A, only the acronym for the parent structure is indicated. In individual cases, the acronym for the parent structure is followed, separated by a dash, by a code for the substituents $R^1$, $R^2$, $L^1$, $L^2$ and $L^3$:

| Code for $R^1, R^2, L^1, L^2, L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO•m | $OC_nH_{2n+1}$ | $C_mH_{2m+1}$ | H | H | H |
| nmFF | $C_nH_{2n+1}$ | $C_mH_{2m+1}$ | F | H | F |
| nOmFF | $C_nH_{2n+1}$ | $OC_mH_{2m+1}$ | F | H | F |
| nO•mFF | $OC_nH_{2n+1}$ | $C_mH_{2m+1}$ | F | H | F |
| nO•OmFF | $OC_nH_{2n+1}$ | $OC_mH_{2m+1}$ | F | H | F |
| n | $C_nH_{2n+1}$ | CN | H | H | H |
| nN•F | $C_nH_{2n+1}$ | CN | F | H | H |
| nN•F•F | $C_nH_{2n+1}$ | CN | F | F | H |
| nF | $C_nH_{2n+1}$ | F | H | H | H |
| nF•F | $C_nH_{2n+1}$ | F | F | H | H |
| nF•F•F | $C_nH_{2n+1}$ | F | F | F | H |
| nCl | $C_nH_{2n+1}$ | Cl | H | H | H |
| nCl.F | $C_nH_{2n+1}$ | Cl | F | H | H |
| nCl•F•F | $C_nH_{2n+1}$ | Cl | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_3$•F | $C_nH_{2n+1}$ | OCF$_3$ | F | H | H |
| nOCF$_3$•F•F | $C_nH_{2n+1}$ | OCF$_3$ | F | F | H |
| nOCF$_2$ | $C_nH_{2n+1}$ | OCHF$_2$ | H | H | H |
| nOCF$_2$•F•F | $C_nH_{2n+1}$ | OCHF$_2$ | F | F | H |
| nS | $C_nH_{2n+1}$ | NCS | H | H | H |
| rVsN | $C_rH_{2r+1}$—CH=CH—$C_sH_{2s}$— | CN | H | H | H |
| nEsN | $C_rH_{2r+1}$—O—$C_sH_{2s}$— | CN | H | H | H |
| nAm | $C_nH_{2n+1}$ | $COOC_mH_{2m+1}$ | H | H | H |
| nF•Cl | $C_nH_{2n+1}$ | F | Cl | H | H |

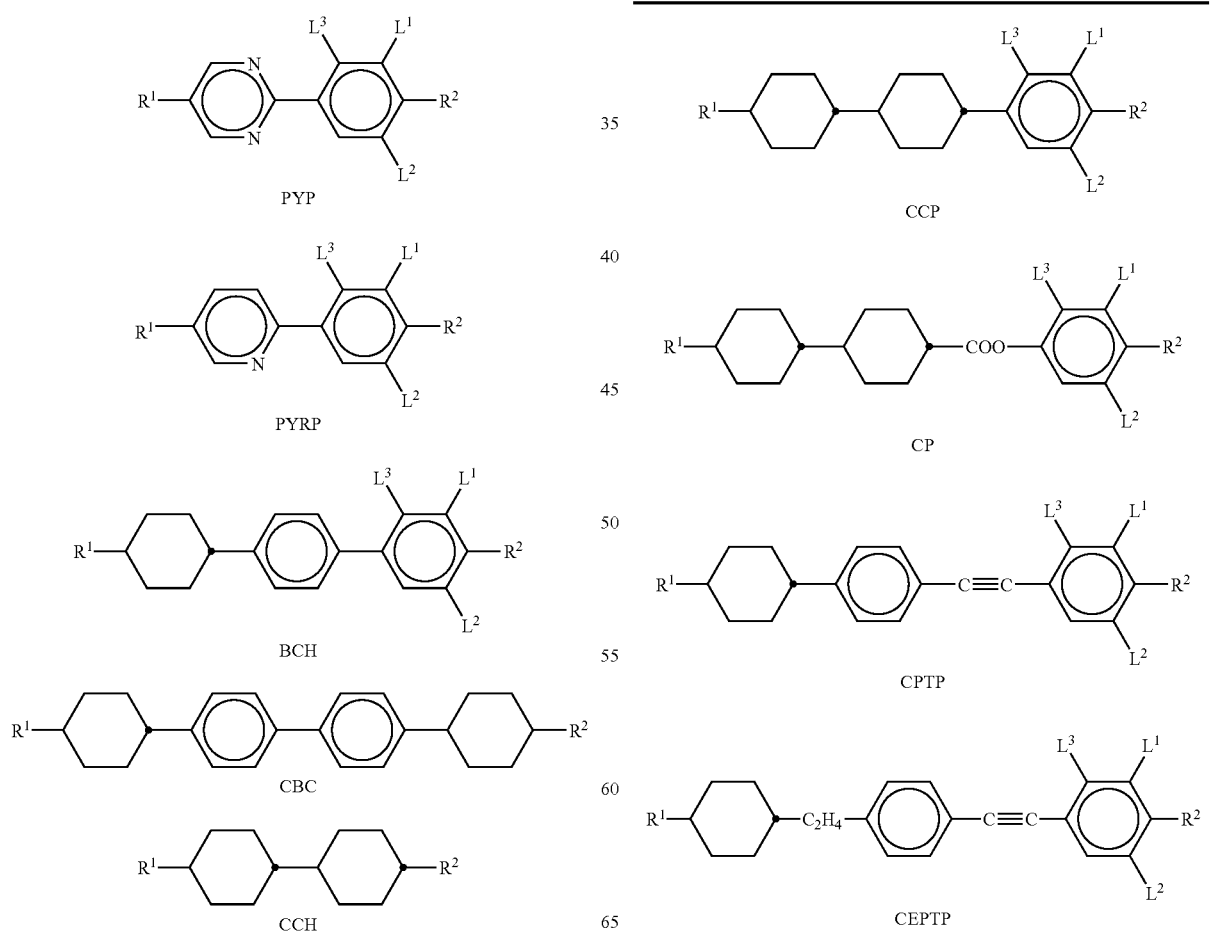

TABLE A

PYP

PYRP

BCH

CBC

CCH

TABLE A-continued

CCP

CP

CPTP

CEPTP

TABLE A-continued
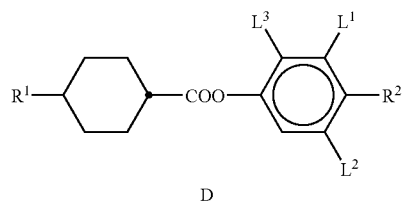
D
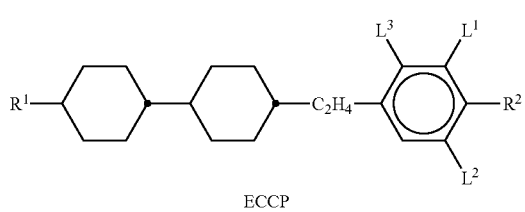
ECCP
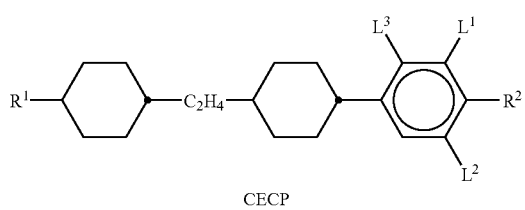
CECP
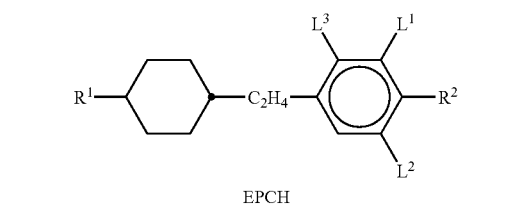
EPCH
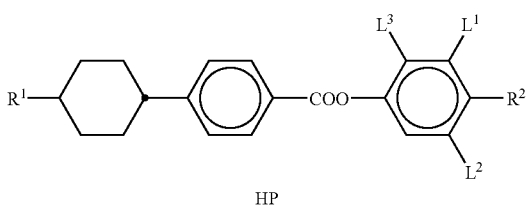
HP
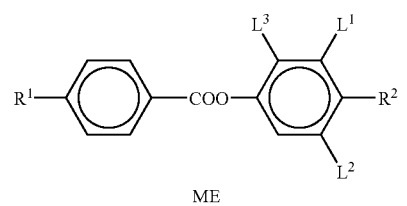
ME
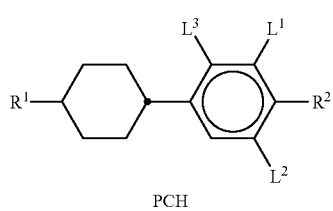
PCH
TABLE A-continued
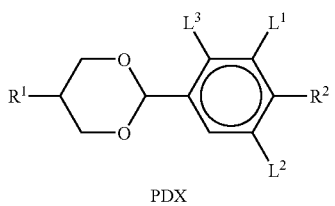
PDX
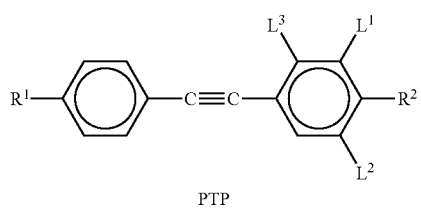
PTP
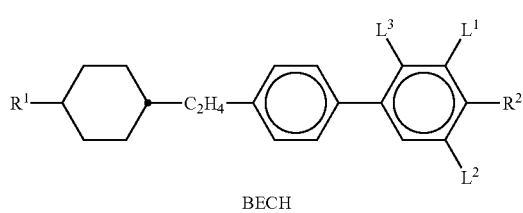
BECH
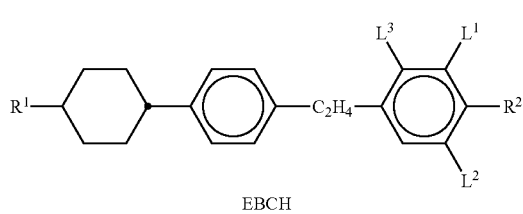
EBCH
CPC
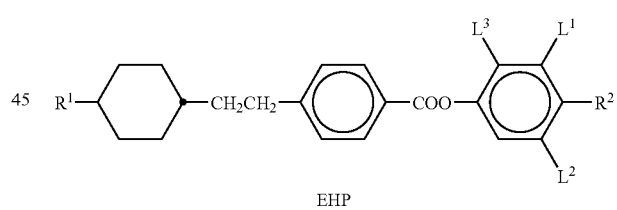
EHP
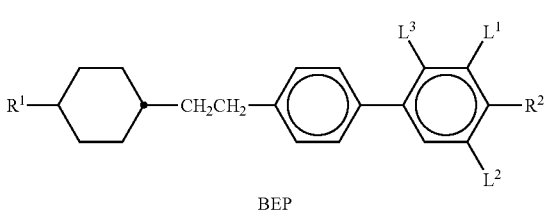
BEP
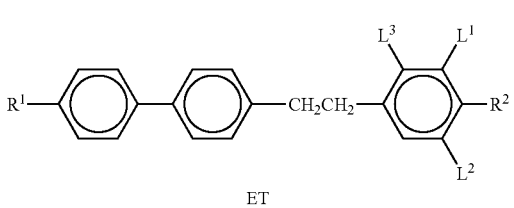
ET TABLE B
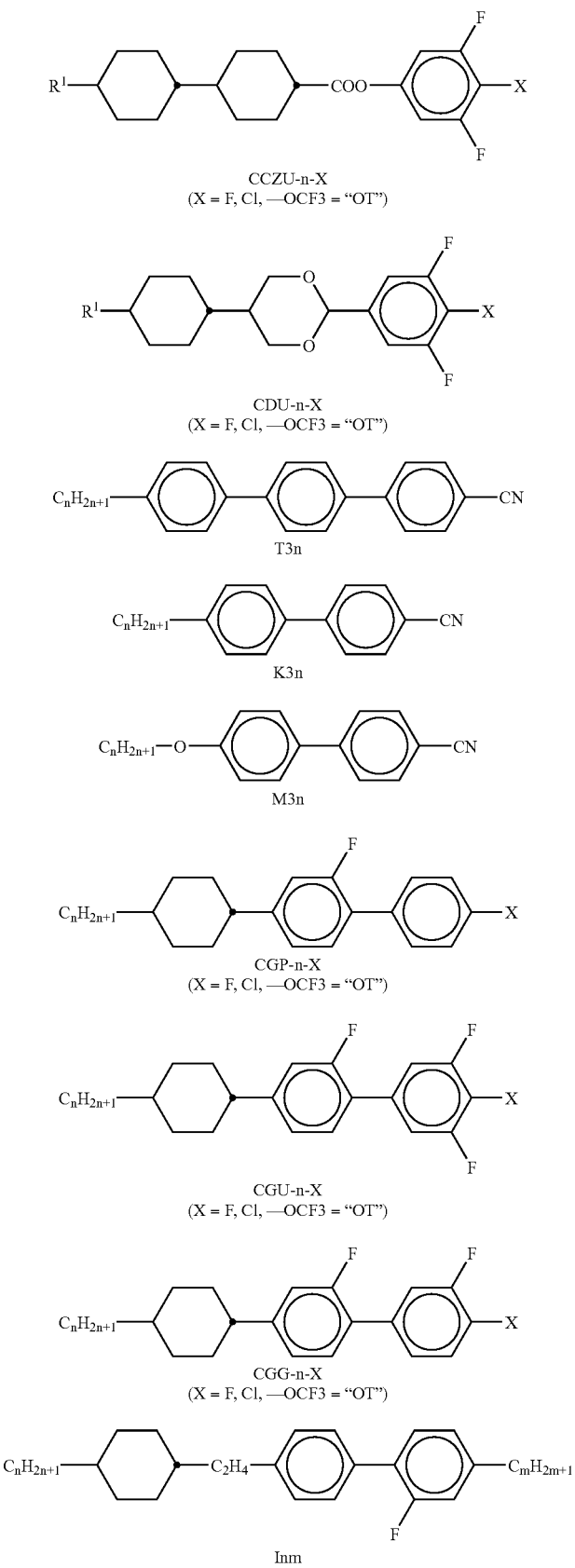

TABLE B-continued
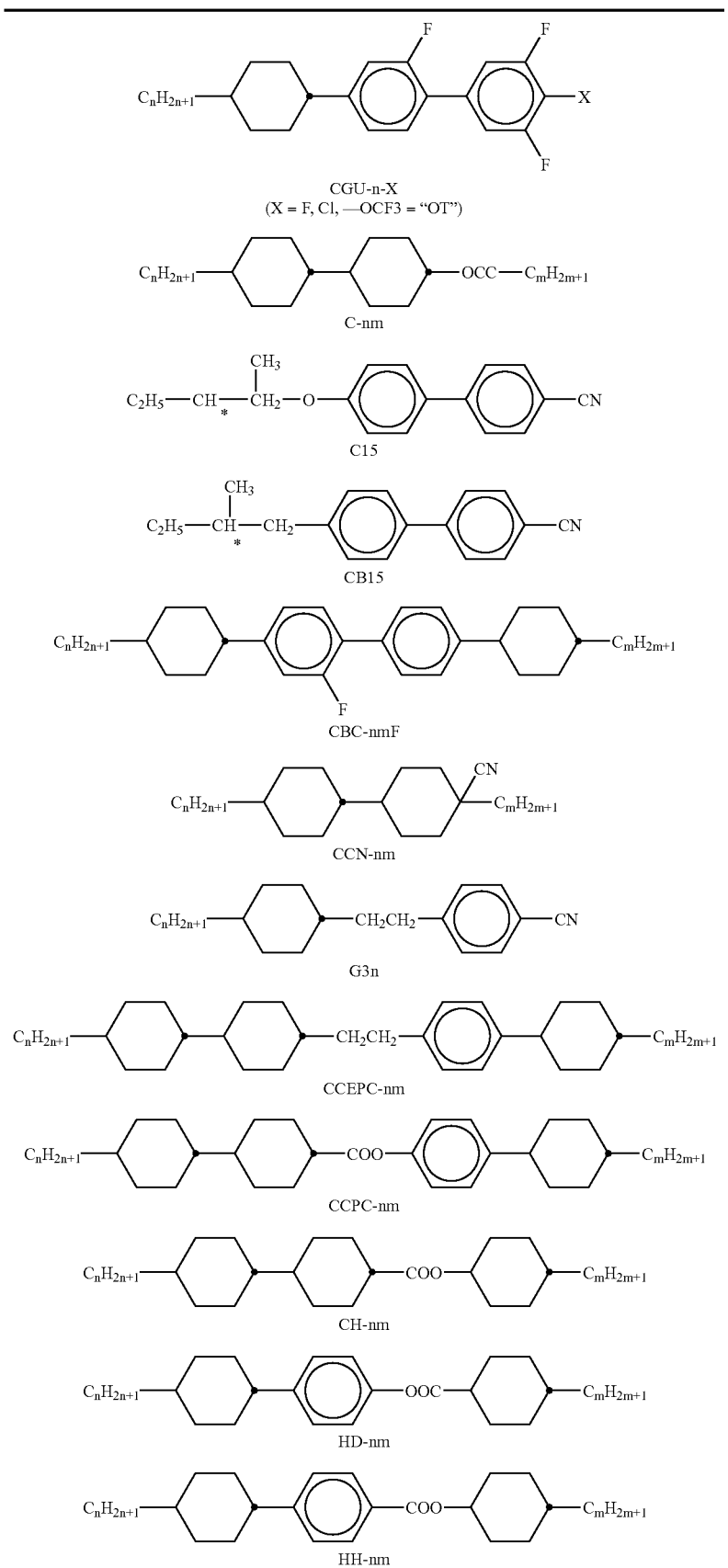

TABLE B-continued
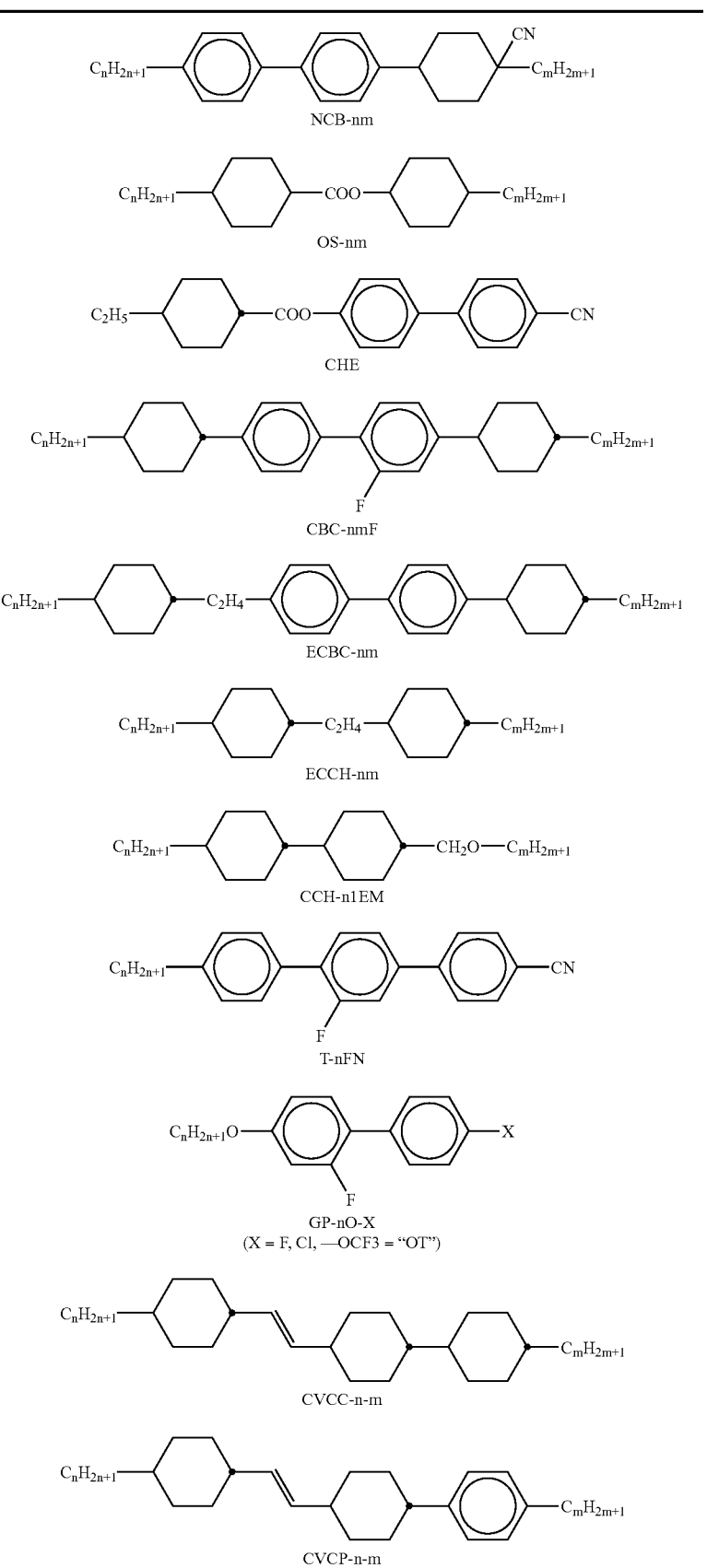

TABLE B-continued
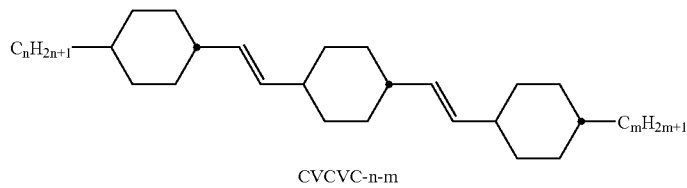
CVCVC-n-m
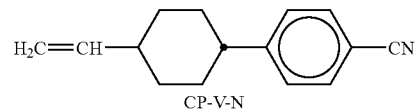
CP-V-N
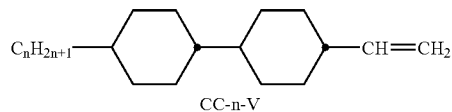
CC-n-V
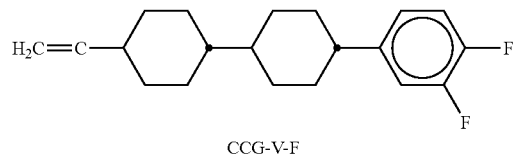
CCG-V-F
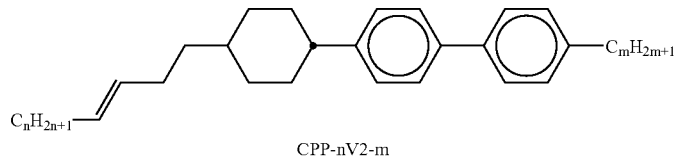
CPP-nV2-m
CCP-V-m
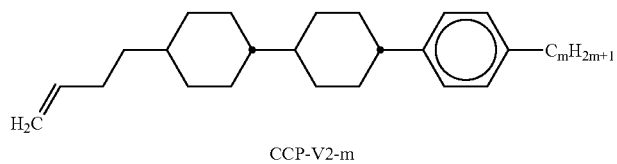
CCP-V2-m
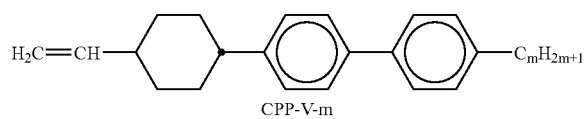
CPP-V-m TABLE B-continued

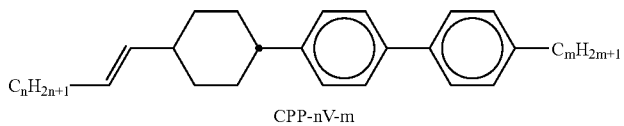
CPP-nV-m

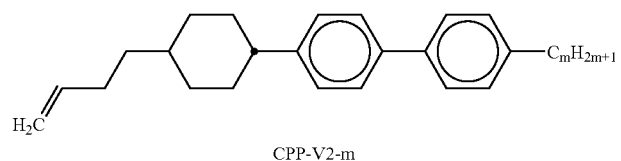
CPP-V2-m

CC-V-V

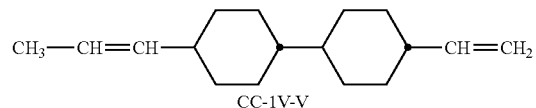
CC-1V-V

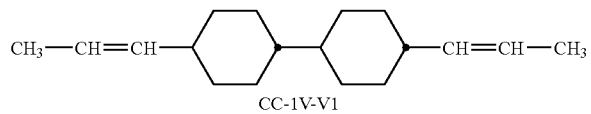
CC-1V-V1

CC-2V-V

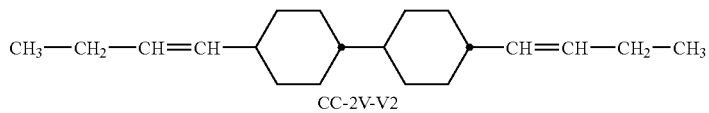
CC-2V-V2

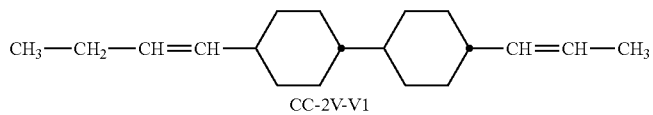
CC-2V-V1

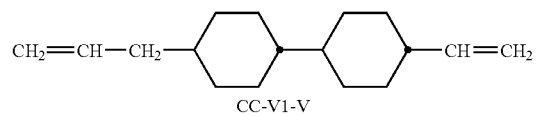
CC-V1-V

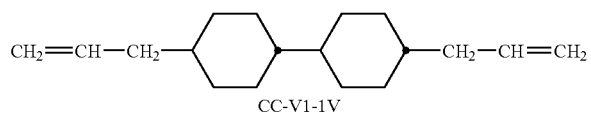
CC-V1-1V

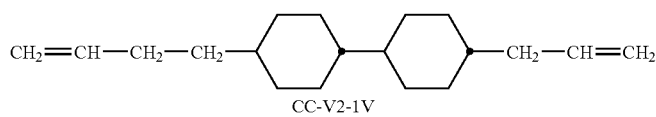
CC-V2-1V

EXAMPLES

The following examples are intended to explain the invention without limiting it. Above and below, percentages are percent by weight. All temperatures are indicated in degrees Celsius. Δn denotes the optical anisotropy (589 nm, 20° C.), Δε the dielectric anisotropy (1 kHz, 20° C.), H.R. the voltage holding ratio (at 100° C., after 5 minutes in the oven, 1 V). $V_{10}$, $V_{50}$ and $V_{90}$ (the threshold voltage, mid-grey voltage and saturation voltage respectively) and $V_0$ (the capacitive threshold voltage) were each determined at 20° C.

SUBSTANCE EXAMPLES

Example 1

(8-Propyl-3-(3,4,5-trifluorophenyl)-7,8,9,10-tetrahydrobenzo[c]-chromen-6-one)

1.1. Preparation of 6-oxo-8-propyl-7,8,9,10-tetrahydro-6H-benzo[c]-chromen-3-yl trifluoromethanesulfonate

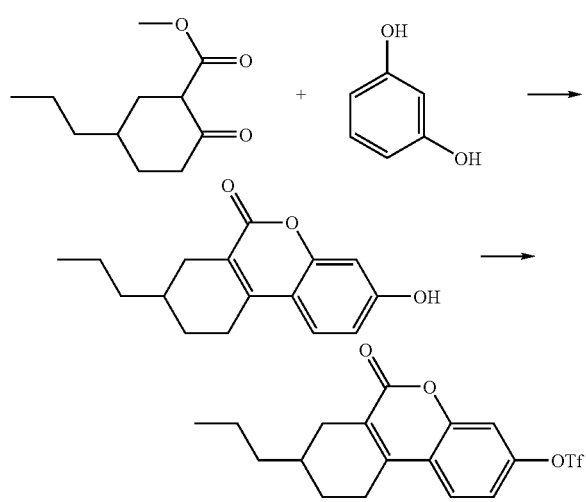

16.6 g (78.5 mmol) of methyl 2-oxo-5-propylcyclohexanecarboxylate, 7.65 g (69.5 mmol) of resorcinol and 5.6 ml (6.1 mmol) of phosphoryl chloride are dissolved in 55 ml of toluene and refluxed for 3 h. After hydrolysis using water, the deposited precipitate is filtered off with suction, washed with toluene and dried.

The 3-hydroxy-8-propyl-7,8,9,10-tetrahydrobenzo[c]chromen-6-one obtained is dissolved in dichloromethane, 29 ml (0.21 mol) of triethylamine are added, and 25.7 ml (0.153 mol) of trifluoromethanesulfonic anhydride are added dropwise at −78° C. The cooling is removed, the batch is stirred at room temp. for 2 h and added to ice-cold 1M hydrochloric acid. The aqueous phase is separated off and extracted with dichloromethane. The combined org. phases are washed with water until neutral and dried over sodium sulfate. Removal of the solvent under reduced pressure gives 6-oxo-8-propyl-7,8,9,10-tetrahydro-6H-benzo[c]chromen-3-yl trifluoromethanesulfonate, which is reacted without further purification.

1.2. Preparation of 8-propyl-3-(3,4,5-trifluorophenyl)-7,8,9,10-tetrahydrobenzo[c]chromen-6-one

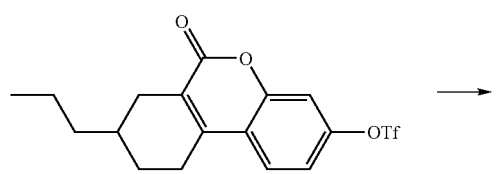

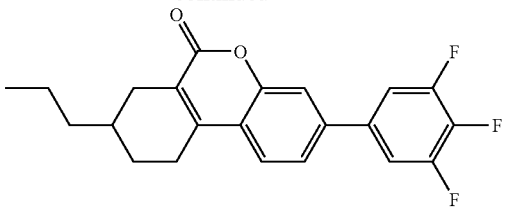

10 g (25.6 mmol) of 6-oxo-8-propyl-7,8,9,10-tetrahydro-6H-benzo[c]-chromen-3-yl trifluoromethanesulfonate, 4.50 g (25.6 mmol) of 3,4,5-trifluorobenzeneboronic acid, 10.6 g (38.4 mmol) of sodium metaborate octahydrate, 360 mg (0.51 mmol) of bis(triphenylphosphine)palladium chloride and 50 µl of hydrazinium hydroxide are dissolved in 15 ml of water and 250 ml of THF, and the mixture is refluxed overnight. Water is added to the batch, which is extracted three times with dichloromethane. The combined org. phases are dried over sodium sulfate, the solvent is removed under reduced pressure, and the residue is filtered through silica gel and recrystallised, giving 8-propyl-3-(3,4,5-trifluorophenyl)-7,8,9,10-tetrahydrobenzo[c]chromen-6-one.

Example 2

(8-Propyl-3-(3,4,5-trifluorophenyl)-6a,7,8,9,10,10a-hexahydro-6H-benzo[c]chromene)

2.1. Preparation of ethyl 5-propyl-2-(3',4',5'-trifluoro-3-hydroxybiphenyl-4-yl)cyclohexanecarboxylate

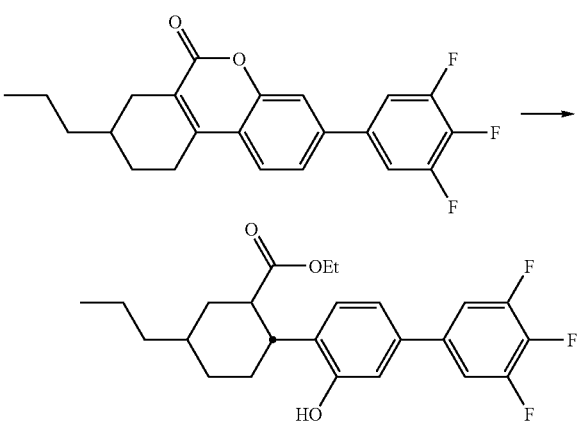

10 g (26.9 mmol) of 8-propyl-3-(3,4,5-trifluorophenyl)-7,8,9,10-tetrahydrobenzo[c]chromen-6-one from Example 1 (1.2.) are dissolved in THF and hydrogenated to cessation in the presence of palladium/active carbon catalyst. The mixture is subsequently filtered, the solvent is removed under reduced pressure, and the residue is dissolved in abs. ethanol and, after addition of 5.5 g (80.7 mmol) of sodium ethoxide, refluxed overnight. After addition of water, the mixture is acidified, the solution is extracted with MTB ether and dried over sodium sulfate. The solvent is removed under reduced pressure, and the crude product is purified by crystallisation, giving ethyl 5-propyl-2-(3',4',5'-trifluoro-3-hydroxybiphenyl-4-yl)cyclohexanecarboxylate.

2.2. Preparation of 8-propyl-3-(3,4,5-trifluorophenyl)-6a,7,8,9,10,10a-hexahydro-6H-benzo[c]chromene

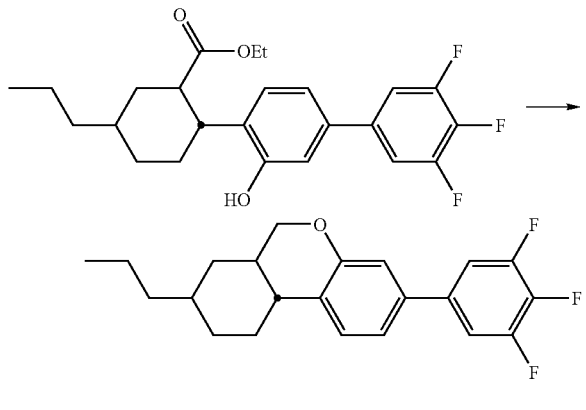

903 mg (23.8 mmol) of lithium aluminium hydride are initially introduced in 20 ml of THF, and a solution of 10 g (23.8 mmol) of ethyl 5-propyl-2-(3',4',5'-trifluoro-3-hydroxybiphenyl-4-yl)cyclohexanecarboxylate in 50 ml of THF is added dropwise with ice-cooling. The cooling is removed, and the batch is stirred at room temp. for 3 h, refluxed for 1 h and added to ice. After acidification using 2M sulfuric acid, the mixture is extracted three times with MTB ether, the combined org. phases are washed with water and dried over sodium sulfate. The solvent is removed under reduced pressure, and the residue is purified by chromatography on silica gel. The 3',4',5'-trifluoro-4-(2-hydroxymethyl-4-propylcyclohexyl)biphenyl-3-ol obtained is dissolved in 100 ml of THF, 6.24 g (23.8 mmol) of triphenylphosphine are added, and a solution of 5.3 g (26.2 mmol) of diisopropyl azodicarboxylate in 50 ml of THF is added dropwise with ice-cooling. The cooling is removed, and the batch is stirred at room temp. overnight. After addition of water, the organic phase is separated off, and the aqueous phase is extracted three times with MTB ether. The combined org. phases are washed with water and saturated sodium chloride solution and dried over sodium sulfate. The solvent is removed under reduced pressure, and the residue is purified by chromatography on silica gel, giving 8-propyl-3-(3,4,5-trifluorophenyl)-6a,7,8,9,10,10a-hexahydro-6H-benzo[c]chromene as colourless crystals.

Examples 3 to 120

Compounds of the formula:

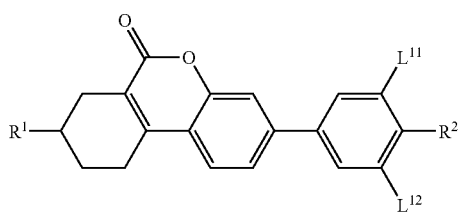

are prepared analogously to Example 1.2.

| No. | $R^1$ | $R^2$ | $L^{11}$ | $R^{12}$ | Phase sequence $\Delta\epsilon^*$ T/° C. | $T^*(N, I)$/ ° C. |
|---|---|---|---|---|---|---|
| 3 | CH$_3$ | F | H | H | | |
| 4 | CH$_3$ | F | F | H | | |
| 5 | CH$_3$ | F | F | F | | |
| 6 | CH$_3$ | Cl | H | H | | |
| 7 | CH$_3$ | Cl | F | H | | |
| 8 | CH$_3$ | Cl | F | F | | |
| 9 | CH$_3$ | CF$_3$ | H | H | | |
| 10 | CH$_3$ | CF$_3$ | F | H | | |
| 11 | CH$_3$ | CF$_3$ | F | F | | |
| 12 | CH$_3$ | OCF$_3$ | H | H | | |
| 13 | CH$_3$ | OCF$_3$ | F | H | | |
| 14 | CH$_3$ | OCF$_3$ | F | F | | |
| 15 | CH$_3$ | CN | H | H | | |
| 16 | CH$_3$ | CN | F | H | | |
| 17 | CH$_3$ | CN | F | F | | |
| 18 | C$_2$H$_5$ | F | H | H | | |
| 19 | C$_2$H$_5$ | F | F | H | | |
| 20 | C$_2$H$_5$ | F | F | F | | |
| 21 | C$_2$H$_5$ | Cl | H | H | | |
| 22 | C$_2$H$_5$ | Cl | F | H | | |
| 23 | C$_2$H$_5$ | Cl | F | F | | |
| 24 | C$_2$H$_5$ | CF$_3$ | H | H | | |
| 25 | C$_2$H$_5$ | CF$_3$ | F | H | | |
| 26 | C$_2$H$_5$ | CF$_3$ | F | F | | |
| 27 | C$_2$H$_5$ | OCF$_3$ | H | H | | |
| 28 | C$_2$H$_5$ | OCF$_3$ | F | H | | |
| 29 | C$_2$H$_5$ | OCF$_3$ | F | F | | |
| 30 | C$_2$H$_5$ | CN | H | H | | |
| 31 | C$_2$H$_5$ | CN | F | H | | |
| 32 | C$_2$H$_5$ | CN | F | F | | |
| 33 | n-C$_3$H$_7$ | F | H | H | | |
| 34 | n-C$_3$H$_7$ | F | F | H | | |
| 1.2 | n-C$_3$H$_7$ | F | F | F | | |
| 35 | n-C$_3$H$_7$ | Cl | H | H | | |
| 36 | n-C$_3$H$_7$ | Cl | F | H | | |
| 37 | n-C$_3$H$_7$ | Cl | F | F | | |
| 38 | n-C$_3$H$_7$ | CF$_3$ | H | H | | |
| 39 | n-C$_3$H$_7$ | CF$_3$ | F | H | | |
| 40 | n-C$_3$H$_7$ | CF$_3$ | F | F | | |
| 41 | n-C$_3$H$_7$ | OCF$_3$ | H | H | | |
| 42 | n-C$_3$H$_7$ | OCF$_3$ | F | H | | |
| 43 | n-C$_3$H$_7$ | OCF$_3$ | F | F | | |
| 44 | n-C$_3$H$_7$ | CN | H | H | | |
| 45 | n-C$_3$H$_7$ | CN | F | H | | |
| 46 | n-C$_3$H$_7$ | CN | F | F | | |
| 47 | n-C$_4$H$_9$ | F | H | H | | |
| 48 | n-C$_4$H$_9$ | F | F | H | | |
| 49 | n-C$_4$H$_9$ | F | F | F | | |
| 50 | n-C$_4$H$_9$ | Cl | H | H | | |
| 51 | n-C$_4$H$_9$ | Cl | F | H | | |
| 52 | n-C$_4$H$_9$ | Cl | F | F | | |
| 53 | n-C$_4$H$_9$ | CF$_3$ | H | H | | |
| 54 | n-C$_4$H$_9$ | CF$_3$ | F | H | | |
| 55 | n-C$_4$H$_9$ | CF$_3$ | F | F | | |
| 56 | n-C$_4$H$_9$ | OCF$_3$ | H | H | | |
| 57 | n-C$_4$H$_9$ | OCF$_3$ | F | H | | |
| 58 | n-C$_4$H$_9$ | OCF$_3$ | F | F | | |
| 59 | n-C$_4$H$_9$ | CN | H | H | | |
| 60 | n-C$_4$H$_9$ | CN | F | H | | |
| 61 | n-C$_4$H$_9$ | CN | F | F | | |
| 62 | CH$_3$O | F | H | H | | |
| 63 | CH$_3$O | F | F | H | | |
| 64 | CH$_3$O | F | F | F | | |
| 65 | CH$_3$O | Cl | H | H | | |
| 66 | CH$_3$O | Cl | F | H | | |
| 67 | CH$_3$O | Cl | F | F | | |
| 68 | CH$_3$O | CF$_3$ | H | H | | |
| 69 | CH$_3$O | CF$_3$ | F | H | | |
| 70 | CH$_3$O | CF$_3$ | F | F | | |
| 71 | CH$_3$O | OCF$_3$ | H | H | | |
| 72 | CH$_3$O | OCF$_3$ | F | H | | |
| 73 | CH$_3$O | OCF$_3$ | F | F | | |
| 74 | CH$_3$O | CN | H | H | | |
| 75 | CH$_3$O | CN | F | H | | |
| 76 | CH$_3$O | CN | F | F | | |
| 77 | C$_2$H$_5$O | F | H | H | | |

| No. | $R^1$ | $R^2$ | $L^{11}$ | $R^{12}$ | Phase sequence $\Delta\epsilon^*$ T/° C. | T*(N, I)/ ° C. |
|---|---|---|---|---|---|---|
| 78 | $C_2H_5O$ | F | F | H | | |
| 79 | $C_2H_5O$ | F | F | F | | |
| 80 | $C_2H_5O$ | Cl | H | H | | |
| 81 | $C_2H_5O$ | Cl | F | H | | |
| 82 | $C_2H_5O$ | Cl | F | F | | |
| 83 | $C_2H_5O$ | $CF_3$ | H | H | | |
| 84 | $C_2H_5O$ | $CF_3$ | F | H | | |
| 85 | $C_2H_5O$ | $CF_3$ | F | F | | |
| 86 | $C_2H_5O$ | $OCF_3$ | H | H | | |
| 87 | $C_2H_5O$ | $OCF_3$ | F | H | | |
| 88 | $C_2H_5O$ | $OCF_3$ | F | F | | |
| 89 | $C_2H_5O$ | CN | H | H | | |
| 90 | $C_2H_5O$ | CN | F | H | | |
| 91 | $C_2H_5O$ | CN | F | F | | |
| 92 | $CH_2=CH$ | F | H | H | | |
| 93 | $CH_2=CH$ | F | F | H | | |
| 94 | $CH_2=CH$ | F | F | F | | |
| 95 | $CH_2=CH$ | Cl | H | H | | |
| 96 | $CH_2=CH$ | Cl | F | H | | |
| 97 | $CH_2=CH$ | Cl | F | F | | |
| 98 | $CH_2=CH$ | $CF_3$ | H | H | | |
| 99 | $CH_2=CH$ | $CF_3$ | F | H | | |
| 100 | $CH_2=CH$ | $CF_3$ | F | F | | |
| 101 | $CH_2=CH$ | $OCF_3$ | H | H | | |
| 102 | $CH_2=CH$ | $OCF_3$ | F | H | | |
| 103 | $CH_2=CH$ | $OCF_3$ | F | F | | |
| 104 | $CH_2=CH$ | CN | H | H | | |
| 105 | $CH_2=CH$ | CN | F | H | | |
| 106 | $CH_2=CH$ | CN | F | F | | |
| 107 | $CH_2=CH-O$ | F | H | H | | |
| 108 | $CH_2=CH-O$ | F | F | H | | |
| 109 | $CH_2=CH-O$ | F | F | F | | |
| 110 | $CH_2=CH-O$ | Cl | H | H | | |
| 111 | $CH_2=CH-O$ | Cl | F | H | | |
| 112 | $CH_2=CH-O$ | Cl | F | F | | |
| 113 | $CH_2=CH-O$ | $CF_3$ | H | H | | |
| 114 | $CH_2=CH-O$ | $CF_3$ | F | H | | |
| 115 | $CH_2=CH-O$ | $CF_3$ | F | F | | |
| 116 | $CH_2=CH-O$ | $OCF_3$ | H | H | | |
| 117 | $CH_2=CH-O$ | $OCF_3$ | F | H | | |
| 118 | $CH_2=CH-O$ | $OCF_3$ | F | F | | |
| 119 | $CH_2=CH-O$ | CN | H | H | | |
| 120 | $CH_2=CH-O$ | CN | F | H | | |
| 121 | $CH_2=CH-O$ | CN | F | F | | |

Note:
*values extrapolated from 10% solution in ZLI-4792.

Examples 122 to 240

Compounds of the formula:

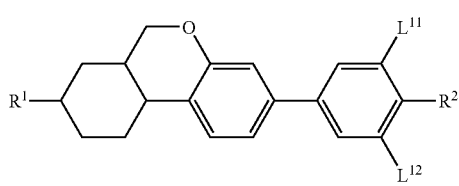

are prepared analogously to Example 2.2.

| No. | $R^1$ | $R^2$ | $L^{11}$ | $R^{12}$ | Phase sequence $\Delta\epsilon^*$ T/° C. | T*(N, I)/ ° C. |
|---|---|---|---|---|---|---|
| 122 | $CH_3$ | F | H | H | | |
| 123 | $CH_3$ | F | F | H | | |
| 124 | $CH_3$ | F | F | F | | |
| 125 | $CH_3$ | Cl | H | H | | |
| 121 | $CH_3$ | Cl | F | H | | |
| 126 | $CH_3$ | Cl | F | F | | |
| 127 | $CH_3$ | $CF_3$ | H | H | | |
| 128 | $CH_3$ | $CF_3$ | F | H | | |
| 129 | $CH_3$ | $CF_3$ | F | F | | |
| 130 | $CH_3$ | $OCF_3$ | H | H | | |
| 131 | $CH_3$ | $OCF_3$ | F | H | | |
| 132 | $CH_3$ | $OCF_3$ | F | F | | |
| 133 | $CH_3$ | CN | H | H | | |
| 134 | $CH_3$ | CN | F | H | | |
| 135 | $CH_3$ | CN | F | F | | |
| 136 | $C_2H_5$ | F | H | H | | |
| 137 | $C_2H_5$ | F | F | H | | |
| 138 | $C_2H_5$ | F | F | F | | |
| 139 | $C_2H_5$ | Cl | H | H | | |
| 140 | $C_2H_5$ | Cl | F | H | | |
| 141 | $C_2H_5$ | Cl | F | F | | |
| 142 | $C_2H_5$ | $CF_3$ | H | H | | |
| 143 | $C_2H_5$ | $CF_3$ | F | H | | |
| 144 | $C_2H_5$ | $CF_3$ | F | F | | |
| 145 | $C_2H_5$ | $OCF_3$ | H | H | | |
| 146 | $C_2H_5$ | $OCF_3$ | F | H | | |
| 147 | $C_2H_5$ | $OCF_3$ | F | F | | |
| 148 | $C_2H_5$ | CN | H | H | | |
| 149 | $C_2H_5$ | CN | F | H | | |
| 150 | $C_2H_5$ | CN | F | F | | |
| 151 | $n-C_3H_7$ | F | H | H | | |
| 152 | $n-C_3H_7$ | F | F | H | | |
| 2.2 | $n-C_3H_7$ | F | F | F | | |
| 153 | $n-C_3H_7$ | Cl | H | H | | |
| 154 | $n-C_3H_7$ | Cl | F | H | | |
| 155 | $n-C_3H_7$ | Cl | F | F | | |
| 156 | $n-C_3H_7$ | $CF_3$ | H | H | | |
| 157 | $n-C_3H_7$ | $CF_3$ | F | H | | |
| 158 | $n-C_3H_7$ | $CF_3$ | F | F | | |
| 159 | $n-C_3H_7$ | $OCF_3$ | H | H | | |
| 160 | $n-C_3H_7$ | $OCF_3$ | F | H | | |
| 161 | $n-C_3H_7$ | $OCF_3$ | F | F | | |
| 162 | $n-C_3H_7$ | CN | H | H | | |
| 163 | $n-C_3H_7$ | CN | F | H | | |
| 164 | $n-C_3H_7$ | CN | F | F | | |
| 165 | $n-C_4H_9$ | F | H | H | | |
| 166 | $n-C_4H_9$ | F | F | H | | |
| 167 | $n-C_4H_9$ | F | F | F | | |
| 168 | $n-C_4H_9$ | Cl | H | H | | |
| 169 | $n-C_4H_9$ | Cl | F | H | | |
| 170 | $n-C_4H_9$ | Cl | F | F | | |
| 171 | $n-C_4H_9$ | $CF_3$ | H | H | | |
| 172 | $n-C_4H_9$ | $CF_3$ | F | H | | |
| 173 | $n-C_4H_9$ | $CF_3$ | F | F | | |
| 174 | $n-C_4H_9$ | $OCF_3$ | H | H | | |
| 175 | $n-C_4H_9$ | $OCF_3$ | F | H | | |
| 176 | $n-C_4H_9$ | $OCF_3$ | F | F | | |
| 177 | $n-C_4H_9$ | CN | H | H | | |
| 178 | $n-C_4H_9$ | CN | F | H | | |
| 179 | $n-C_4H_9$ | CN | F | F | | |
| 180 | $CH_3O$ | F | H | H | | |
| 181 | $CH_3O$ | F | F | H | | |
| 182 | $CH_3O$ | F | F | F | | |
| 183 | $CH_3O$ | Cl | H | H | | |
| 184 | $CH_3O$ | Cl | F | H | | |
| 185 | $CH_3O$ | Cl | F | F | | |
| 186 | $CH_3O$ | $CF_3$ | H | H | | |
| 187 | $CH_3O$ | $CF_3$ | F | H | | |
| 188 | $CH_3O$ | $CF_3$ | F | F | | |
| 189 | $CH_3O$ | $OCF_3$ | H | H | | |
| 190 | $CH_3O$ | $OCF_3$ | F | H | | |
| 191 | $CH_3O$ | $OCF_3$ | F | F | | |
| 192 | $CH_3O$ | CN | H | H | | |
| 193 | $CH_3O$ | CN | F | H | | |
| 194 | $CH_3O$ | CN | F | F | | |
| 195 | $C_2H_5O$ | F | H | H | | |
| 196 | $C_2H_5O$ | F | F | H | | |
| 197 | $C_2H_5O$ | F | F | F | | |
| 198 | $C_2H_5O$ | Cl | H | H | | |
| 199 | $C_2H_5O$ | Cl | F | H | | |

-continued

| No. | R¹ | R² | L¹¹ | R¹² | Phase sequence Δε* T/° C. | T*(N, I)/° C. |
|---|---|---|---|---|---|---|
| 201 | C₂H₅O | Cl | F | F | | |
| 202 | C₂H₅O | CF₃ | H | H | | |
| 203 | C₂H₅O | CF₃ | F | H | | |
| 204 | C₂H₅O | CF₃ | F | F | | |
| 205 | C₂H₅O | OCF₃ | H | H | | |
| 206 | C₂H₅O | OCF₃ | F | H | | |
| 207 | C₂H₅O | OCF₃ | F | F | | |
| 208 | C₂H₅O | CN | H | H | | |
| 209 | C₂H₅O | CN | F | H | | |
| 210 | C₂H₅O | CN | F | F | | |
| 211 | CH₂=CH | F | H | H | | |
| 212 | CH₂=CH | F | F | H | | |
| 213 | CH₂=CH | F | F | F | | |
| 214 | CH₂=CH | Cl | H | H | | |
| 215 | CH₂=CH | Cl | F | H | | |
| 216 | CH₂=CH | Cl | F | F | | |
| 217 | CH₂=CH | CF₃ | H | H | | |
| 218 | CH₂=CH | CF₃ | F | H | | |
| 219 | CH₂=CH | CF₃ | F | F | | |
| 220 | CH₂=CH | OCF₃ | H | H | | |
| 221 | CH₂=CH | OCF₃ | F | H | | |
| 222 | CH₂=CH | OCF₃ | F | F | | |
| 223 | CH₂=CH | CN | H | H | | |
| 224 | CH₂=CH | CN | F | H | | |
| 225 | CH₂=CH | CN | F | F | | |
| 226 | CH₂=CH—O | F | H | H | | |
| 227 | CH₂=CH—O | F | F | H | | |
| 228 | CH₂=CH—O | F | F | F | | |
| 229 | CH₂=CH—O | Cl | H | H | | |
| 230 | CH₂=CH—O | Cl | F | H | | |
| 231 | CH₂=CH—O | Cl | F | F | | |
| 232 | CH₂=CH—O | CF₃ | H | H | | |
| 233 | CH₂=CH—O | CF₃ | F | H | | |
| 234 | CH₂=CH—O | CF₃ | F | F | | |
| 235 | CH₂=CH—O | OCF₃ | H | H | | |
| 236 | CH₂=CH—O | OCF₃ | F | H | | |
| 237 | CH₂=CH—O | OCF₃ | F | F | | |
| 238 | CH₂=CH—O | CN | H | H | | |
| 239 | CH₂=CH—O | CN | F | H | | |
| 240 | CH₂=CH—O | CN | F | F | | |

Note:
*values extrapolated from 10% solution in ZLI-4792.

Examples 241 to 359

Compounds of the formula

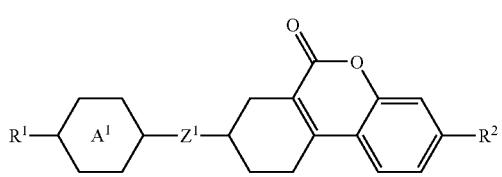

in which

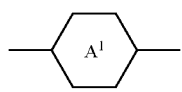

denotes

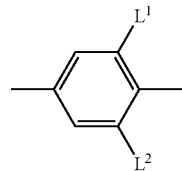

and $Z^1$ denotes a single bond, are prepared analogously to Example 1.2.

| No. | R¹ | R² | L¹¹ | R¹² | Phase sequence Δε* T/° C. | T*(N, I)/° C. |
|---|---|---|---|---|---|---|
| 241 | CH₃ | F | H | H | | |
| 242 | CH₃ | F | F | H | | |
| 243 | CH₃ | F | F | F | | |
| 244 | CH₃ | Cl | H | H | | |
| 245 | CH₃ | Cl | F | H | | |
| 246 | CH₃ | Cl | F | F | | |
| 247 | CH₃ | CF₃ | H | H | | |
| 248 | CH₃ | CF₃ | F | H | | |
| 249 | CH₃ | CF₃ | F | F | | |
| 250 | CH₃ | OCF₃ | H | H | | |
| 251 | CH₃ | OCF₃ | F | H | | |
| 252 | CH₃ | OCF₃ | F | F | | |
| 253 | CH₃ | CN | H | H | | |
| 254 | CH₃ | CN | F | H | | |
| 255 | CH₃ | CN | F | F | | |
| 256 | C₂H₅ | F | H | H | | |
| 257 | C₂H₅ | F | F | H | | |
| 258 | C₂H₅ | F | F | F | | |
| 259 | C₂H₅ | Cl | H | H | | |
| 260 | C₂H₅ | Cl | F | H | | |
| 261 | C₂H₅ | Cl | F | F | | |
| 262 | C₂H₅ | CF₃ | H | H | | |
| 263 | C₂H₅ | CF₃ | F | H | | |
| 264 | C₂H₅ | CF₃ | F | F | | |
| 265 | C₂H₅ | OCF₃ | H | H | | |
| 266 | C₂H₅ | OCF₃ | F | H | | |
| 267 | C₂H₅ | OCF₃ | F | F | | |
| 268 | C₂H₅ | CN | H | H | | |
| 269 | C₂H₅ | CN | F | H | | |
| 270 | C₂H₅ | CN | F | F | | |
| 271 | n-C₃H₇ | F | H | H | | |
| 272 | n-C₃H₇ | F | F | H | | |
| 273 | n-C₃H₇ | F | F | F | | |
| 274 | n-C₃H₇ | Cl | H | H | | |
| 275 | n-C₃H₇ | Cl | F | H | | |
| 276 | n-C₃H₇ | Cl | F | F | | |
| 277 | n-C₃H₇ | CF₃ | H | H | | |
| 278 | n-C₃H₇ | CF₃ | F | H | | |
| 279 | n-C₃H₇ | CF₃ | F | F | | |
| 280 | n-C₃H₇ | OCF₃ | H | H | | |
| 281 | n-C₃H₇ | OCF₃ | F | H | | |
| 282 | n-C₃H₇ | OCF₃ | F | F | | |
| 283 | n-C₃H₇ | CN | H | H | | |
| 284 | n-C₃H₇ | CN | F | H | | |
| 285 | n-C₃H₇ | CN | F | F | | |
| 286 | n-C₄H₉ | F | H | H | | |
| 287 | n-C₄H₉ | F | F | H | | |
| 288 | n-C₄H₉ | F | F | F | | |
| 289 | n-C₄H₉ | Cl | H | H | | |
| 290 | n-C₄H₉ | Cl | F | H | | |
| 291 | n-C₄H₉ | Cl | F | F | | |
| 292 | n-C₄H₉ | CF₃ | H | H | | |
| 293 | n-C₄H₉ | CF₃ | F | H | | |
| 294 | n-C₄H₉ | CF₃ | F | F | | |
| 295 | n-C₄H₉ | OCF₃ | H | H | | |
| 296 | n-C₄H₉ | OCF₃ | F | H | | |
| 297 | n-C₄H₉ | OCF₃ | F | F | | |

-continued

| No. | R¹ | R² | L¹¹ | R¹² | Phase sequence T/° C. | Δε* | T*(N, I)/ ° C. |
|---|---|---|---|---|---|---|---|
| 298 | n-C₄H₉ | CN | H | H | | | |
| 299 | n-C₄H₉ | CN | F | H | | | |
| 300 | n-C₄H₉ | CN | F | F | | | |
| 300 | CH₃O | F | H | H | | | |
| 302 | CH₃O | F | F | H | | | |
| 303 | CH₃O | F | F | F | | | |
| 304 | CH₃O | Cl | H | H | | | |
| 305 | CH₃O | Cl | F | H | | | |
| 306 | CH₃O | Cl | F | F | | | |
| 307 | CH₃O | CF₃ | H | H | | | |
| 308 | CH₃O | CF₃ | F | H | | | |
| 309 | CH₃O | CF₃ | F | F | | | |
| 310 | CH₃O | OCF₃ | H | H | | | |
| 311 | CH₃O | OCF₃ | F | H | | | |
| 312 | CH₃O | OCF₃ | F | F | | | |
| 313 | CH₃O | CN | H | H | | | |
| 314 | CH₃O | CN | F | H | | | |
| 315 | CH₃O | CN | F | F | | | |
| 316 | C₂H₅O | F | H | H | | | |
| 317 | C₂H₅O | F | F | H | | | |
| 318 | C₂H₅O | F | F | F | | | |
| 319 | C₂H₅O | Cl | H | H | | | |
| 320 | C₂H₅O | Cl | F | H | | | |
| 241 | C₂H₅O | Cl | F | F | | | |
| 321 | C₂H₅O | CF₃ | H | H | | | |
| 322 | C₂H₅O | CF₃ | F | H | | | |
| 323 | C₂H₅O | CF₃ | F | F | | | |
| 324 | C₂H₅O | OCF₃ | H | H | | | |
| 325 | C₂H₅O | OCF₃ | F | H | | | |
| 326 | C₂H₅O | OCF₃ | F | F | | | |
| 327 | C₂H₅O | CN | H | H | | | |
| 328 | C₂H₅O | CN | F | H | | | |
| 329 | C₂H₅O | CN | F | F | | | |
| 330 | CH₂=CH | F | H | H | | | |
| 331 | CH₂=CH | F | F | H | | | |
| 332 | CH₂=CH | F | F | F | | | |
| 333 | CH₂=CH | Cl | H | H | | | |
| 334 | CH₂=CH | Cl | F | H | | | |
| 335 | CH₂=CH | Cl | F | F | | | |
| 336 | CH₂=CH | CF₃ | H | H | | | |
| 337 | CH₂=CH | CF₃ | F | H | | | |
| 338 | CH₂=CH | CF₃ | F | F | | | |
| 339 | CH₂=CH | OCF₃ | H | H | | | |
| 340 | CH₂=CH | OCF₃ | F | H | | | |
| 341 | CH₂=CH | OCF₃ | F | F | | | |
| 342 | CH₂=CH | CN | H | H | | | |
| 343 | CH₂=CH | CN | F | H | | | |
| 344 | CH₂=CH | CN | F | F | | | |
| 345 | CH₂=CH—O | F | H | H | | | |
| 346 | CH₂=CH—O | F | F | H | | | |
| 347 | CH₂=CH—O | F | F | F | | | |
| 348 | CH₂=CH—O | Cl | H | H | | | |
| 349 | CH₂=CH—O | Cl | F | H | | | |
| 350 | CH₂=CH—O | Cl | F | F | | | |
| 351 | CH₂=CH—O | CF₃ | H | H | | | |
| 352 | CH₂=CH—O | CF₃ | F | H | | | |
| 353 | CH₂=CH—O | CF₃ | F | F | | | |
| 354 | CH₂=CH—O | OCF₃ | H | H | | | |
| 355 | CH₂=CH—O | OCF₃ | F | H | | | |
| 356 | CH₂=CH—O | OCF₃ | F | F | | | |
| 357 | CH₂=CH—O | CN | H | H | | | |
| 358 | CH₂=CH—O | CN | F | H | | | |
| 359 | CH₂=CH—O | CN | F | F | | | |

Note:
*values extrapolated from 10% solution in ZLI-4792.

Examples 360 to 479

Compounds of the formula

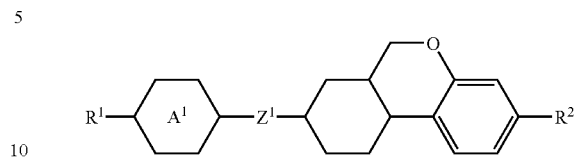

in which

denotes

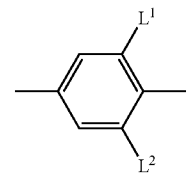

and
$Z^1$ denotes a single bond,
are prepared analogously to Example 2.2.

| No. | R¹ | R² | L¹¹ | R¹² | Phase sequence T/° C. | Δε* | T*(N, I)/ ° C. |
|---|---|---|---|---|---|---|---|
| 360 | CH₃ | F | H | H | | | |
| 361 | CH₃ | F | F | H | | | |
| 362 | CH₃ | F | F | F | | | |
| 363 | CH₃ | Cl | H | H | | | |
| 364 | CH₃ | Cl | F | H | | | |
| 365 | CH₃ | Cl | F | F | | | |
| 366 | CH₃ | CF₃ | H | H | | | |
| 367 | CH₃ | CF₃ | F | H | | | |
| 368 | CH₃ | CF₃ | F | F | | | |
| 369 | CH₃ | OCF₃ | H | H | | | |
| 370 | CH₃ | OCF₃ | F | H | | | |
| 371 | CH₃ | OCF₃ | F | F | | | |
| 372 | CH₃ | CN | H | H | | | |
| 373 | CH₃ | CN | F | H | | | |
| 374 | CH₃ | CN | F | F | | | |
| 375 | C₂H₅ | F | H | H | | | |
| 376 | C₂H₅ | F | F | H | | | |
| 377 | C₂H₅ | F | F | F | | | |
| 378 | C₂H₅ | Cl | H | H | | | |
| 379 | C₂H₅ | Cl | F | H | | | |
| 380 | C₂H₅ | Cl | F | F | | | |
| 381 | C₂H₅ | CF₃ | H | H | | | |
| 382 | C₂H₅ | CF₃ | F | H | | | |
| 383 | C₂H₅ | CF₃ | F | F | | | |
| 384 | C₂H₅ | OCF₃ | H | H | | | |
| 385 | C₂H₅ | OCF₃ | F | H | | | |
| 386 | C₂H₅ | OCF₃ | F | F | | | |
| 387 | C₂H₅ | CN | H | H | | | |
| 388 | C₂H₅ | CN | F | H | | | |
| 389 | C₂H₅ | CN | F | F | | | |
| 390 | n-C₃H₇ | F | H | H | | | |
| 391 | n-C₃H₇ | F | F | H | | | |
| 392 | n-C₃H₇ | F | F | F | | | |
| 393 | n-C₃H₇ | Cl | H | H | | | |

-continued

| No. | R¹ | R² | L¹¹ | R¹² | Phase sequence Δε* T/° C. | T*(N, I)/ ° C. |
|---|---|---|---|---|---|---|
| 394 | n-C₃H₇ | Cl | F | H | | |
| 395 | n-C₃H₇ | Cl | F | F | | |
| 396 | n-C₃H₇ | CF₃ | H | H | | |
| 397 | n-C₃H₇ | CF₃ | F | H | | |
| 398 | n-C₃H₇ | CF₃ | F | F | | |
| 399 | n-C₃H₇ | OCF₃ | H | H | | |
| 400 | n-C₃H₇ | OCF₃ | F | H | | |
| 401 | n-C₃H₇ | OCF₃ | F | F | | |
| 402 | n-C₃H₇ | CN | H | H | | |
| 403 | n-C₃H₇ | CN | F | H | | |
| 404 | n-C₃H₇ | CN | F | F | | |
| 405 | n-C₄H₉ | F | H | H | | |
| 406 | n-C₄H₉ | F | F | H | | |
| 407 | n-C₄H₉ | F | F | F | | |
| 408 | n-C₄H₉ | Cl | H | H | | |
| 409 | n-C₄H₉ | Cl | F | H | | |
| 410 | n-C₄H₉ | Cl | F | F | | |
| 411 | n-C₄H₉ | CF₃ | H | H | | |
| 412 | n-C₄H₉ | CF₃ | F | H | | |
| 413 | n-C₄H₉ | CF₃ | F | F | | |
| 414 | n-C₄H₉ | OCF₃ | H | H | | |
| 415 | n-C₄H₉ | OCF₃ | F | H | | |
| 416 | n-C₄H₉ | OCF₃ | F | F | | |
| 417 | n-C₄H₉ | CN | H | H | | |
| 418 | n-C₄H₉ | CN | F | H | | |
| 419 | n-C₄H₉ | CN | F | F | | |
| 420 | CH₃O | F | H | H | | |
| 421 | CH₃O | F | F | H | | |
| 422 | CH₃O | F | F | F | | |
| 423 | CH₃O | Cl | H | H | | |
| 424 | CH₃O | Cl | F | H | | |
| 425 | CH₃O | Cl | F | F | | |
| 426 | CH₃O | CF₃ | H | H | | |
| 427 | CH₃O | CF₃ | F | H | | |
| 428 | CH₃O | CF₃ | F | F | | |
| 429 | CH₃O | OCF₃ | H | H | | |
| 430 | CH₃O | OCF₃ | F | H | | |
| 431 | CH₃O | OCF₃ | F | F | | |
| 432 | CH₃O | CN | H | H | | |
| 453 | CH₃O | CN | F | H | | |
| 434 | CH₃O | CN | F | F | | |
| 435 | C₂H₅O | F | H | H | | |
| 436 | C₂H₅O | F | F | H | | |
| 437 | C₂H₅O | F | F | F | | |
| 438 | C₂H₅O | Cl | H | H | | |
| 439 | C₂H₅O | Cl | F | H | | |
| 440 | C₂H₅O | Cl | F | F | | |
| 441 | C₂H₅O | CF₃ | H | H | | |
| 442 | C₂H₅O | CF₃ | F | H | | |
| 443 | C₂H₅O | CF₃ | F | F | | |
| 444 | C₂H₅O | OCF₃ | H | H | | |
| 445 | C₂H₅O | OCF₃ | F | H | | |
| 446 | C₂H₅O | OCF₃ | F | F | | |
| 447 | C₂H₅O | CN | H | H | | |
| 448 | C₂H₅O | CN | F | H | | |
| 449 | C₂H₅O | CN | F | F | | |
| 450 | CH₂=CH | F | H | H | | |
| 451 | CH₂=CH | F | F | H | | |
| 452 | CH₂=CH | F | F | F | | |
| 453 | CH₂=CH | Cl | H | H | | |
| 454 | CH₂=CH | Cl | F | H | | |
| 455 | CH₂=CH | Cl | F | F | | |
| 456 | CH₂=CH | CF₃ | H | H | | |
| 457 | CH₂=CH | CF₃ | F | H | | |
| 458 | CH₂=CH | CF₃ | F | F | | |
| 459 | CH₂=CH | OCF₃ | H | H | | |
| 460 | CH₂=CH | OCF₃ | F | H | | |
| 461 | CH₂=CH | OCF₃ | F | F | | |
| 462 | CH₂=CH | CN | H | H | | |
| 463 | CH₂=CH | CN | F | H | | |
| 464 | CH₂=CH | CN | F | F | | |
| 465 | CH₂=CH—O | F | H | H | | |
| 466 | CH₂=CH—O | F | F | H | | |
| 467 | CH₂=CH—O | F | F | F | | |
| 468 | CH₂=CH—O | Cl | H | H | | |
| 469 | CH₂=CH—O | Cl | F | H | | |

-continued

| No. | R¹ | R² | L¹¹ | R¹² | Phase sequence Δε* T/° C. | T*(N, I)/ ° C. |
|---|---|---|---|---|---|---|
| 470 | CH₂=CH—O | Cl | F | F | | |
| 471 | CH₂=CH—O | CF₃ | H | H | | |
| 472 | CH₂=CH—O | CF₃ | F | H | | |
| 473 | CH₂=CH—O | CF₃ | F | F | | |
| 474 | CH₂=CH—O | OCF₃ | H | H | | |
| 475 | CH₂=CH—O | OCF₃ | F | H | | |
| 476 | CH₂=CH—O | OCF₃ | F | F | | |
| 477 | CH₂=CH—O | CN | H | H | | |
| 478 | CH₂=CH—O | CN | F | H | | |
| 479 | CH₂=CH—O | CN | F | F | | |

Note:
*values extrapolated from 10% solution in ZLI-4792.

Examples 480 to 569

Compounds of the formula:

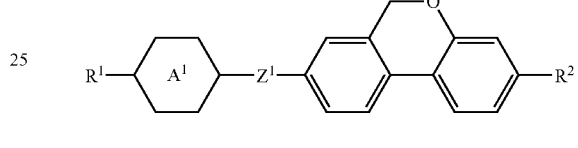

in which

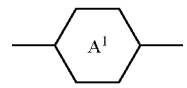

denotes

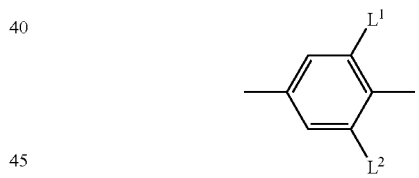

and
Z¹ denotes a single bond,
are prepared analogously to the preceding examples.

| No. | R¹ | R² | L¹¹ | R¹² | Phase sequence Δε* T/° C. | T*(N, I)/ ° C. |
|---|---|---|---|---|---|---|
| 480 | CH₃ | F | H | H | | |
| 481 | CH₃ | F | F | H | | |
| 482 | CH₃ | F | F | F | | |
| 483 | CH₃ | Cl | H | H | | |
| 484 | CH₃ | Cl | F | H | | |
| 485 | CH₃ | Cl | F | F | | |
| 486 | CH₃ | CF₃ | H | H | | |
| 487 | CH₃ | CF₃ | F | H | | |
| 488 | CH₃ | CF₃ | F | F | | |
| 489 | CH₃ | OCF₃ | H | H | | |
| 490 | CH₃ | OCF₃ | F | H | | |
| 491 | CH₃ | OCF₃ | F | F | | |
| 492 | CH₃ | CN | H | H | | |

| No. | R¹ | R² | L¹¹ | R¹² | Phase sequence Δε* T/° C. | T*(N, I)/ ° C. |
|---|---|---|---|---|---|---|
| 493 | CH₃ | CN | F | H | | |
| 494 | CH₃ | CN | F | F | | |
| 495 | C₂H₅ | F | H | H | | |
| 496 | C₂H₅ | F | F | H | | |
| 497 | C₂H₅ | F | F | F | | |
| 498 | C₂H₅ | Cl | H | H | | |
| 499 | C₂H₅ | Cl | F | H | | |
| 500 | C₂H₅ | Cl | F | F | | |
| 501 | C₂H₅ | CF₃ | H | H | | |
| 502 | C₂H₅ | CF₃ | F | H | | |
| 503 | C₂H₅ | CF₃ | F | F | | |
| 504 | C₂H₅ | OCF₃ | H | H | | |
| 505 | C₂H₅ | OCF₃ | F | H | | |
| 586 | C₂H₅ | OCF₃ | F | F | | |
| 507 | C₂H₅ | CN | H | H | | |
| 508 | C₂H₅ | CN | F | H | | |
| 509 | C₂H₅ | CN | F | F | | |
| 510 | n-C₃H₇ | F | H | H | | |
| 511 | n-C₃H₇ | F | F | H | | |
| 512 | n-C₃H₇ | F | F | F | | |
| 513 | n-C₃H₇ | Cl | H | H | | |
| 514 | n-C₃H₇ | Cl | F | H | | |
| 515 | n-C₃H₇ | Cl | F | F | | |
| 516 | n-C₃H₇ | CF₃ | H | H | | |
| 517 | n-C₃H₇ | CF₃ | F | H | | |
| 518 | n-C₃H₇ | CF₃ | F | F | | |
| 519 | n-C₃H₇ | OCF₃ | H | H | | |
| 520 | n-C₃H₇ | OCF₃ | F | H | | |
| 521 | n-C₃H₇ | OCF₃ | F | F | | |
| 522 | n-C₃H₇ | CN | H | H | | |
| 523 | n-C₃H₇ | CN | F | H | | |
| 524 | n-C₃H₇ | CN | F | F | | |
| 525 | n-C₄H₉ | F | H | H | | |
| 526 | n-C₄H₉ | F | F | H | | |
| 527 | n-C₄H₉ | F | F | F | | |
| 528 | n-C₄H₉ | Cl | H | H | | |
| 529 | n-C₄H₉ | Cl | F | H | | |
| 530 | n-C₄H₉ | Cl | F | F | | |
| 531 | n-C₄H₉ | CF₃ | H | H | | |
| 532 | n-C₄H₉ | CF₃ | F | H | | |
| 533 | n-C₄H₉ | CF₃ | F | F | | |
| 534 | n-C₄H₉ | OCF₃ | H | H | | |
| 535 | n-C₄H₉ | OCF₃ | F | H | | |
| 536 | n-C₄H₉ | OCF₃ | F | F | | |
| 537 | n-C₄H₉ | CN | H | H | | |
| 538 | n-C₄H₉ | CN | F | H | | |
| 539 | n-C₄H₉ | CN | F | F | | |
| 540 | CH₂=CH | F | H | H | | |
| 541 | CH₂=CH | F | F | H | | |
| 542 | CH₂=CH | F | F | F | | |
| 543 | CH₂=CH | Cl | H | H | | |
| 544 | CH₂=CH | Cl | F | H | | |
| 545 | CH₂=CH | Cl | F | F | | |
| 546 | CH₂=CH | CF₃ | H | H | | |
| 547 | CH₂=CH | CF₃ | F | H | | |
| 548 | CH₂=CH | CF₃ | F | F | | |
| 549 | CH₂=CH | OCF₃ | H | H | | |
| 550 | CH₂=CH | OCF₃ | F | H | | |
| 551 | CH₂=CH | OCF₃ | F | F | | |
| 552 | CH₂=CH | CN | H | H | | |
| 553 | CH₂=CH | CN | F | H | | |
| 554 | CH₂=CH | CN | F | F | | |
| 555 | CH₂=CH—O | F | H | H | | |
| 556 | CH₂=CH—O | F | F | H | | |
| 557 | CH₂=CH—O | F | F | F | | |
| 558 | CH₂=CH—O | Cl | H | H | | |
| 559 | CH₂=CH—O | Cl | F | H | | |
| 560 | CH₂=CH—O | Cl | F | F | | |
| 561 | CH₂=CH—O | CF₃ | H | H | | |
| 562 | CH₂=CH—O | CF₃ | F | H | | |
| 563 | CH₂=CH—O | CF₃ | F | F | | |
| 564 | CH₂=CH—O | OCF₃ | H | H | | |
| 565 | CH₂=CH—O | OCF₃ | F | H | | |
| 566 | CH₂=CH—O | OCF₃ | F | F | | |
| 567 | CH₂=CH—O | CN | H | H | | |
| 568 | CH₂=CH—O | CN | F | H | | |
| 569 | CH₂=CH—O | CN | F | F | | |

Note:
*values extrapolated from 10% solution in ZLI-4792.

Examples 570 to 599

Compounds of the formula:

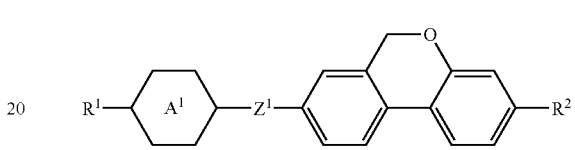

in which

denotes $$\begin{matrix}&&L^{11}\\&&\\&&\\&&L^{12}\end{matrix}$$

$L^{11}$ and $L^{12}$ denote H, and
$Z^1$ denotes $CF_2O$,
are prepared analogously to the preceding examples.

| No. | R¹ | R² | Phase sequence Δε* T/° C. |
|---|---|---|---|
| 570 | CH₃ | F | |
| 571 | CH₃ | Cl | |
| 572 | CH₃ | CF₃ | |
| 573 | CH₃ | OCF₃ | |
| 574 | C₂H₅ | F | |
| 575 | C₂H₅ | Cl | |
| 576 | C₂H₅ | CF₃ | |
| 577 | C₂H₅ | OCF₃ | |
| 578 | n-C₃H₇ | F | |
| 579 | n-C₃H₇ | Cl | |
| 580 | n-C₃H₇ | CF₃ | |
| 581 | n-C₃H₇ | OCF₃ | |
| 582 | n-C₄H₉ | F | |
| 583 | n-C₄H₉ | Cl | |
| 584 | n-C₄H₉ | CF₃ | |
| 585 | n-C₄H₉ | OCF₃ | |
| 586 | n-C₅H₁₁ | F | |
| 587 | n-C₅H₁₁ | Cl | |
| 588 | n-C₅H₁₁ | CF₃ | |
| 589 | n-C₅H₁₁ | OCF₃ | |
| 590 | n-C₇H₁₅ | F | |

-continued

| No. | R¹ | R² | Phase sequence Δε* T/° C. |
|---|---|---|---|
| 591 | n-C₇H₁₅ | Cl | |
| 592 | n-C₇H₁₅ | CF₃ | |
| 593 | n-C₇H₁₅ | OCF₃ | |
| 594 | CH₂=CH | F | |
| 595 | CH₂=CH | Cl | |
| 596 | CH₂=CH | CF₃ | |
| 597 | CH₂=CH | OCF₃ | |
| 598 | E-CH₃—CH=CH | F | |
| 599 | E-CH₃—CH=CH | Cl | |

Note:
*values extrapolated from 10% solution in ZLI-4792.

Examples 600 to 629

Compounds of the formula:

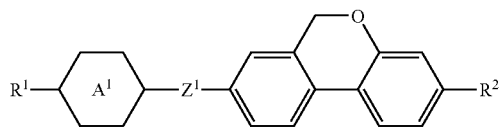

in which

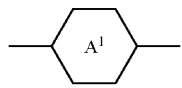

denotes

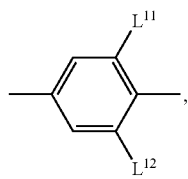

$L^{11}$ denotes H,
$L^{12}$ denotes F, and
$Z^1$ denotes $CF_2O$,
are prepared analogously to the preceding examples.

| No. | R¹ | R² | Phase sequence Δε* T/° C. |
|---|---|---|---|
| 600 | CH₃ | F | |
| 601 | CH₃ | Cl | |
| 602 | CH₃ | CF₃ | |
| 603 | CH₃ | OCF₃ | |
| 604 | C₂H₅ | F | |
| 605 | C₂H₅ | Cl | |
| 606 | C₂H₅ | CF₃ | |
| 607 | C₂H₅ | OCF₃ | |
| 608 | n-C₃H₇ | F | |
| 609 | n-C₃H₇ | Cl | |
| 610 | n-C₃H₇ | CF₃ | |
| 611 | n-C₃H₇ | OCF₃ | |
| 612 | n-C₄H₉ | F | |
| 613 | n-C₄H₉ | Cl | |

-continued

| No. | R¹ | R² | Phase sequence Δε* T/° C. |
|---|---|---|---|
| 614 | n-C₄H₉ | CF₃ | |
| 615 | n-C₄H₉ | OCF₃ | |
| 616 | n-C₅H₁₁ | F | |
| 617 | n-C₅H₁₁ | Cl | |
| 618 | n-C₅H₁₁ | CF₃ | |
| 619 | n-C₅H₁₁ | OCF₃ | |
| 620 | n-C₇H₁₅ | F | |
| 621 | n-C₇H₁₅ | Cl | |
| 622 | n-C₇H₁₅ | CF₃ | |
| 623 | n-C₇H₁₅ | OCF₃ | |
| 624 | CH₂=CH | F | |
| 625 | CH₂=CH | Cl | |
| 626 | CH₂=CH | CF₃ | |
| 627 | CH₂=CH | OCF₃ | |
| 628 | E-CH₃—CH=CH | F | |
| 629 | E-CH₃—CH=CH | Cl | |

Note:
*values extrapolated from 10% solution in ZLI-4792.

Examples 630 to 659

Compounds of the formula:

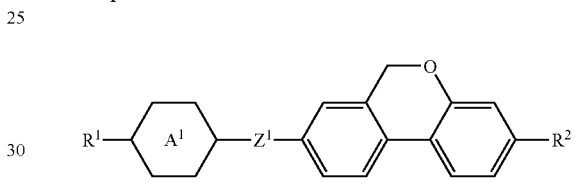

in which

denotes

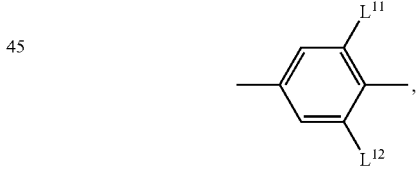

$L^{11}$ and $L^{12}$ denote F, and
$Z^1$ denotes $CF_2O$,
are prepared analogously to the preceding examples.

| No. | R¹ | R² | Phase sequence Δε* T/° C. |
|---|---|---|---|
| 630 | CH₃ | F | |
| 631 | CH₃ | Cl | |
| 632 | CH₃ | CF₃ | |
| 633 | CH₃ | OCF₃ | |
| 634 | C₂H₅ | F | |
| 635 | C₂H₅ | Cl | |
| 636 | C₂H₅ | CF₃ | |
| 637 | C₂H₅ | OCF₃ | |
| 638 | n-C₃H₇ | F | |

-continued

| No. | $R^1$ | $R^2$ | Phase sequence $\Delta\epsilon^*$ T/° C. |
|---|---|---|---|
| 639 | n-$C_3H_7$ | Cl | |
| 640 | n-$C_3H_7$ | $CF_3$ | |
| 641 | n-$C_3H_7$ | $OCF_3$ | |
| 642 | n-$C_4H_9$ | F | |
| 643 | n-$C_4H_9$ | Cl | |
| 644 | n-$C_4H_9$ | $CF_3$ | |
| 645 | n-$C_4H_9$ | $OCF_3$ | |
| 646 | n-$C_5H_{11}$ | F | |
| 677 | n-$C_5H_{11}$ | Cl | |
| 648 | n-$C_5H_{11}$ | $CF_3$ | |
| 649 | n-$C_5H_{11}$ | $OCF_3$ | |
| 650 | n-$C_7H_{15}$ | F | |
| 651 | n-$C_7H_{15}$ | Cl | |
| 652 | n-$C_7H_{15}$ | $CF_3$ | |
| 653 | n-$C_7H_{15}$ | $OCF_3$ | |
| 654 | $CH_2$=CH | F | |
| 655 | $CH_2$=CH | Cl | |
| 656 | $CH_2$=CH | $CF_3$ | |
| 657 | $CH_2$=CH | $OCF_3$ | |
| 658 | E-$CH_3$—CH=CH | F | |
| 659 | E-$CH_3$—CH=CH | Cl | |

Note:
*values extrapolated from 10% solution in ZLI-4792.

Examples 660 to 689

Compounds of the formula:

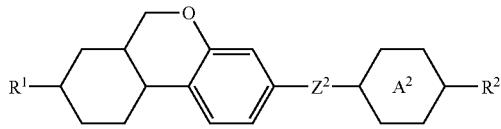

in which

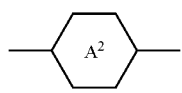

denotes

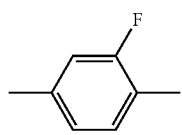

and
$Z^2$ denotes a single bond,
are prepared analogously to the preceding examples.

| No. | $R^1$ | $R^2$ | Phase sequence $\Delta\epsilon^*$ T/° C. |
|---|---|---|---|
| 660 | $CH_3$ | F | |
| 661 | $CH_3$ | Cl | |
| 662 | $CH_3$ | $CF_3$ | |
| 663 | $CH_3$ | $OCF_3$ | |
| 664 | $C_2H_5$ | F | |
| 665 | $C_2H_5$ | Cl | |

-continued

| No. | $R^1$ | $R^2$ | Phase sequence $\Delta\epsilon^*$ T/° C. |
|---|---|---|---|
| 666 | $C_2H_5$ | $CF_3$ | |
| 667 | $C_2H_5$ | $OCF_3$ | |
| 668 | n-$C_3H_7$ | F | |
| 669 | n-$C_3H_7$ | Cl | |
| 670 | n-$C_3H_7$ | $CF_3$ | |
| 671 | n-$C_3H_7$ | $OCF_3$ | |
| 672 | n-$C_4H_9$ | F | |
| 673 | n-$C_4H_9$ | Cl | |
| 674 | n-$C_4H_9$ | $CF_3$ | |
| 675 | n-$C_4H_9$ | $OCF_3$ | |
| 676 | n-$C_5H_{11}$ | F | |
| 677 | n-$C_5H_{11}$ | Cl | |
| 678 | n-$C_5H_{11}$ | $CF_3$ | |
| 679 | n-$C_5H_{11}$ | $OCF_3$ | |
| 680 | n-$C_7H_{15}$ | F | |
| 681 | n-$C_7H_{15}$ | Cl | |
| 682 | n-$C_7H_{15}$ | $CF_3$ | |
| 683 | n-$C_7H_{15}$ | $OCF_3$ | |
| 684 | $CH_2$=CH | F | |
| 685 | $CH_2$=CH | Cl | |
| 686 | $CH_2$=CH | $CF_3$ | |
| 687 | $CH_2$=CH | $OCF_3$ | |
| 688 | E-$CH_3$—CH=CH | F | |
| 689 | E-$CH_3$—CH=CH | Cl | |

Note:
*values extrapolated from 10% solution in ZLI-4792.

Examples 690 to 719

Compounds of the formula:

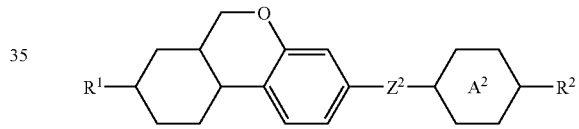

in which

denotes

and
$Z^2$ denotes a single bond,
are prepared analogously to the preceding examples.

| No. | $R^1$ | $R^2$ | Phase sequence $\Delta\epsilon^*$ T/° C. |
|---|---|---|---|
| 690 | $CH_3$ | F | |
| 691 | $CH_3$ | Cl | |
| 692 | $CH_3$ | $CF_3$ | |

-continued

| No. | R¹ | R² | Phase sequence Δε* T/° C. |
|---|---|---|---|
| 693 | CH₃ | OCF₃ | |
| 694 | C₂H₅ | F | |
| 695 | C₂H₅ | Cl | |
| 696 | C₂H₅ | CF₃ | |
| 697 | C₂H₅ | OCF₃ | |
| 698 | n-C₃H₇ | F | |
| 699 | n-C₃H₇ | Cl | |
| 700 | n-C₃H₇ | CF₃ | |
| 701 | n-C₃H₇ | OCF₃ | |
| 702 | n-C₄H₉ | F | |
| 703 | n-C₄H₉ | Cl | |
| 704 | n-C₄H₉ | CF₃ | |
| 705 | n-C₄H₉ | OCF₃ | |
| 706 | n-C₅H₁₁ | F | |
| 707 | n-C₅H₁₁ | Cl | |
| 708 | n-C₅H₁₁ | CF₃ | |
| 709 | n-C₅H₁₁ | OCF₃ | |
| 710 | n-C₇H₁₅ | F | |
| 711 | n-C₇H₁₅ | Cl | |
| 712 | n-C₇H₁₅ | CF₃ | |
| 713 | n-C₇H₁₅ | OCF₃ | |
| 714 | CH₂=CH | F | |
| 715 | CH₂=CH | Cl | |
| 716 | CH₂=CH | CF₃ | |
| 717 | CH₂=CH | OCF₃ | |
| 718 | E-CH₃—CH=CH | F | |
| 719 | E-CH₃—CH=CH | Cl | |

Note:
*values extrapolated from 10% solution in ZLI-4792.

Examples 720 to 749

Compounds of the formula:

in which denotes and
$Z^2$ denotes a single bond,
are prepared analogously to the preceding examples.

| No. | R¹ | R² | Phase sequence Δε* T/° C. |
|---|---|---|---|
| 720 | CH₃ | F | |
| 721 | CH₃ | Cl | |

-continued

| No. | R¹ | R² | Phase sequence Δε* T/° C. |
|---|---|---|---|
| 722 | CH₃ | CF₃ | |
| 723 | CH₃ | OCF₃ | |
| 724 | C₂H₅ | F | |
| 725 | C₂H₅ | Cl | |
| 726 | C₂H₅ | CF₃ | |
| 727 | C₂H₅ | OCF₃ | |
| 728 | n-C₃H₇ | F | |
| 729 | n-C₃H₇ | Cl | |
| 730 | n-C₃H₇ | CF₃ | |
| 731 | n-C₃H₇ | OCF₃ | |
| 732 | n-C₄H₉ | F | |
| 733 | n-C₄H₉ | Cl | |
| 734 | n-C₄H₉ | CF₃ | |
| 735 | n-C₄H₉ | OCF₃ | |
| 736 | n-C₅H₁₁ | F | |
| 737 | n-C₅H₁₁ | Cl | |
| 738 | n-C₅H₁₁ | CF₃ | |
| 739 | n-C₅H₁₁ | OCF₃ | |
| 740 | n-C₇H₁₅ | F | |
| 741 | n-C₇H₁₅ | Cl | |
| 742 | n-C₇H₁₅ | CF₃ | |
| 743 | n-C₇H₁₅ | OCF₃ | |
| 744 | CH₂=CH | F | |
| 745 | CH₂=CH | Cl | |
| 746 | CH₂=CH | CF₃ | |
| 747 | CH₂=CH | OCF₃ | |
| 748 | E-CH₃—CH=CH | F | |
| 749 | E-CH₃—CH=CH | Cl | |

Note:
*values extrapolated from 10% solution in ZLI-4792.

Examples 750 to 779

Compounds of the formula:

in which denotes and
$Z^2$ denotes a single bond,
are prepared analogously to the preceding examples.

| No. | R¹ | R² | Phase sequence Δε* T/° C. |
|---|---|---|---|
| 750 | CH₃ | F | |
| 751 | CH₃ | Cl | |
| 752 | CH₃ | CF₃ | |
| 753 | CH₃ | OCF₃ | |
| 754 | C₂H₅ | F | |
| 755 | C₂H₅ | Cl | |
| 756 | C₂H₅ | CF₃ | |
| 757 | C₂H₅ | OCF₃ | |
| 758 | n-C₃H₇ | F | |
| 759 | n-C₃H₇ | Cl | |
| 760 | n-C₃H₇ | CF₃ | |
| 761 | n-C₃H₇ | OCF₃ | |
| 762 | n-C₄H₉ | F | |
| 763 | n-C₄H₉ | Cl | |
| 764 | n-C₄H₉ | CF₃ | |
| 765 | n-C₄H₉ | OCF₃ | |
| 766 | n-C₅H₁₁ | F | |
| 767 | n-C₅H₁₁ | Cl | |
| 768 | n-C₅H₁₁ | CF₃ | |
| 769 | n-C₅H₁₁ | OCF₃ | |
| 770 | n-C₇H₁₅ | F | |
| 771 | n-C₇H₁₅ | Cl | |
| 772 | n-C₇H₁₅ | CF₃ | |
| 773 | n-C₇H₁₅ | OCF₃ | |
| 774 | CH₂=CH | F | |
| 775 | CH₂=CH | Cl | |
| 776 | CH₂=CH | CF₃ | |
| 777 | CH₂=CH | OCF₃ | |
| 778 | E-CH₃—CH=CH | F | |
| 779 | E-CH₃—CH=CH | Cl | |

Note:
*values extrapolated from 10% solution in ZLI-4792.

| No. | R¹ | R² | Phase sequence Δε* T/° C. |
|---|---|---|---|
| 780 | CH₃ | F | |
| 781 | CH₃ | Cl | |
| 782 | CH₃ | CF₃ | |
| 783 | CH₃ | OCF₃ | |
| 784 | C₂H₅ | F | |
| 785 | C₂H₅ | Cl | |
| 786 | C₂H₅ | CF₃ | |
| 787 | C₂H₅ | OCF₃ | |
| 788 | n-C₃H₇ | F | |
| 789 | n-C₃H₇ | Cl | |
| 790 | n-C₃H₇ | CF₃ | |
| 791 | n-C₃H₇ | OCF₃ | |
| 792 | n-C₄H₉ | F | |
| 793 | n-C₄H₉ | Cl | |
| 794 | n-C₄H₉ | CF₃ | |
| 795 | n-C₄H₉ | OCF₃ | |
| 796 | n-C₅H₁₁ | F | |
| 797 | n-C₅H₁₁ | Cl | |
| 798 | n-C₅H₁₁ | CF₃ | |
| 799 | n-C₅H₁₁ | OCF₃ | |
| 800 | n-C₇H₁₅ | F | |
| 801 | n-C₇H₁₅ | Cl | |
| 802 | n-C₇H₁₅ | CF₃ | |
| 803 | n-C₇H₁₅ | OCF₃ | |
| 804 | CH₂=CH | F | |
| 805 | CH₂=CH | Cl | |
| 806 | CH₂=CH | CF₃ | |
| 807 | CH₂=CH | OCF₃ | |
| 808 | E-CH₃—CH=CH | F | |
| 809 | E-CH₃—CH=CH | Cl | |

Note:
*values extrapolated from 10% solution in ZLI-4792.

Examples 780 to 809

Compounds of the formula:

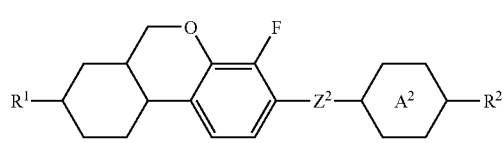

in which

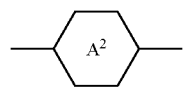

denotes

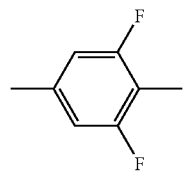

and

Z² denotes a single bond, are prepared analogously to the preceding examples.

Examples 810 to 839

Compounds of the formula:

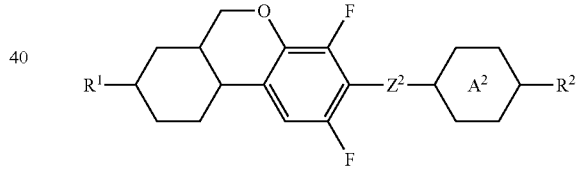

in which

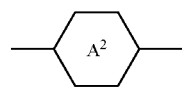

denotes

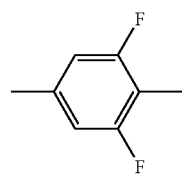

and

Z² denotes a single bond, are prepared analogously to the preceding examples.

| No. | R¹ | R² | Phase sequence Δε* T/° C. |
|---|---|---|---|
| 810 | $CH_3$ | F | |
| 811 | $CH_3$ | Cl | |
| 812 | $CH_3$ | $CF_3$ | |
| 813 | $CH_3$ | $OCF_3$ | |
| 814 | $C_2H_5$ | F | |
| 815 | $C_2H_5$ | Cl | |
| 816 | $C_2H_5$ | $CF_3$ | |
| 817 | $C_2H_5$ | $OCF_3$ | |
| 818 | $n\text{-}C_3H_7$ | F | |
| 819 | $n\text{-}C_3H_7$ | Cl | |
| 820 | $n\text{-}C_3H_7$ | $CF_3$ | |
| 821 | $n\text{-}C_3H_7$ | $OCF_3$ | |
| 822 | $n\text{-}C_4H_9$ | F | |
| 823 | $n\text{-}C_4H_9$ | Cl | |
| 824 | $n\text{-}C_4H_9$ | $CF_3$ | |
| 825 | $n\text{-}C_4H_9$ | $OCF_3$ | |
| 826 | $n\text{-}C_5H_{11}$ | F | |
| 827 | $n\text{-}C_5H_{11}$ | Cl | |
| 828 | $n\text{-}C_5H_{11}$ | $CF_3$ | |
| 829 | $n\text{-}C_5H_{11}$ | $OCF_3$ | |
| 830 | $n\text{-}C_7H_{15}$ | F | |
| 831 | $n\text{-}C_7H_{15}$ | Cl | |
| 832 | $n\text{-}C_7H_{15}$ | $CF_3$ | |
| 833 | $n\text{-}C_7H_{15}$ | $OCF_3$ | |
| 834 | $CH_2=CH$ | F | |
| 835 | $CH_2=CH$ | Cl | |
| 836 | $CH_2=CH$ | $CF_3$ | |
| 837 | $CH_2=CH$ | $OCF_3$ | |
| 838 | $E\text{-}CH_3\text{—}CH=CH$ | F | |
| 839 | $E\text{-}CH_3\text{—}CH=CH$ | Cl | |

Note:
*values extrapolated from 10% solution in ZLI-4792.

| No. | R¹ | R² | Phase sequence Δε* T/° C. |
|---|---|---|---|
| 840 | $CH_3$ | F | |
| 841 | $CH_3$ | Cl | |
| 842 | $CH_3$ | $CF_3$ | |
| 843 | $CH_3$ | $OCF_3$ | |
| 844 | $C_2H_5$ | F | |
| 845 | $C_2H_5$ | Cl | |
| 846 | $C_2H_5$ | $CF_3$ | |
| 847 | $C_2H_5$ | $OCF_3$ | |
| 848 | $n\text{-}C_3H_7$ | F | |
| 849 | $n\text{-}C_3H_7$ | Cl | |
| 850 | $n\text{-}C_3H_7$ | $CF_3$ | |
| 851 | $n\text{-}C_3H_7$ | $OCF_3$ | |
| 852 | $n\text{-}C_4H_9$ | F | |
| 853 | $n\text{-}C_4H_9$ | Cl | |
| 854 | $n\text{-}C_4H_9$ | $CF_3$ | |
| 855 | $n\text{-}C_4H_9$ | $OCF_3$ | |
| 856 | $n\text{-}C_5H_{11}$ | F | |
| 857 | $n\text{-}C_5H_{11}$ | Cl | |
| 858 | $n\text{-}C_5H_{11}$ | $CF_3$ | |
| 859 | $n\text{-}C_5H_{11}$ | $OCF_3$ | |
| 860 | $n\text{-}C_7H_{15}$ | F | |
| 861 | $n\text{-}C_7H_{15}$ | Cl | |
| 862 | $n\text{-}C_7H_{15}$ | $CF_3$ | |
| 863 | $n\text{-}C_7H_{15}$ | $OCF_3$ | |
| 864 | $CH_2=CH$ | F | |
| 865 | $CH_2=CH$ | Cl | |
| 866 | $CH_2=CH$ | $CF_3$ | |
| 867 | $CH_2=CH$ | $OCF_3$ | |
| 868 | $E\text{-}CH_3\text{—}CH=CH$ | F | |
| 869 | $E\text{-}CH_3\text{—}CH=CH$ | Cl | |

Note:
*values extrapolated from 10% solution in ZLI-4792.

Examples 840 to 869

Compounds of the formula:

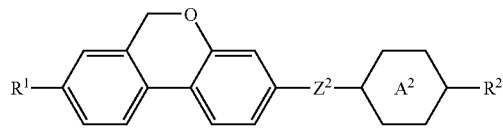

in which

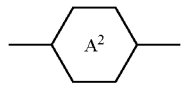

denotes

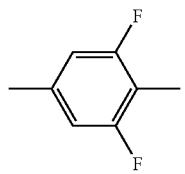

and $Z^2$ denotes a single bond, are prepared analogously to the preceding examples.

Examples 870 to 899

Compounds of the formula:

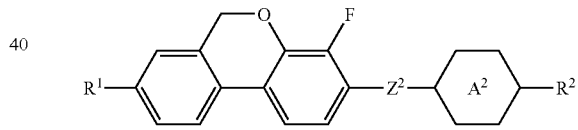

in which

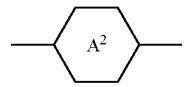

denotes

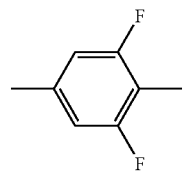

and $Z^2$ denotes a single bond, are prepared analogously to the preceding examples.

| No. | R¹ | R² | Phase sequence Δε* T/° C. |
|---|---|---|---|
| 870 | $CH_3$ | F | |
| 871 | $CH_3$ | Cl | |
| 872 | $CH_3$ | $CF_3$ | |
| 873 | $CH_3$ | $OCF_3$ | |
| 874 | $C_2H_5$ | F | |
| 875 | $C_2H_5$ | Cl | |
| 876 | $C_2H_5$ | $CF_3$ | |
| 877 | $C_2H_5$ | $OCF_3$ | |
| 878 | n-$C_3H_7$ | F | |
| 879 | n-$C_3H_7$ | Cl | |
| 880 | n-$C_3H_7$ | $CF_3$ | |
| 881 | n-$C_3H_7$ | $OCF_3$ | |
| 882 | n-$C_4H_9$ | F | |
| 883 | n-$C_4H_9$ | Cl | |
| 884 | n-$C_4H_9$ | $CF_3$ | |
| 885 | n-$C_4H_9$ | $OCF_3$ | |
| 886 | n-$C_5H_{11}$ | F | |
| 887 | n-$C_5H_{11}$ | Cl | |
| 888 | n-$C_5H_{11}$ | $CF_3$ | |
| 889 | n-$C_5H_{11}$ | $OCF_3$ | |
| 890 | n-$C_7H_{15}$ | F | |
| 891 | n-$C_7H_{15}$ | Cl | |
| 892 | n-$C_7H_{15}$ | $CF_3$ | |
| 893 | n-$C_7H_{15}$ | $OCF_3$ | |
| 894 | $CH_2=CH$ | F | |
| 895 | $CH_2=CH$ | Cl | |
| 896 | $CH_2=CH$ | $CF_3$ | |
| 897 | $CH_2=CH$ | $OCF_3$ | |
| 898 | E-$CH_3$—CH=CH | F | |
| 899 | E-$CH_3$—CH=CH | Cl | |

Note:
*values extrapolated from 10% solution in ZLI-4792.

| No. | R¹ | R² | Phase sequence Δε* T/° C. |
|---|---|---|---|
| 900 | $CH_3$ | F | |
| 901 | $CH_3$ | Cl | |
| 902 | $CH_3$ | $CF_3$ | |
| 903 | $CH_3$ | $OCF_3$ | |
| 904 | $C_2H_5$ | F | |
| 905 | $C_2H_5$ | Cl | |
| 906 | $C_2H_5$ | $CF_3$ | |
| 907 | $C_2H_5$ | $OCF_3$ | |
| 908 | n-$C_3H_7$ | F | |
| 909 | n-$C_3H_7$ | Cl | |
| 910 | n-$C_3H_7$ | $CF_3$ | |
| 911 | n-$C_3H_7$ | $OCF_3$ | |
| 912 | n-$C_4H_9$ | F | |
| 913 | n-$C_4H_9$ | Cl | |
| 914 | n-$C_4H_9$ | $CF_3$ | |
| 915 | n-$C_4H_9$ | $OCF_3$ | |
| 916 | n-$C_5H_{11}$ | F | |
| 917 | n-$C_5H_{11}$ | Cl | |
| 918 | n-$C_5H_{11}$ | $CF_3$ | |
| 919 | n-$C_5H_{11}$ | $OCF_3$ | |
| 920 | n-$C_7H_{15}$ | F | |
| 921 | n-$C_7H_{15}$ | Cl | |
| 922 | n-$C_7H_{15}$ | $CF_3$ | |
| 923 | n-$C_7H_{15}$ | $OCF_3$ | |
| 924 | $CH_2=CH$ | F | |
| 925 | $CH_2=CH$ | Cl | |
| 926 | $CH_2=CH$ | $CF_3$ | |
| 927 | $CH_2=CH$ | $OCF_3$ | |
| 928 | E-$CH_3$—CH=CH | F | |
| 929 | E-$CH_3$—CH=CH | Cl | |

Note:
*values extrapolated from 10% solution in ZLI-4792.

Examples 900 to 929

Compounds of the formula:

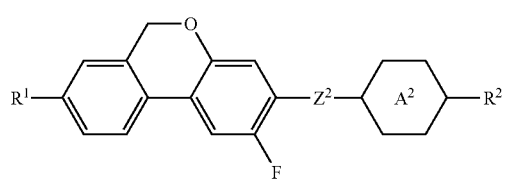

in which

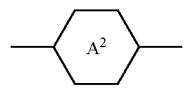

denotes

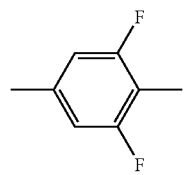

and
$Z^2$ denotes a single bond,
are prepared analogously to the preceding examples.

Examples 930 to 959

Compounds of the formula:

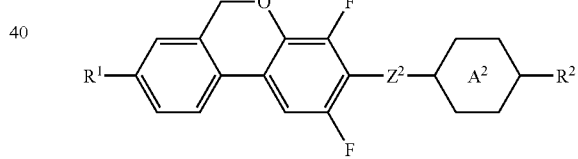

in which

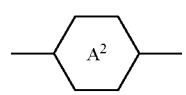

denotes

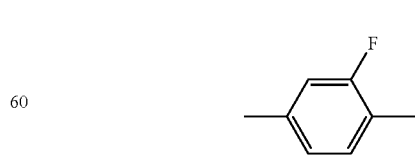

and
$Z^2$ denotes a single bond,
are prepared analogously to the preceding examples.

| No. | $R^1$ | $R^2$ | Phase sequence $\Delta\epsilon^*$ T/° C. |
|---|---|---|---|
| 930 | $CH_3$ | F | |
| 931 | $CH_3$ | Cl | |
| 932 | $CH_3$ | $CF_3$ | |
| 933 | $CH_3$ | $OCF_3$ | |
| 934 | $C_2H_5$ | F | |
| 935 | $C_2H_5$ | Cl | |
| 936 | $C_2H_5$ | $CF_3$ | |
| 937 | $C_2H_5$ | $OCF_3$ | |
| 938 | $n$-$C_3H_7$ | F | |
| 939 | $n$-$C_3H_7$ | Cl | |
| 940 | $n$-$C_3H_7$ | $CF_3$ | |
| 941 | $n$-$C_3H_7$ | $OCF_3$ | |
| 942 | $n$-$C_4H_9$ | F | |
| 943 | $n$-$C_4H_9$ | Cl | |
| 944 | $n$-$C_4H_9$ | $CF_3$ | |
| 945 | $n$-$C_4H_9$ | $OCF_3$ | |
| 946 | $n$-$C_5H_{11}$ | F | |
| 947 | $n$-$C_5H_{11}$ | Cl | |
| 948 | $n$-$C_5H_{11}$ | $CF_3$ | |
| 949 | $n$-$C_5H_{11}$ | $OCF_3$ | |
| 950 | $n$-$C_7H_{15}$ | F | |
| 951 | $n$-$C_7H_{15}$ | Cl | |
| 952 | $n$-$C_7H_{15}$ | $CF_3$ | |
| 953 | $n$-$C_7H_{15}$ | $OCF_3$ | |
| 954 | $CH_2$=CH | F | |
| 955 | $CH_2$=CH | Cl | |
| 956 | $CH_2$=CH | $CF_3$ | |
| 957 | $CH_2$=CH | $OCF_3$ | |
| 958 | E-$CH_3$—CH=CH | F | |
| 959 | E-$CH_3$—CH=CH | Cl | |

Note:
*values extrapolated from 10% solution in ZLI-4792.

Examples 960 to 989

Compounds of the formula:

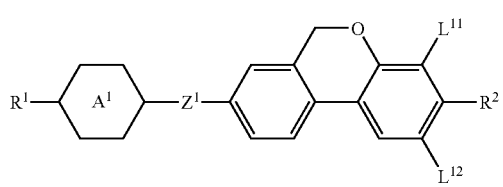

in which

denotes

$L^{11}$ and $L^{12}$ denote H, and $Z^1$ denotes a single bond, are prepared analogously to the preceding examples.

| No. | $R^1$ | $R^2$ | Phase sequence $\Delta\epsilon^*$ T/° C. |
|---|---|---|---|
| 960 | $CH_3$ | F | |
| 961 | $CH_3$ | Cl | |
| 962 | $CH_3$ | $CF_3$ | |
| 963 | $CH_3$ | $OCF_3$ | |
| 964 | $C_2H_5$ | F | |
| 965 | $C_2H_5$ | Cl | |
| 966 | $C_2H_5$ | $CF_3$ | |
| 967 | $C_2H_5$ | $OCF_3$ | |
| 968 | $n$-$C_3H_7$ | F | |
| 969 | $n$-$C_3H_7$ | Cl | |
| 970 | $n$-$C_3H_7$ | $CF_3$ | |
| 971 | $n$-$C_3H_7$ | $OCF_3$ | |
| 972 | $n$-$C_4H_9$ | F | |
| 973 | $n$-$C_4H_9$ | Cl | |
| 974 | $n$-$C_4H_9$ | $CF_3$ | |
| 975 | $n$-$C_4H_9$ | $OCF_3$ | |
| 976 | $n$-$C_5H_{11}$ | F | |
| 977 | $n$-$C_5H_{11}$ | Cl | |
| 978 | $n$-$C_5H_{11}$ | $CF_3$ | |
| 979 | $n$-$C_5H_{11}$ | $OCF_3$ | |
| 980 | $n$-$C_7H_{15}$ | F | |
| 981 | $n$-$C_7H_{15}$ | Cl | |
| 982 | $n$-$C_7H_{15}$ | $CF_3$ | |
| 983 | $n$-$C_7H_{15}$ | $OCF_3$ | |
| 984 | $CH_2$=CH | F | |
| 985 | $CH_2$=CH | Cl | |
| 986 | $CH_2$=CH | $CF_3$ | |
| 987 | $CH_2$=CH | $OCF_3$ | |
| 988 | E-$CH_3$—CH=CH | F | |
| 989 | E-$CH_3$—CH=CH | Cl | |

Note:
*values extrapolated from 10% solution in ZLI-4792.

Examples 990 to 1019

Compounds of the formula:

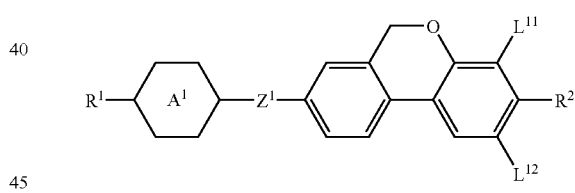

in which

denotes

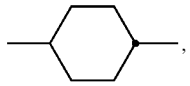

$L^{11}$ denotes H, $L^{12}$ denotes F and $Z^1$ denotes a single bond, are prepared analogously to the preceding examples.

| No. | R$^1$ | R$^2$ | Phase sequence $\Delta\epsilon$* T/° C. |
|---|---|---|---|
| 990 | CH$_3$ | F | |
| 991 | CH$_3$ | Cl | |
| 992 | CH$_3$ | CF$_3$ | |
| 993 | CH$_3$ | OCF$_3$ | |
| 994 | C$_2$H$_5$ | F | |
| 995 | C$_2$H$_5$ | Cl | |
| 996 | C$_2$H$_5$ | CF$_3$ | |
| 997 | C$_2$H$_5$ | OCF$_3$ | |
| 998 | n-C$_3$H$_7$ | F | |
| 999 | n-C$_3$H$_7$ | Cl | |
| 1000 | n-C$_3$H$_7$ | CF$_3$ | |
| 1001 | n-C$_3$H$_7$ | OCF$_3$ | |
| 1002 | n-C$_4$H$_9$ | F | |
| 1003 | n-C$_4$H$_9$ | Cl | |
| 1004 | n-C$_4$H$_9$ | CF$_3$ | |
| 1005 | n-C$_4$H$_9$ | OCF$_3$ | |
| 1006 | n-C$_5$H$_{11}$ | F | |
| 1007 | n-C$_5$H$_{11}$ | Cl | |
| 1008 | n-C$_5$H$_{11}$ | CF$_3$ | |
| 1009 | n-C$_5$H$_{11}$ | OCF$_3$ | |
| 1010 | n-C$_7$H$_{15}$ | F | |
| 1011 | n-C$_7$H$_{15}$ | Cl | |
| 1012 | n-C$_7$H$_{15}$ | CF$_3$ | |
| 1013 | n-C$_7$H$_{15}$ | OCF$_3$ | |
| 1014 | CH$_2$=CH | F | |
| 1015 | CH$_2$=CH | Cl | |
| 1016 | CH$_2$=CH | CF$_3$ | |
| 1017 | CH$_2$=CH | OCF$_3$ | |
| 1018 | E-CH$_3$—CH=CH | F | |
| 1019 | E-CH$_3$—CH=CH | Cl | |

Note:
*values extrapolated from 10% solution in ZLI-4792.

| No. | R$^1$ | R$^2$ | Phase sequence $\Delta\epsilon$* T/° C. |
|---|---|---|---|
| 1020 | CH$_3$ | F | |
| 1021 | CH$_3$ | Cl | |
| 1022 | CH$_3$ | CF$_3$ | |
| 1023 | CH$_3$ | OCF$_3$ | |
| 1024 | C$_2$H$_5$ | F | |
| 1025 | C$_2$H$_5$ | Cl | |
| 1026 | C$_2$H$_5$ | CF$_3$ | |
| 1027 | C$_2$H$_5$ | OCF$_3$ | |
| 1028 | n-C$_3$H$_7$ | F | |
| 1029 | n-C$_3$H$_7$ | Cl | |
| 1030 | n-C$_3$H$_7$ | CF$_3$ | |
| 1031 | n-C$_3$H$_7$ | OCF$_3$ | |
| 1032 | n-C$_4$H$_9$ | F | |
| 1033 | n-C$_4$H$_9$ | Cl | |
| 1034 | n-C$_4$H$_9$ | CF$_3$ | |
| 1035 | n-C$_4$H$_9$ | OCF$_3$ | |
| 1036 | n-C$_5$H$_{11}$ | F | |
| 1037 | n-C$_5$H$_{11}$ | Cl | |
| 1038 | n-C$_5$H$_{11}$ | CF$_3$ | |
| 1039 | n-C$_5$H$_{11}$ | OCF$_3$ | |
| 1040 | n-C$_7$H$_{15}$ | F | |
| 1041 | n-C$_7$H$_{15}$ | Cl | |
| 1042 | n-C$_7$H$_{15}$ | CF$_3$ | |
| 1043 | n-C$_7$H$_{15}$ | OCF$_3$ | |
| 1044 | CH$_2$=CH | F | |
| 1045 | CH$_2$=CH | Cl | |
| 1046 | CH$_2$=CH | CF$_3$ | |
| 1047 | CH$_2$=CH | OCF$_3$ | |
| 1048 | E-CH$_3$—CH=CH | F | |
| 1049 | E-CH$_3$—CH=CH | Cl | |

Note:
*values extrapolated from 10% solution in ZLI-4792.

Examples 1020 to 1049

Compounds of the formula:

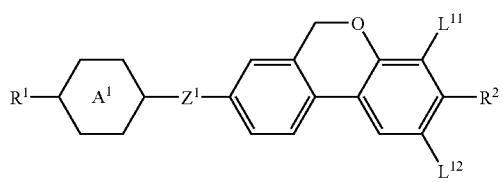

in which

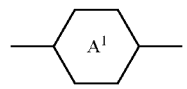

denotes

,

L$^{11}$ denotes F,
L$^{12}$ denotes H and
Z$^1$ denotes a single bond,
are prepared analogously to the preceding examples.

Examples 1050 to 1079

Compounds of the formula:

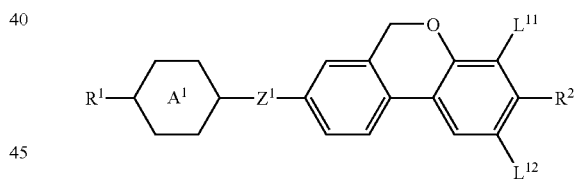

in which

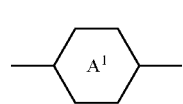

denotes

,

L$^{11}$ and L$^{12}$ denote F and
Z$^1$ denotes a single bond,
are prepared analogously to the preceding examples.

| No. | R¹ | R² | Phase sequence Δε* T/° C. |
|---|---|---|---|
| 1050 | CH₃ | F | |
| 1051 | CH₃ | Cl | |
| 1052 | CH₃ | CF₃ | |
| 1053 | CH₃ | OCF₃ | |
| 1054 | C₂H₅ | F | |
| 1055 | C₂H₅ | Cl | |
| 1056 | C₂H₅ | CF₃ | |
| 1057 | C₂H₅ | OCF₃ | |
| 1058 | n-C₃H₇ | F | |
| 1059 | n-C₃H₇ | Cl | |
| 1060 | n-C₃H₇ | CF₃ | |
| 1061 | n-C₃H₇ | OCF₃ | |
| 1062 | n-C₄H₉ | F | |
| 1063 | n-C₄H₉ | Cl | |
| 1034 | n-C₄H₉ | CF₃ | |
| 1065 | n-C₄H₉ | OCF₃ | |
| 1066 | n-C₅H₁₁ | F | |
| 1067 | n-C₅H₁₁ | Cl | |
| 1068 | n-C₅H₁₁ | CF₃ | |
| 1069 | n-C₅H₁₁ | OCF₃ | |
| 1070 | n-C₇H₁₅ | F | |
| 1071 | n-C₇H₁₅ | Cl | |
| 1072 | n-C₇H₁₅ | CF₃ | |
| 1073 | n-C₇H₁₅ | OCF₃ | |
| 1074 | CH₂=CH | F | |
| 1075 | CH₂=CH | Cl | |
| 1076 | CH₂=CH | CF₃ | |
| 1077 | CH₂=CH | OCF₃ | |
| 1078 | E-CH₃—CH=CH | F | |
| 1079 | E-CH₃—CH=CH | Cl | |

Note:
*values extrapolated from 10% solution in ZLI-4792.

MIXTURE EXAMPLES

Liquid-crystalline mixtures are prepared and investigated for their applicational properties.

Example M 1

A liquid-crystal mixture having the composition indicated in the following table was prepared and investigated. It has the properties likewise shown in the table.

| | Composition | |
|---|---|---|
| Compound # | Abbreviation | Conc./ weight-% |
| 1 | CCP-3OCF3 | 7 |
| 2 | CCG-V-F | 6 |
| 3 | CCP-3F•F•F | 7 |
| 4 | ECCP-3F•F | 12 |
| 5 | ECCP-5F•F | 10 |
| 6 | BCH-2F•F | 9 |
| 7 | BCH-3F•F•F | 13 |
| 8 | CC-3-V1 | 6 |
| 9 | CC-5-V | 10 |
| 10 | BCH-32F | 7 |
| 11 | BCH-52F | 5 |
| 12 | Comp. Ex. 1 | 6 |
| Σ | | 100.0 |

| Physical properties | |
|---|---|
| T(N, I) = | 92.2° C. |
| Δn (20° C., 589 nm) = | 0.1053 |
| Δε (20° C., 1 kHz) = | 6.6 |
| γ₁ (20° C.) = | 148 mPa · s |

The liquid-crystal medium has very good applicational properties and can be employed for various AMD technologies, such as TN and IPS displays.

The invention claimed is:

1. A dielectrically positive compound of formula I

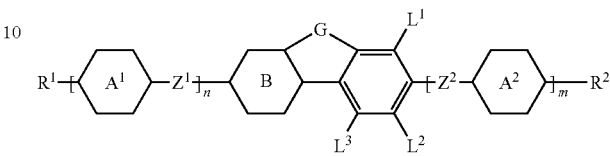

I in which

G denotes —CO—O—, —CH₂—O—, —CF₂—O—, —O—CO—, —O—CH₂— or —O—CF₂—,

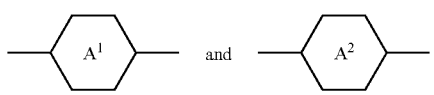

each, independently of one another and, if present more than once, also these independently of one another, denote (a) a trans-1,4-cyclohexylene radical, in which, in addition, one or two non-adjacent CH₂ groups may be replaced by —O— and/or —S—, (b) a 1,4-cyclohexenylene radical, (c) a 1,4-phenylene radical, in which, in addition, one or two non-adjacent CH groups may be replaced by N, or (d) naphthalene-2,6-diyl, decahydronaphthalene-2,6-diyl and 1,2,3,4-tetrahydronaphthalene-2,6-diyl, (e) a radical selected from the group 1,4-bicyclo[2.2.2]octylene, 1,3-bicyclo[1.1.1]pentylene, spiro[3.3]heptane-2,6-diyl and 1,3-cyclobutylene, where in (a) and (b), one or more —CH₂— groups, independently of one another, may each be replaced by a —CHF— or —CF₂— group, and in (c) and (d), one or more —CH= groups, independently of one another, may each be replaced by a —CF=, —C(CN)=, —C(CH₃)=, —C(CH₂F)=, —C(CHF₂)=, —C(O—CH₃)=, —C(O—CHF₂)= or —C(O—CF₃)= group, L¹ to L³ each, independently of one another, denote H, halogen, —CN or —CF₃,

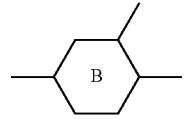

denotes a 1,4-trans-cyclohexane-1,2,4-triyl radical, which may optionally contain one, two or three C—C double bonds, R¹ and R² each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —SF₅, —CF₃, —CHF₂, —CH₂F, —OCF₃, —OCHF₂, an alkyl group having 1 to 15 C atoms which is monosubstituted by —CN or —CF$_3$ or at least monosubstituted by halogen, where, in addition, one or more CH$_2$ groups, in each case independently of one another, may be replaced by —O—, —S—, —CH═CH—, —CF═CF—, —CF═CH—, —CH═CF—,

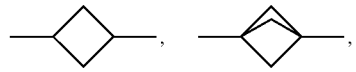

—CO—, —CO—O—, —O—CO— or —O—CO—O— in such a way that neither O nor S atoms are linked directly to one another, and one of R$^1$ or R$^2$ is halogen, —CN, —SCN, —NCS, —OCN, —SF$_5$, —CF$_3$, —CHF$_2$, —CH$_2$F, —OCF$_3$, or —OCHF$_2$, Z$^1$ and Z$^2$ each, independently of one another and, if present more than once, also these independently of one another, denote —CH$_2$—CH$_2$—, —(CH$_2$)$_4$—, —CF$_2$—CF$_2$—, —CF$_2$—CH$_2$—, —CH$_2$—CF$_2$—, —CH═CH—, —CF═CF—, —CF═CH—, —CH═CF—, —C≡C—, —CO—O—, —O—CO—, —CH$_2$—O—, —O—CH$_2$—, —CF$_2$—O—, —O—CF$_2$—, or a combination of two of these groups, where no two O atoms are bonded to one another, n and m each denote 0, 1 or 2, where
n+m denotes 0, 1, 2 or 3.

2. A compound of the formula I according to claim 1, wherein

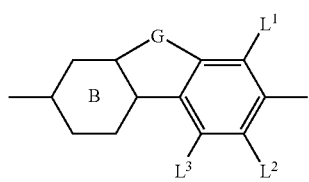

denotes

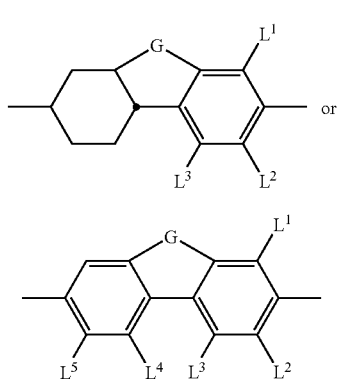

in which the parameters have the meaning given in claim 1 and L$^4$ and L$^5$ each donate H.

3. A compound according to claim 1, of the sub-formulae I-A or I-B

I-A
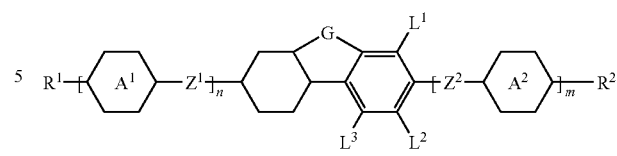

I-B
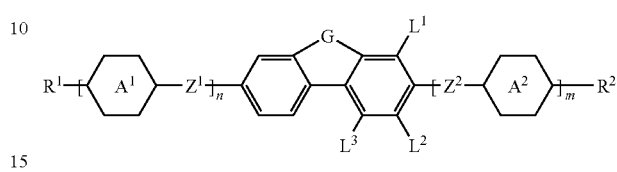

in which the parameters have the meaning given in claim 1.

4. A compound according to claim 1, of the sub-formulae I-A1 to I-A3 or I-B1 to I-B3

I-A1
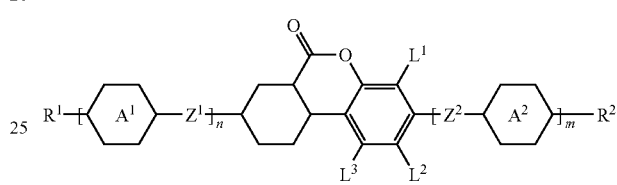

I-A2
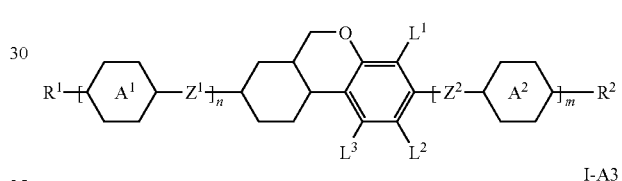

I-A3
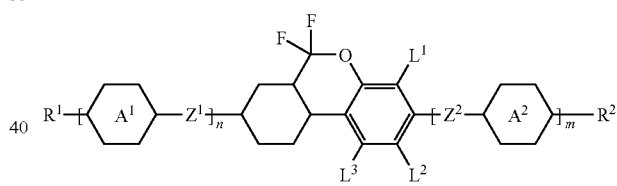

I-B1
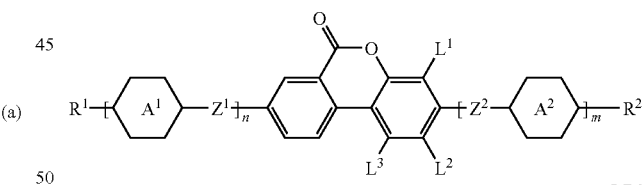

I-B2
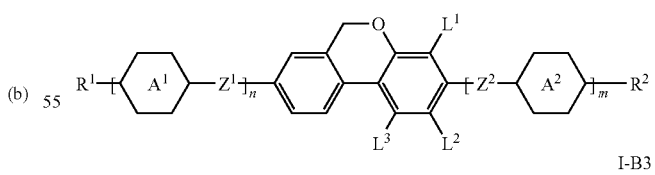

I-B3
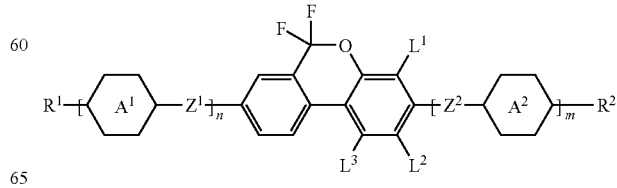

in which the parameters have the meaning given in claim 1.

5. A compound according to claim 1, wherein $Z^1$ and $Z^2$ both denote a single bond.

6. A liquid-crystal medium, comprising one or more compounds of formula I as defined in claim 1.

7. The liquid-crystal medium according to claim 6, having a nematic phase.

8. A liquid-crystal medium, comprising a dielectrically positive compound formula I

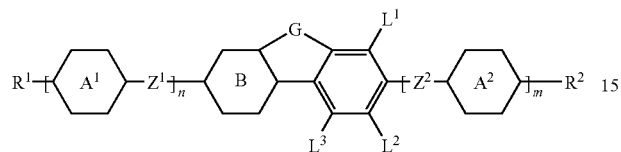

in which
G denotes —CO—O—, —CH$_2$—O—, —CF$_2$—O—, —O—CO—, —O—CH$_2$— or —O—CF$_2$—,

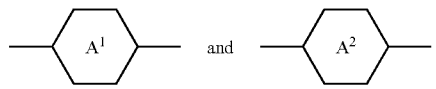

each, independently of one another and, if present more than once, also these independently of one another, denote
(a) a trans-1,4-cyclohexylene radical, in which, in addition, one or two non-adjacent CH$_2$ groups may be replaced by —O— and/or —S—,
(b) a 1,4-cyclohexenylene radical,
(c) a 1,4-phenylene radical, in which, in addition, one or two non-adjacent CH groups may be replaced by N, or
(d) naphthalene-2,6-diyl, decahydronaphthalene-2,6-diyl and 1,2,3,4-tetrahydronaphthalene-2,6-diyl,
(e) a radical selected from the group 1,4-bicyclor[2.2.2]octylene, 1,3-bicyclor[1.1.1]pentylene, spiror[3.3]heptane-2,6-diyl and 1,3-cyclobutylene,
where in
(a) and (b), one or more —CH$_2$— groups, independently of one another, may each be replaced by a —CHF— or —CF$_2$—group, and in
(c) and (d), one or more —CH═ groups, independently of one another, may each be replaced by a —CF═, —C(CN)═, —C(CH$_3$)═, —C(CH$_2$F)═, —C(CHF$_2$)═, —C(O—CH$_3$)═, —C(O—CHF$_2$)═ or —C(O—CF$_3$)═ group
$L^1$ to $L^3$ each, independently of one another, denote H, halogen, —CN or —CF$_3$,

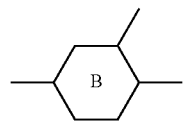

denotes a 1,4-trans-cyclohexane-1,2,4-triyl radical, which may optionally contain one, two or three C—C double bonds,
$R^1$ and $R^2$ each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —SF$_5$, —CF$_3$ —CHF$_2$, —CH$_2$F, —OCF$_3$, —OCHF$_2$, an alkyl group having 1 to 15 C atoms which is monosubstituted by —CN or —CF$_3$ or at least monosubstituted by halogen, where, in addition, one or more CH$_2$ groups, in each case independently of one another, may be replaced by —O—, —S—, —CH═CH—, —CF═CF—, —CF═CH—, —CH═CF—,

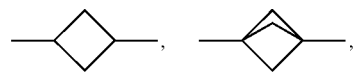

—CO—, —CO—O—, —O—CO— or —O—CO—O— in such a way that neither O nor S atoms are linked directly to one another,
$Z^1$ and $Z^2$ each, independently of one another and, if present more than once, also these independently of one another, denote —CH$_2$—CH$_2$—, —(CH$_2$)$_4$—, —CF$_2$—CF$_2$—, —CF$_2$—CH$_2$—, —CH$_2$—CF$_2$—, —CH═CH—, —CF═CF—, —CF═CH—, —CH═CF—, —C≡C—, —CO—O—, —O—CO—, —CH$_2$—O—, —O—CH$_2$—, —CF$_2$—O—, —O—CF$_2$—, or a combination of two of these groups, where no two O atoms are bonded to one another,
n and m each denote 0, 1 or 2, where
n+m denotes 0, 1, 2 or 3
further comprising
one or more dielectrically positive compound(s) of formula II

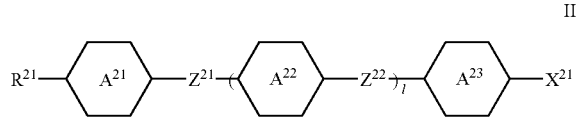

in which
$R^{21}$ has the same meaning as $R^1$,
$X^{21}$ denotes halogen, —CN, —SCN, —NCS, —OCN, —SF$_5$, —CF$_3$, —CHF$_2$, —CH$_2$F, —OCF$_3$, —OCHF$_2$, an alkyl group having 1 to 15 C atoms which is monosubstituted by CN or CF$_3$ or at least monosubstituted by halogen and in which one or more CH$_2$ groups, in each case independently of one another, may be replaced by —O—, —S—, —CH═CH—, —CF═CF—, —CF═CH—, —CH═CF—,

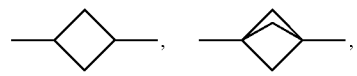

—CO—, —CO—O—, —O—CO— or —O—CO—O— in such a way that neither O nor S atoms are linked directly to one another,
$Z^{21}$ and $Z^{22}$ each, independently of one another, have the same meaning as $Z^1$,
at least one of the rings present

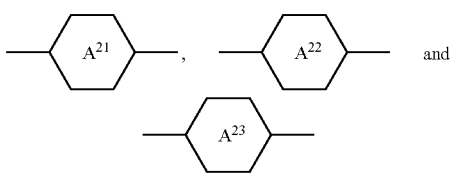

denotes

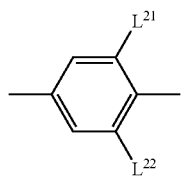

and the others, in each case independently of one another, denote

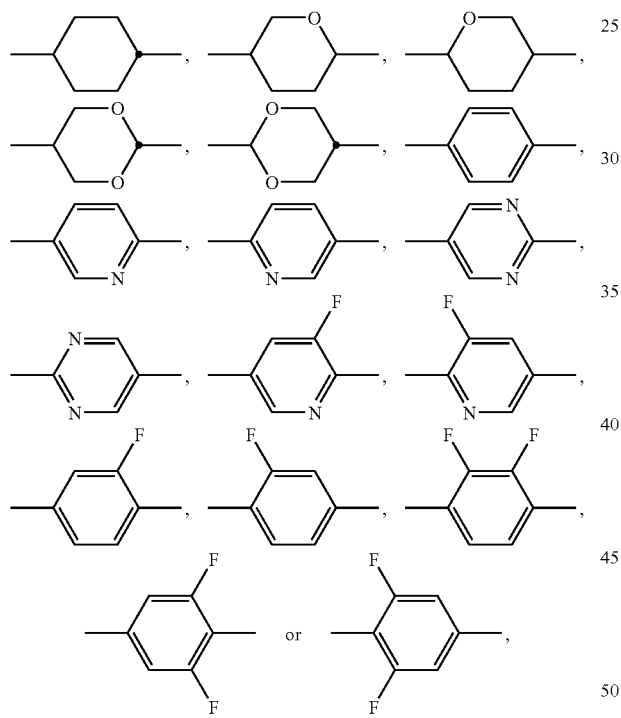

$L^{21}$ and $L^{22}$, independently of one another, denote H or F, l denotes 0, 1 or 2.

9. A liquid-crystal medium, comprising a dielectrically positive compound of Formula I

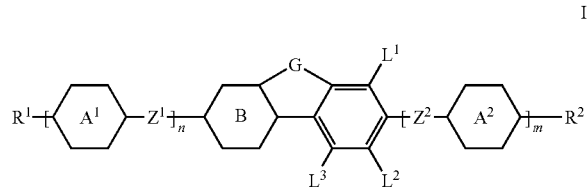

I in which
G denotes —CO—O—, —CH$_2$—O—, —CF$_2$—O—, —O—CO—, —O—CH$_2$— or —O—CF$_2$,

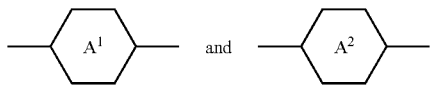

each, independently of one another and, if present more than once, also these independently of one another, denote
(a) a trans-1,4-cyclohexylene radical, in which, in addition, one or two non-adjacent CH$_2$ groups may be replaced by —O— and/or —S—,
(b) a 1,4-cyclohexenylene radical,
(c) a 1,4-phenylene radical, in which, in addition, one or two non-adjacent CH groups may be replaced by N, or
(d) naphthalene-2,6-diyl, decahydronaphthalene-2,6-diyl and 1,2,3,4-tetrahydronaphthalene-2,6-diyl,
(e) a radical selected from the group 1,4-bicyclo[2.2.2]octylene, 1,3-bicyclo[1.1.1]pentylene, spiro[3.3]heptane-2,6-diyl and 1,3-cyclobutylene,
where in
(a) and (b), one or more —CH$_2$— groups, independently of one another, may each be replaced by a —CHF— or —CF$_2$—group, and in
(c) and (d), one or more —CH═ groups, independently of one another, may each be replaced by a —CF═, —C(CN)═, —C(CH$_3$)═, —C(CH$_2$F)═, —C(CHF$_2$)═, —C(O—CH$_3$)═, —C(O—CHF$_2$)═ or —C(O—CF$_3$)═ group,
$L^1$ to $L^3$ each, independently of one another, denote H, halogen, —CN or —CF$_3$,

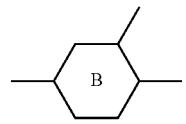

denotes a 1,4-trans-cyclohexane-1,2,4-triyl radical, which may optionally contain one, two or three C—C double bonds,
$R^1$ and $R^2$ each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —SF$_5$, —CF$_3$ —CHF$_2$, —CH$_2$F, —OCF$_3$, —OCHF$_2$, an alkyl group having 1 to 15 C atoms which is monosubstituted by —CN or —CF$_3$ or at least monosubstituted by halogen, where, in addition, one or more CH$_2$ groups, in each case independently of one another, may be replaced by —O—, —S—, —CH═CH—, —CF═CF—, —CF═CH—, —CH═CF—,

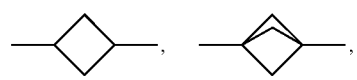

—CO—, —CO—O—, —O—CO— or —O—CO—O— in such a way that neither O nor S atoms are linked directly to one another, $Z^1$ and $Z^2$ each, independently of one another and, if present more than once, also these independently of one another, denote —CH$_2$—CH$_2$—, —(CH$_2$)$_4$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —CO—O—, —O—CO—, —CH$_2$—O—, —O—CH$_2$—, —CF$_2$—O—, —O—CF$_2$—, or a combination of two of these groups, where no two O atoms are bonded to one another, n and m each denote 0, 1 or 2, where n+m denotes 0, 1, 2 or 3 further comprising one or more dielectrically neutral compound(s) of formula III

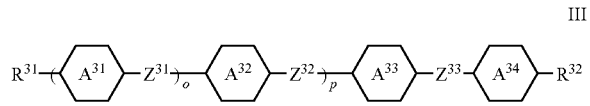

III in which $R^{31}$ and $R^{32}$ each, independently of one another, have the meaning given above for $R^1$ in the case of formula I, and $Z^{31}$, $Z^{32}$ and $Z^{33}$ each, independently of one another, denote —CH$_2$CH$_2$—, —CH=CH—, —COO— or a single bond,

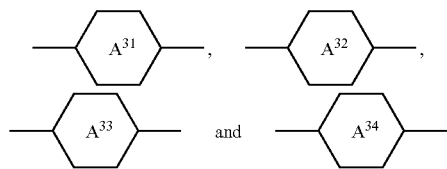

each, independently of one another, denote

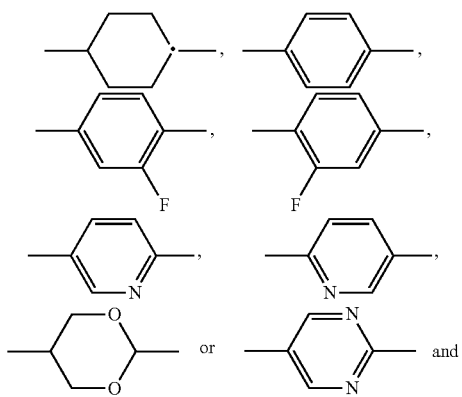

o and p, independently of one another, denote 0 or 1, where in the case of the phenylene ring, one or more H atoms, independently of one another, may be replaced by F or CN, and one or two non-adjacent CH$_2$ groups of the cyclohexylene ring or of one of the cyclohexylene rings may be replaced by O atoms.

10. An electro-optical display containing a liquid-crystal medium according to claim 6.

11. A pharmaceutical composition, comprising at least one compound of formula I according to claim 1 and/or physiologically acceptable salts or solvates thereof, and a pharmaceutically acceptable carrier.

12. A method for the treatment of diseases or symptoms which can be influenced by inhibition of cannabinoid receptors, comprising administering to a host in need thereof an effective amount of a compound according to claim 1.

13. A method for the treatment of psychoses, anxiety disorders, depression, aprosexia, memory disorders, cognitive disorders, loss of appetite, obesity, addiction, drug dependence, neurological disorders, neurodegenerative processes, dementia, dystonia, muscle spasms, tremor, epilepsy, multiple sclerosis, traumatic brain injuries, strokes, Parkinson's, Alzheimer's, Huntington's disease, Tourette's syndrome, cerebral ischaemia, cerebral apoplexy, craniocerebral trauma, spinal cord injuries, neuroinflammatory diseases, cerebral arteriosclerosis, viral encephalitis, diseases associated with demyelination, pain , including neuropathic pain diseases, septic shock, glaucoma, cancer, diabetes, vomiting, nausea, asthma, respiratory tract diseases, gastrointestinal diseases, gastric ulcers, diarrhoea or cardiovascular diseases, comprising administering to a host in need thereof an effective amount of a compound according to claim 1.

14. The compound according to claim 1, wherein one of $R^1$ or $R^2$ is —F, —Cl, —CF$_3$ or OCF$_3$.

15. The compound according to claim 1, wherein $R^1$ and $R^2$ each, independently of one another, denote alkyl or alkoxy having 1 to 15 C atoms, alkoxyalkyl, alkenyl or alkenyloxy having 2 to 15 C atoms, alkynyl or alkynyloxy having 2 to 15 C atoms, H, halogen, —CN, —SCN, —NCS, —OCN, —SF$_5$, —CF$_3$, —CHF$_2$, —CH$_2$F, —OCF$_3$, —OCHF$_2$, an alkyl group having 1 to 15 C atoms which is monosubstituted by —CN or —CF$_3$ or at least monosubstituted by halogen, where, in addition, one or more CH$_2$ groups, in each case independently of one another, may be replaced by —S—, —CH=CH—, —CF=CF—, —CF=CH—, —CH=CF—,

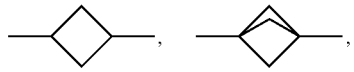

—CO—, —CO—O—, —O—CO— or —O—CO—O— in such a way that neither O nor S atoms are linked directly to one another, and one of $R^1$ or $R^2$ is halogen, —CN, —SCN, —NCS, —OCN, —SF$_5$, —CF$_3$, —CHF$_2$, —CH$_2$F, OCF$_3$, or —OCHF$_2$.

* * * * *